(12) United States Patent
Pulford et al.

(10) Patent No.: US 8,501,908 B2
(45) Date of Patent: Aug. 6, 2013

(54) IMMUNOGENIC PEPTIDES

(75) Inventors: Karen Pulford, Oxford (GB); Alison Banham, Oxford (GB); Amanda Anderson, Oxford (GB); Kamel Ait-Tahar, Oxford (GB)

(73) Assignee: Isis Innovation Ltd., Oxford (GB)

( * ) Notice: Subject to any disclaimer, the term of this patent is extended or adjusted under 35 U.S.C. 154(b) by 0 days.

(21) Appl. No.: 13/121,447

(22) PCT Filed: Oct. 1, 2009

(86) PCT No.: PCT/GB2009/002332
§ 371 (c)(1),
(2), (4) Date: Jun. 17, 2011

(87) PCT Pub. No.: WO2010/038020
PCT Pub. Date: Apr. 8, 2010

(65) Prior Publication Data
US 2012/0042399 A1    Feb. 16, 2012

(30) Foreign Application Priority Data
Oct. 2, 2008  (GB) ..................................... 0818080

(51) Int. Cl.
*A61K 38/00*  (2006.01)
*A61K 39/00*  (2006.01)

(52) U.S. Cl.
USPC ........................................ 530/300; 424/184.1

(58) Field of Classification Search
None
See application file for complete search history.

(56) References Cited

FOREIGN PATENT DOCUMENTS

| WO | 00/09657 | 2/2000 |
|---|---|---|
| WO | 03/082916 | 10/2003 |
| WO | 2005/049072 | 6/2005 |

OTHER PUBLICATIONS

Kiecker et al., (Human Immunology, 2004, 65: 523-536.*
Komenaka et al., Clinics in Dermatology, 2004, 22: 251-265.*
Evans et al., Q. J. Med 1999: 92: 299-307.*
International Search Report and Written Opinion corresponding to International Patent Application No. PCT/GB2009/002332, mailed Dec. 30, 2009.
Liggins et al., "A novel diffuse large B-cell lymphoma-associated cancer testis antigen encoding a PAS domain protein." British Journal of Cancer, vol. 91, No. 1, Jul. 5, 2004. XP002509775.
Combined Search and Examination Report under Sections 17 and 18(3) corresponding to Great Britain Patent Application Serial No. GB0818080.4, dated Jul. 1, 2009.
Leukemia 20 (2006) Cooper et al. PASD1, a DLBCL-associated cancer testis antigen and candidate for lymphoma immunotherapy. 2172-2174.
Biochemical and Biophysical Research Communications 335 (2005) Guinn et al., "Humoral detection of leukaemia-associated antigens in presentation acute myeloid leukaemia" 1293-1304.
Blood 106 (2005) Cooper et al., Protein expression profiles confirm PASD1 as a cancer testis antigen and a potential candidate for lymphoma immunotherapy 792A.
Blood 108 (2006) Sahota et al., 'PASD1 is a potential multiple myeloma-associated antigen' 3953-3955.

* cited by examiner

*Primary Examiner* — Hong Sang
(74) *Attorney, Agent, or Firm* — McAndrews, Held & Malloy, Ltd.

(57) ABSTRACT

The present invention relates to immunogenic peptides and their various applications. In particular the invention relates to immunogenic peptides derived from the PASD1 protein and their use in therapeutic, diagnostic and prognostic methods.

13 Claims, 18 Drawing Sheets

```
SEQUENCE LISTING

<160> NUMBER OF SEQ ID NOS: 28

<210> SEQ ID NO 1
<211> LENGTH: 10
<212> TYPE: PRT
<213> ORGANISM: Homo sapiens

<400> SEQUENCE: 1

Gln Leu Leu Asp Gly Phe Met Ile Thr Leu
1               5                   10

<210> SEQ ID NO 2
<211> LENGTH: 9
<212> TYPE: PRT
<213> ORGANISM: Homo sapiens

<400> SEQUENCE: 2

Tyr Leu Val Gly Asn Val Cys Ile Leu
1               5

<210> SEQ ID NO 3
<211> LENGTH: 9
<212> TYPE: PRT
<213> ORGANISM: Homo sapiens

<400> SEQUENCE: 3

Leu Leu Gly His Leu Pro Ala Glu Ile
1               5
```

```
<210> SEQ ID NO 4
<211> LENGTH: 9
<212> TYPE: PRT
<213> ORGANISM: Homo sapiens

<400> SEQUENCE: 4

Gln Leu Arg Glu Gln Leu Gln Gln Leu
1               5

<210> SEQ ID NO 5
<211> LENGTH: 9
<212> TYPE: PRT
<213> ORGANISM: Homo sapiens

<400> SEQUENCE: 5

Glu Leu Ser Asp Ser Leu Gly Pro Val
1               5

<210> SEQ ID NO 6
<211> LENGTH: 20
<212> TYPE: PRT
<213> ORGANISM: Homo sapiens

<400> SEQUENCE: 6

Asp Tyr Phe Asn Gln Val Thr Leu Gln Leu Asp Gly Phe Met Ile
1               5                   10                  15

Thr Leu Ser Thr
            20

<210> SEQ ID NO 7
<211> LENGTH: 20
<212> TYPE: PRT
<213> ORGANISM: Homo sapiens

<400> SEQUENCE: 7

Asp Gly Phe Met Ile Thr Leu Ser Thr Asp Gly Val Ile Ile Cys Val
1               5                   10                  15

Ala Glu Asn Ile
            20

<210> SEQ ID NO 8
<211> LENGTH: 20
<212> TYPE: PRT
<213> ORGANISM: Homo sapiens

<400> SEQUENCE: 8

Ala Glu Asn Ile Ser Ser Leu Leu Gly His Leu Pro Ala Glu Ile Val
1               5                   10                  15

Gly Lys Lys Leu
            20

<210> SEQ ID NO 9
<211> LENGTH: 20
<212> TYPE: PRT
<213> ORGANISM: Homo sapiens

<400> SEQUENCE: 9

Val Gly Asn Val Cys Ile Leu Arg Thr Gln Leu Leu Gln Gln Leu Tyr
1               5                   10                  15

Thr Ser Lys Ala
            20
```

```
<210> SEQ ID NO 10
<211> LENGTH: 20
<212> TYPE: PRT
<213> ORGANISM: Homo sapiens

<400> SEQUENCE: 10

Asn His Pro Val Arg Phe Leu Gln Ala Gln Pro Ile Val Pro Val Gln
1               5                   10                  15

Arg Ala Ala Glu
            20

<210> SEQ ID NO 11
<211> LENGTH: 30
<212> TYPE: DNA
<213> ORGANISM: Homo sapiens

<400> SEQUENCE: 11
cagctgctgg atggctttat gattaccctg                                      30

<210> SEQ ID NO 12
<211> LENGTH: 27
<212> TYPE: DNA
<213> ORGANISM: Homo sapiens

<400> SEQUENCE: 12
tatctggtgg gcaacgtgtg cattctg                                         27

<210> SEQ ID NO 13
<211> LENGTH: 27
<212> TYPE: DNA
<213> ORGANISM: Homo sapiens

<400> SEQUENCE: 13
ctgctgggcc atctgccggc ggaaatt                                         27

<210> SEQ ID NO 14
<211> LENGTH: 27
<212> TYPE: DNA
<213> ORGANISM: Homo sapiens

<400> SEQUENCE: 14
cagctgcgcg aacagctgca gcagctg                                         27

<210> SEQ ID NO 15
<211> LENGTH: 27
<212> TYPE: DNA
<213> ORGANISM: Homo sapiens

<400> SEQUENCE: 15
gaactgagcg atagcctggg cccggtg                                         27

<210> SEQ ID NO 16
<211> LENGTH: 60
<212> TYPE: DNA
<213> ORGANISM: Homo sapiens

<400> SEQUENCE: 16
gattatttta accaggtgac cctgcagctg ctggatggct ttatgattac cctgagcacc     60

<210> SEQ ID NO 17
<211> LENGTH: 60
<212> TYPE: DNA
<213> ORGANISM: Homo sapiens

<400> SEQUENCE: 17
```

```
gatggcttta tgattaccct gagcaccgat ggcgtgatta tttgcgtggc ggaaaacatt    60
```

<210> SEQ ID NO 18
<211> LENGTH: 60
<212> TYPE: DNA
<213> ORGANISM: Homo sapiens

<400> SEQUENCE: 18

```
gcggaaaaca ttagcagcct gctgggccat ctgccggcgg aaattgtggg caaaaaactg    60
```

<210> SEQ ID NO 19
<211> LENGTH: 60
<212> TYPE: DNA
<213> ORGANISM: Homo sapiens

<400> SEQUENCE: 19

```
gtgggcaacg tgtgcattct gcgcacccag ctgctgcagc agctgtatac cagcaaagcg    60
```

<210> SEQ ID NO 20
<211> LENGTH: 60
<212> TYPE: DNA
<213> ORGANISM: Homo sapiens

<400> SEQUENCE: 20

```
aaccatccgg tgcgctttct gcaggcgcag ccgattgtgc cggtgcagcg cgcggcggaa    60
```

<210> SEQ ID NO 21
<211> LENGTH: 4109
<212> TYPE: DNA
<213> ORGANISM: Homo sapiens

<400> SEQUENCE: 21

```
cagactttcc gggcgcccac caggctcccg gctctcacc ggagaccaca gggaggagct     60
tcaaggtacc ccaagtccct gcggcctcca gcagtgaaga gttccacaag ggagtcttcc   120
tacgtcactg aataatgaat gaagatgaga ggggaaaaga gaagagacaa agtcaatcca   180
aaaagctctc aaaggaaatt aaactggatt ccatcatttc ctaccatga ttacttcaac    240
caagtgacgc tacagttatt agatggcttt atgattacac tgagcacaga tggagtgatc   300
atttgtgtgg ctgaaaacat ctcttctctt cttggacatt taccagctga gattgtgggc   360
aaaaaattat taagccttct gcctgatgaa gagaaagatg aagtctacca aaagattatt   420
ctcaaatttc ctttactaaa ctcagaaaca catattgaat tttgctgtca tttaaaaaga   480
ggaaatgtcg aacatggtga tagttctgct tacgaaaacg tgaaatttat tgtgaatgta   540
agagatattt gtaatgagtt tcctgtggtc tttagtggct tgttttccag ccacctctgt   600
gctgactttg ctgcatgtgt tcctcaggag gatcggcttt atcttgtggg aaatgtttgc   660
attctcagga tcagctcct gcagcaactt tacacttcaa aggcagtcag tgatgaagct   720
gtacttacac aagattcaga tgaggaacct tttgtgggag agctcagtag ctctcaaggt   780
caaagaggac acactagcat gaaagccgtg tacgttgaac ccgctgctgc tgctgctgct   840
gctgctatct cagacgacca aattgatatt gcagaggttg agcagtatgg accacaagaa   900
aacgttcaca tgtttgtaga ttctgattca acttattgct ccagtacagt tttcctggat   960
actatgcctg aatctccagc cttatccttg caagactttc gaggtgagcc tgaggtgaat  1020
ccattgtaca gggcagaccc agtggacctg gagttctcgg tggatcaggt ggactcagtg  1080
gaccaggagg gcccaatgga ccagcaggac ccagagaacc cagttgcccc gttggaccag  1140
gcaggcctga tggatccagt ggatccagag gactcagtgg acctgggggc tgctggcgca  1200
```

```
agtgctcagc cattacagcc atcatcacca gttgcatatg acatcattag ccaggaactg    1260
gaactgatga agaagttgaa ggagcagcta gaagagagga cttggttgct gcatgatgcc    1320
atccaaaacc agcagaatgc attggaattg atgatggatc accttcagaa gcagccaaac    1380
acattacgcc acgttgtcat tcctgatctc aatcttcgg aggcagtgcc caagaaacaa    1440
cagaaacaac acgctgggca agtgaagcgg cctctcccac atcccaagga cgtcaagtgt    1500
ttctgtggct tatctttatc caactctctc aaaaacactg gggagcttca ggagccttgt    1560
gttgccttca accagcagca actggtgcag caagaacaac acctgaagga gcagcagcgg    1620
cagctgcggg agcagctgca acagctgaga gagcaaagga aggtgcagaa gcagaagaag    1680
atgcaggaga agaagaagct gcaggagcag aaaatgcagg agaagaagaa gctgcaggag    1740
cagaggcggc aaaagaagaa gaagctacag gagcggaaga agtggcaggg gcagatgcta    1800
cagaaagagc cagaggagga gcagcagaag cagcagctgc aagagcagcc actgaagcat    1860
aatgtcatcg tggggaatga gagggtgcag atatgcctgc aaaacccacg tgacgtatct    1920
gtgcccctct gcaatcaccc tgttagattt ttacaggccc aacccattgt tcctgtccag    1980
agagcagctg aacaacagcc ctctggcttc tatcaagatg aaaactgtgg gcaacaggaa    2040
gatgagagtc aaaggtaaga catgcatgga atggtgatag tggctatgat tattgctttt    2100
ccctcatggc tggatcccat gcctgagatc acagacagac gacctatcca tgtggcacca    2160
gcgtccctct catcaatagc aacttgctct caacttgcct tctctgtggc cacggccatc    2220
atccttctgc atgtgtggtg catggatgag catccattga tggaacaaag gggtacccat    2280
gaagaaagga ctagataagg aagcctcaat gctagggaat tagcccacaa accttgaaat    2340
cacttggctg gattccccaa gcccagtctc ttgcacaggg tgtctatgga caagtcttgt    2400
gcccatagct gaaagacttc tgggcttcca gtttcattcc ccaactttcc tggaatctgg    2460
tgatggcagt aggccaagtg caggtatctc cctggcattt atgaacagta agagggaagt    2520
gagtgtgaaa caattgctag attgctaaga tcagccaaga acacatgaag gctaagtcct    2580
gagtggcaat atagggacat gaacacattt ctgctcaata taaggtctt cagttccaaa    2640 tgctagaaag ataaggttct tctcagcaat gaaaggattg cttagcacat agttggggcc    2700
cactaaatag ttttgaatga atgttagctt tctgagacgg gcctcctaaa gctctctgga    2760
cttccttctg ggccttgctt tcgaatcagt gactttgaca tgaagactgc tttagggcca    2820
tattgtccac ttgacctgat catcagaatc cacctgagga gggtttggaa agtatagatt    2880
cagagtctgg gatggggttc aaaaatctgt attgatcaca agacttccag gcttagggtt    2940
gtggagagag cactggattt ggagtttgga aatctgcctt acagtctctg ctcagccatt    3000
agctccctga gtgctttcaa agtaggtgaa atgactttcc aaggccacag agagcatagt    3060
tgtagcagga acaagactgt ccaagtaata taaataaaac caggtgagac aagggattgt    3120
aatttctctc agtgtctaca ttcacattac tttgacaagt tgaatcttag tcaggccaaa    3180
gtgagaatac aaacaagtga atcctgtggt gtagccacca aaaccaaatg tgcctgaagc    3240
acctactgat gaccacgtga gtgtctcatc agttatcatg tccagatcca catcactgca    3300
acagctttct tctcttacag tttttatcct gaggcgtatc aagggccccc cgtgaaccag    3360
ctgccattga tagataccctc aaactctgag gcaatttctt cttccagcat tcctcagttt    3420
cccataactt cagactcaac cataagcacc ctggagaccc cacaggatta catccggctt    3480
tggcaagagt tgtctgattc actcggtcct gttgtccaag tgaacacttg gtcttgcgat    3540
gagcagggca ccctgcacgg ccaacccacc taccatcagg tgcaagtttc tgaggtagga    3600
```

```
gtcgagggac tcctgatcc acaggctttc caaggccctg ctgcatacca gccagaccag    3660
atgagatctg cggagcagac cagattgatg cctgcagagc aacgtgactc aaataagccg    3720
tgctaacagt actttcatga ccagtgatga ggggaaatgg ggggaggggg caggccaatg    3780
aggtctgcat ggccagggga ccttcaaggt gcataaagtc ccttggggta gggtttagtg    3840
ggtagagact tgtttcctga taggttatgt ttgtaattgt ttgttaagca cagcctgttt    3900
cttggaagtt atgctgtaga ggcagcctgt gatccgtagt atgctagggt gtgacagcag    3960
ccagccacag ctggatctga tgtcttgtct gccccgccca gctttgcata tccatgttct    4020
accacaggaa ggtggcctgc caagagtctg ctcaaagttt tcaacataaa gaataaagaa    4080
aaaaaaatgc aaaaaaaaa aaaaaaaa                                         4109
```

<210> SEQ ID NO 22
<211> LENGTH: 639
<212> TYPE: PRT
<213> ORGANISM: Homo sapiens

<400> SEQUENCE: 22

```
Met Lys Met Arg Gly Glu Lys Arg Arg Asp Lys Val Asn Pro Lys Ser
1               5                   10                  15

Ser Gln Arg Lys Leu Asn Trp Ile Pro Ser Phe Pro Thr Tyr Asp Tyr
                20                  25                  30

Phe Asn Gln Val Thr Leu Gln Leu Leu Asp Gly Phe Met Ile Thr Leu
            35                  40                  45

Ser Thr Asp Gly Val Ile Ile Cys Val Ala Glu Asn Ile Ser Ser Leu
        50                  55                  60

Leu Gly His Leu Pro Ala Glu Ile Val Gly Lys Lys Leu Leu Ser Leu
65                  70                  75                  80

Leu Pro Asp Glu Glu Lys Asp Glu Val Tyr Gln Lys Ile Ile Leu Lys
                85                  90                  95

Phe Pro Leu Leu Asn Ser Glu Thr His Ile Glu Phe Cys Cys His Leu
            100                 105                 110

Lys Arg Gly Asn Val Glu His Gly Asp Ser Ser Ala Tyr Glu Asn Val
        115                 120                 125

Lys Phe Ile Val Asn Val Arg Asp Ile Cys Asn Glu Phe Pro Val Val
    130                 135                 140

Phe Ser Gly Leu Phe Ser Ser His Leu Cys Ala Asp Phe Ala Ala Cys
145                 150                 155                 160

Val Pro Gln Glu Asp Arg Leu Tyr Leu Val Gly Asn Val Cys Ile Leu
                165                 170                 175

Arg Thr Gln Leu Leu Gln Gln Leu Tyr Thr Ser Lys Ala Val Ser Asp
            180                 185                 190

Glu Ala Val Leu Thr Gln Asp Ser Asp Glu Glu Pro Phe Val Gly Glu
        195                 200                 205

Leu Ser Ser Ser Gln Gly Gln Arg Gly His Thr Ser Met Lys Ala Val
    210                 215                 220

Tyr Val Glu Pro Ala Ala Ala Ala Ala Ala Ala Ile Ser Asp Asp
225                 230                 235                 240

Gln Ile Asp Ile Ala Glu Val Glu Gln Tyr Gly Pro Gln Glu Asn Val
                245                 250                 255

His Met Phe Val Asp Ser Asp Ser Thr Tyr Cys Ser Ser Thr Val Phe
            260                 265                 270

Leu Asp Thr Met Pro Glu Ser Pro Ala Leu Ser Leu Gln Asp Phe Arg
        275                 280                 285
```

```
Gly Glu Pro Glu Val Asn Pro Leu Tyr Arg Ala Asp Pro Val Asp Leu
        290                 295                 300
Glu Phe Ser Val Asp Gln Val Asp Ser Val Asp Gln Glu Gly Pro Met
305                 310                 315                 320
Asp Gln Gln Asp Pro Glu Asn Pro Val Ala Pro Leu Asp Gln Ala Gly
                325                 330                 335
Leu Met Asp Pro Val Asp Pro Glu Asp Ser Val Asp Leu Gly Ala Ala
            340                 345                 350
Gly Ala Ser Ala Gln Pro Leu Gln Pro Ser Ser Pro Val Ala Tyr Asp
        355                 360                 365
Ile Ile Ser Gln Glu Leu Glu Leu Met Lys Lys Leu Lys Glu Gln Leu
    370                 375                 380
Glu Glu Arg Thr Trp Leu Leu His Asp Ala Ile Gln Asn Gln Gln Asn
385                 390                 395                 400
Ala Leu Glu Leu Met Met Asp His Leu Gln Lys Gln Pro Asn Thr Leu
                405                 410                 415
Arg His Val Val Ile Pro Asp Leu Gln Ser Ser Glu Ala Val Pro Lys
            420                 425                 430
Lys Gln Gln Lys Gln His Ala Gly Gln Val Lys Arg Pro Leu Pro His
        435                 440                 445
Pro Lys Asp Val Lys Cys Phe Cys Gly Leu Ser Leu Ser Asn Ser Leu
    450                 455                 460
Lys Asn Thr Gly Glu Leu Gln Glu Pro Cys Val Ala Phe Asn Gln Gln
465                 470                 475                 480
Gln Leu Val Gln Gln Glu His Leu Lys Glu Gln Arg Gln Leu
                485                 490                 495
Arg Glu Gln Leu Gln Gln Leu Arg Glu Gln Arg Lys Val Gln Lys Gln
            500                 505                 510
Lys Lys Met Gln Glu Lys Lys Leu Gln Glu Gln Lys Met Gln Glu
        515                 520                 525
Lys Lys Lys Leu Gln Glu Gln Arg Arg Gln Lys Lys Lys Leu Gln
    530                 535                 540
Glu Arg Lys Lys Trp Gln Gly Gln Met Leu Gln Lys Glu Pro Glu Glu
545                 550                 555                 560
Glu Gln Gln Lys Gln Gln Leu Gln Glu Gln Pro Leu Lys His Asn Val
                565                 570                 575
Ile Val Gly Asn Glu Arg Val Gln Ile Cys Leu Gln Asn Pro Arg Asp
            580                 585                 590
Val Ser Val Pro Leu Cys Asn His Pro Val Arg Phe Leu Gln Ala Gln
        595                 600                 605
Pro Ile Val Pro Val Gln Arg Ala Ala Glu Gln Pro Ser Gly Phe
    610                 615                 620
Tyr Gln Asp Glu Asn Cys Gly Gln Gln Glu Asp Glu Ser Gln Arg
625                 630                 635

<210> SEQ ID NO 23
<211> LENGTH: 773
<212> TYPE: PRT
<213> ORGANISM: Homo sapiens

<400> SEQUENCE: 23

Met Lys Met Arg Gly Glu Lys Arg Arg Asp Lys Val Asn Pro Lys Ser
1               5                   10                  15
Ser Gln Arg Lys Leu Asn Trp Ile Pro Ser Phe Pro Thr Tyr Asp Tyr
            20                  25                  30
```

```
Phe Asn Gln Val Thr Leu Gln Leu Leu Asp Gly Phe Met Ile Thr Leu
            35                  40                  45

Ser Thr Asp Gly Val Ile Ile Cys Val Ala Glu Asn Ile Ser Ser Leu
 50                  55                  60

Leu Gly His Leu Pro Ala Glu Ile Val Gly Lys Lys Leu Leu Ser Leu
 65                  70                  75                  80

Leu Pro Asp Glu Glu Lys Asp Glu Val Tyr Gln Lys Ile Ile Leu Lys
                    85                  90                  95

Phe Pro Leu Leu Asn Ser Glu Thr His Ile Glu Phe Cys Cys His Leu
                100                 105                 110

Lys Arg Gly Asn Val Glu His Gly Asp Ser Ser Ala Tyr Glu Asn Val
                115                 120                 125

Lys Phe Ile Val Asn Val Arg Asp Ile Cys Asn Glu Phe Pro Val Val
            130                 135                 140

Phe Ser Gly Leu Phe Ser Ser His Leu Cys Ala Asp Phe Ala Ala Cys
145                 150                 155                 160

Val Pro Gln Glu Asp Arg Leu Tyr Leu Val Gly Asn Val Cys Ile Leu
                165                 170                 175

Arg Thr Gln Leu Leu Gln Leu Tyr Thr Ser Lys Ala Val Ser Asp
                180                 185                 190

Glu Ala Val Leu Thr Gln Asp Ser Asp Glu Pro Phe Val Gly Glu
            195                 200                 205

Leu Ser Ser Ser Gln Gly Gln Arg Gly His Thr Ser Met Lys Ala Val
            210                 215                 220

Tyr Val Glu Pro Ala Ala Ala Ala Ala Ala Ala Ile Ser Asp Asp
225                 230                 235                 240

Gln Ile Asp Ile Ala Glu Val Glu Gln Tyr Gly Pro Gln Glu Asn Val
                245                 250                 255

His Met Phe Val Asp Ser Asp Ser Thr Tyr Cys Ser Ser Thr Val Phe
                260                 265                 270

Leu Asp Thr Met Pro Glu Ser Pro Ala Leu Ser Leu Gln Asp Phe Arg
            275                 280                 285

Gly Glu Pro Glu Val Asn Pro Leu Tyr Arg Ala Asp Pro Val Asp Leu
            290                 295                 300

Glu Phe Ser Val Asp Gln Val Asp Ser Val Asp Gln Glu Gly Pro Met
305                 310                 315                 320

Asp Gln Gln Asp Pro Glu Asn Pro Val Ala Pro Leu Asp Gln Ala Gly
                325                 330                 335

Leu Met Asp Pro Val Asp Pro Glu Asp Ser Val Asp Leu Gly Ala Ala
            340                 345                 350

Gly Ala Ser Ala Gln Pro Leu Gln Pro Ser Ser Pro Val Ala Tyr Asp
            355                 360                 365

Ile Ile Ser Gln Glu Leu Glu Leu Met Lys Lys Leu Lys Glu Gln Leu
370                 375                 380

Glu Glu Arg Thr Trp Leu Leu His Asp Ala Ile Gln Asn Gln Gln Asn
385                 390                 395                 400

Ala Leu Glu Leu Met Met Asp His Leu Gln Lys Gln Pro Asn Thr Leu
                405                 410                 415

Arg His Val Val Ile Pro Asp Leu Gln Ser Ser Glu Ala Val Pro Lys
            420                 425                 430

Lys Gln Gln Lys Gln His Ala Gly Gln Val Lys Arg Pro Leu Pro His
            435                 440                 445
```

```
Pro Lys Asp Val Lys Cys Phe Cys Gly Leu Ser Leu Ser Asn Ser Leu
450                 455                 460
Lys Asn Thr Gly Glu Leu Gln Glu Pro Cys Val Ala Phe Asn Gln Gln
465                 470                 475                 480
Gln Leu Val Gln Gln Gln His Leu Lys Glu Gln Gln Arg Gln Leu
            485                 490                 495
Arg Glu Gln Leu Gln Gln Leu Arg Glu Gln Arg Lys Val Gln Lys Gln
                500                 505                 510
Lys Lys Met Gln Glu Lys Lys Leu Gln Glu Gln Lys Met Gln Glu
        515                 520                 525
Lys Lys Lys Leu Gln Glu Gln Arg Arg Gln Lys Lys Lys Leu Gln
530                 535                 540
Glu Arg Lys Lys Trp Gln Gly Gln Met Leu Gln Lys Glu Pro Glu Glu
545                 550                 555                 560
Glu Gln Gln Lys Gln Gln Leu Gln Gly Gln Pro Leu Lys His Asn Val
                565                 570                 575
Ile Val Gly Asn Glu Arg Val Gln Ile Cys Leu Gln Asn Pro Arg Asp
            580                 585                 590
Val Ser Val Pro Leu Cys Asn His Pro Val Arg Phe Leu Gln Ala Gln
            595                 600                 605
Pro Ile Val Pro Val Gln Arg Ala Ala Glu Gln Gln Pro Ser Gly Phe
610                 615                 620
Tyr Gln Asp Glu Asn Cys Gly Gln Gln Glu Asp Glu Ser Gln Ser Phe
625                 630                 635                 640
Tyr Pro Glu Ala Tyr Gln Gly Pro Pro Val Asn Gln Leu Pro Leu Ile
                645                 650                 655
Asp Thr Ser Asn Ser Glu Ala Ile Ser Ser Ser Ile Pro Gln Phe
            660                 665                 670
Pro Ile Thr Ser Asp Ser Thr Ile Ser Thr Leu Glu Thr Pro Gln Asp
            675                 680                 685
Tyr Ile Arg Leu Trp Gln Glu Leu Ser Asp Ser Leu Gly Pro Val Val
690                 695                 700
Gln Val Asn Thr Trp Ser Cys Asp Glu Gln Gly Thr Leu His Gly Gln
705                 710                 715                 720
Pro Thr Tyr His Gln Val Gln Val Ser Glu Val Gly Val Glu Gly Pro
                725                 730                 735
Pro Asp Pro Gln Ala Phe Gln Gly Pro Ala Ala Tyr Gln Pro Asp Gln
            740                 745                 750
Met Arg Ser Ala Glu Gln Thr Arg Leu Met Pro Ala Glu Gln Arg Asp
            755                 760                 765
Ser Asn Lys Pro Cys
    770

<210> SEQ ID NO 24
<211> LENGTH: 9
<212> TYPE: PRT
<213> ORGANISM: Human immunodeficiency virus type 1

<400> SEQUENCE: 24

Ile Leu Lys Glu Pro Val His Gly Val
1               5
```

```
<210> SEQ ID NO 25
<211> LENGTH: 20
<212> TYPE: PRT
<213> ORGANISM: Human immunodeficiency virus type 1

<400> SEQUENCE: 25

Asp Glu Ser Phe Arg Lys Tyr Thr Ala Phe Thr Ile Pro Ser Met Asn
1               5                   10                  15

Asn Glu Thr Pro
            20

<210> SEQ ID NO 26
<211> LENGTH: 3250
<212> TYPE: DNA
<213> ORGANISM: Homo sapiens

<400> SEQUENCE: 26
agttccagag acagtagtta tctcgggccc caacatcgcg aggtctaggg aaaaatgcta      60
ccactcctcc ccctacttc cgctgccacg ctgcctccat gctgcctcc cctctctgcc      120 acgcccccac cacgcgcttt gcactctggg gcccacgcac ttccctgaag agtctagaag    180
ctgctcctca tttccagact ttccgggcgc ccaccaggct cccgggctct caccggagac    240
cacagggagg agcttcaagg taccccaagt ccctgcggcc tccagcagtg aagagttcca    300
caagggagtc ttcctacgtc actgaataat gaatgaagat gagaggggaa aagagaagag    360
acaaagtcaa tccaaaaagc tctcaaagga aattaaactg gattccatca tttcctacct    420
atgattactt caaccaagtg acgctacagt tattagatgg ctttatgatt acactgagca    480
cagatggagt gatcatttgt gtggctgaaa acatctcttc tcttcttgga catttaccag    540
ctgagattgt gggcaaaaaa ttattaagcc ttctgcctga tgaagagaaa gatgaagtct    600
accaaaagat tattctcaaa tttccttac taaaactcaga aacacatatt gaattttgct    660
gtcatttaaa aagaggaaat gtcgaacatg gtgatagttc tgcttacgaa aacgtgaaat    720
ttattgtgaa tgtaagagat atttgtaatg agtttcctgt ggtctttagt ggcttgtttt    780
ccagccacct ctgtgctgac tttgctgcat gtgttcctca ggaggatcgg ctttatcttg    840
tgggaaatgt ttgcattctc aggactcagc tcctgcagca actttacact tcaaaggcag    900
tcagtgatga agctgtactt acacaagatt cagatgagga ccttttgtg ggagagctca    960 gtagctctca aggtcaaaga ggacacacta gcatgaaagc cgtgtacgtt gaacccgctg    1020
ctgctgctgc tgctgctgct atctcagacg accaaattga tattgcagag gttgagcagt    1080
atggaccaca agaaaacgtt cacatgtttg tagattctga ttcaacttat tgctccagta    1140
cagttttcct ggatactatg cctgaatctc cagccttatc cttgcaagac tttcgaggtg    1200
agcctgaggt gaatccattg tacagggcag acccagtgga cctggagttc tcggtggatc    1260
aggtggactc agtggaccag gagggcccaa tggaccagca ggaccagag aacccagttg    1320 ccccgttgga ccaggcaggc ctgatggatc cagtggatcc agaggactca gtggacctgg    1380
gggctgctgg cgcaagtgct cagccattac agccatcatc accagttgca tatgacatca    1440
ttagccagga actggaactg atgaagaagt tgaaggagca gctagaagag aggacttggt    1500
tgctgcatga tgccatccaa aaccagcaga atgcattgga attgatgatg gatcaccttc    1560
agaagcagcc aaaacacatta cgccacgttt tcattcctga tctccaatct tcggaggcag    1620
tgcccaagaa acaacagaaa caacacgctg ggcaagtgaa gcggcctctc ccacatccca    1680
```

| | |
|---|---|
| aggacgtcaa gtgtttctgt ggtttatctt tatccaactc tctcaaaaac actggggagc | 1740 |
| ttcaggagcc ttgtgttgcc ttcaaccagc agcaactggt gcagcaagaa caacacctga | 1800 |
| aggagcagca gcggcagctg cgggagcagc tgcaacagct gagagagcaa aggaaggtgc | 1860 |
| agaagcagaa gaagatgcag gagaagaaga agctgcagga gcagaaaatg caggagaaga | 1920 |
| agaagctgca ggagcagagg cggcaaaaga agaagaagct acaggagcgg aagaagtggc | 1980 |
| aggggcagat gctacagaaa gagccagagg aggagcagca gaagcagcag ctgcaagagc | 2040 |
| agccactgaa gcataatgtc atcgtgggga atgagagggt gcagatatgc ctgcaaaacc | 2100 |
| cacgtgacgt atctgtgccc ctctgcaatc accctgttag attttacag gcccaaccca | 2160 |
| ttgttcctgt ccagagagca gctgaacaac agccctctgg cttctatcaa gatgaaaact | 2220 |
| gtgggcaaca ggaagatgag agtcaaagtt tttatcctga ggcgtatcaa gggccccccg | 2280 |
| tgaaccagct gccattgata gatacctcaa actctgaggc aatttcttct tccagcattc | 2340 |
| ctcagtttcc cataacttca gactcaacca taagcaccct ggagacccca caggattaca | 2400 |
| tccggctttg gcaagagttg tctgattcac tcggtcctgt tgtccaagtg aacacttggt | 2460 |
| cttgcgatga gcagggcacc ctgcacggcc aacccaccta ccatcaggtg caagtttctg | 2520 |
| aggtaggagt cgagggacct cctgatccac aggcttttcca aggccctgct gcataccagc | 2580 |
| cagaccagat gagatctgcg gagcagacca gattgatgcc tgcagagcaa cgtgactcaa | 2640 |
| ataagccgtg ctaacagtac tttcatgacc agtgatgagg ggaaatgggg ggaggggca | 2700 |
| ggccaatgag gtctgcatgg ccaggggacc ttcaaggtgc gtaaagtccc ttggggtagg | 2760 |
| gtttagtggg tagagactta tttgtttcct gataggttat gtttgtaatt gtttgttaag | 2820 |
| cacagcctgt ttcttggaag ttatgctgta gaggcagcct gtgatccgta gtatgctagg | 2880 |
| gtgtgacagc agccagccac agctggatct gatgtcttgt ctgccccgcc cagctttgca | 2940 |
| tatccatgtt ctaccacagg aaggtggcct gccaagagtc tgctcaaagt tttcaacata | 3000 |
| aagaataaag aaaaaaaaat gccaaagtgc ttttcaatct agtaaatcta gagggttgtt | 3060 |
| ttgtcttagc cacaagaatt ccgaggtctt gaccctgatg atcaacctgc ctcccctcca | 3120 |
| tagtcttgtt ggagaagccc agagagaatg ggactccaac taagggaacc tgaaatcaac | 3180 |
| tcaatggagg cacttcagag ctaaaataat tatggcttcc ttgcttaata aacatttcg | 3240 |
| ttcactgcaa | 3250 |

<210> SEQ ID NO 27
<211> LENGTH: 9
<212> TYPE: PRT
<213> ORGANISM: Homo sapiens

<400> SEQUENCE: 27

Tyr Phe Asn Gln Val Thr Leu Gln Leu
1               5

<210> SEQ ID NO 28
<211> LENGTH: 21
<212> TYPE: PRT
<213> ORGANISM: Homo sapiens

<400> SEQUENCE: 28

Phe Asn Asn Phe Thr Val Ser Phe Trp Leu Arg Val Pro Lys Val Ser
1               5                   10                  15

Ala Ser His Leu Glu
            20

IMMUNOGENIC PEPTIDES

This application is a U.S. National-Stage Application, claiming priority benefit of PCT/GB2009/002332, filed Oct. 1, 2009, which claims benefit of priority from GB Application No. 0818080.4, filed on Oct. 2, 2008, both of which are incorporated herein by reference in their entirety.

FIELD OF THE INVENTION

The present invention relates to immunogenic peptides and their various applications. In particular the invention relates to immunogenic peptides derived from the PASD1 protein and their use in therapeutic, diagnostic and prognostic methods.

BACKGROUND OF THE INVENTION

Tumour-associated antigens (TAAs), recognized by the immune system of a cancer patient, may represent important immunotherapeutic targets. Evidence in support of this has been provided by autologous bone marrow transplantation and donor lymphocyte infusion studies, demonstrating that donor cells can recognize and respond to TAAs in a variety of haematological malignancies such as multiple myeloma and myeloid leukaemia (Bellucci et al 2004, Porter et al 2006, Atanackovic et al 2007). Furthermore, vaccination studies have reported an increased immune response to TAAs (Rezvani et al 2007, Schmitt et al 2008). It is also of note that the immune response signature has been identified as being of importance in predicting survival in diffuse large B-cell lymphoma (DLBCL) and follicular lymphoma (FL) (Dave et al 2004, Monti et al 2005).

TAAs that are of current interest for improving treatment regimens are the cancer testis antigens (CTAs). Their restricted normal tissue distribution but widespread expression in tumours makes them attractive immunotherapeutic targets, while minimizing potential problems with autoimmunity (Scanlan et al 2004, Simpson et al 2005, Suri 2006). Initially, studies of CTA expression focussed on solid tumours (Simpson et al 2005), but there are increasing reports of CTAs being expressed in haematological malignancies such as multiple myeloma (Pellat-Deceunynck et al 2000, Chiriva-Internati et al 2001, Lim et al 2001, Sugita et al 2004, van Rhee et al 2005, Goodyear et al 2005, Jungbluth et al 2005) and myeloid malignancies (Adams et al 2002, Zhang et al 2003, Andrade et al 2008, Tinguely et al 2008). Indeed, a gene expression profiling study reported transcripts of multiple CTAs in myeloma tumour cells (Condomines et al 2007). Other studies have also reported the presence of cytotoxic T cells (CTLs), considered to be the major effector cells in cellular immunity, to CTAs such as NY-ESO-1 and Sp17 in the peripheral blood of multiple myeloma patients, thereby suggesting the presence of spontaneous immunity to these CTAs (van Rhee et al 2005, Goodyear et al 2005). There is also accumulating evidence for a major role for CD4+ T-helper ($T_H$) cells not only in the regulation and maintenance of the CTL and humoural responses but also in the ability of the $T_H$ themselves to control tumour cell growth (Oestrand-Rosenberg et al 2005), Goodyear et al 2008). A subsequent investigation has shown that this immunity can be boosted through vaccination with antigens such as NY-ESO-1 (Baumgaertner et al 2006, Odunzi et al 2007) and clinical trials are ongoing using CTAs as vaccine targets (Szmania et al 2006, Odunzi et al 2007).

The present inventors previously used the SEREX technique, which exploits the circulating antibodies present in the serum of patients, to identify the PAS (Per ARNT Sim) domain containing 1 (PASD1) protein or CT63, encoded by a gene at Xq28, as a lymphoma-associated antigen and candidate CTA (Liggins et al 2004a, Liggins et al 2004b). Two splice variants were identified, PASD1a (639 amino acids) and PASD1b (773 amino acids). The first 638 amino acids are common to both proteins (Liggins et al 2004a). This work is described by International Patent Application Publication No. WO 03/082916, which is incorporated by reference in its entirety.

The production of monoclonal antibodies to PASD1 allowed confirmation of this molecule as a novel CTA with a highly restricted expression pattern in normal tissues and more specifically as a CT-X antigen expressed in a range of haematological malignancies (Cooper et al 2006, Sahota et al 2006).

SUMMARY OF THE INVENTION

The present invention relates to immunogenic peptides derived from PASD1. The invention thus provides an immunogenic peptide of from about 9 to about 25 amino acids in length comprising at least 9 consecutive amino acids of the amino acid sequence of any of SEQ ID Nos. 1 to 10 or 27.

In certain preferred embodiments, the immunogenic peptide is capable of stimulating a T-cell response. Preferably, the peptide is capable of producing a cytotoxic T lymphocyte (CTL) response.

In these embodiments, the immunogenic peptide may be between 9 and 12 and in particular either 9 or 10 amino acids in length. The peptide may comprise, consist essentially of, or consist of the amino acid sequence of any one of SEQ ID Nos. 1 to 5. Preferably, the peptide comprises, consists essentially of, or consists of the amino acid sequence of any one of SEQ ID Nos. 1, 2 or 5.

In other embodiments, the peptide is capable of producing a T helper ($T_H$) cell response.

In these embodiments, the peptide may be of from about 18 to about 25 amino acids in length. Preferably, the peptide is 20 amino acids in length. The peptide may comprise, consist essentially of, or consist of the amino acid sequence of any one of SEQ ID Nos. 6 to 10. Preferably, the peptide comprises, consists essentially of, or consists of the amino acid sequence of any one of SEQ ID Nos. 6, 7 or 10.

In certain embodiments, the peptide may be capable of producing both a CTL and a $T_H$ cell response.

In other embodiments, the present invention relates to a nucleic acid encoding an immunogenic peptide of the invention as described herein. Preferably the nucleic acid comprises, consists essentially of, or consists of the nucleotide sequence of any one of SEQ ID Nos. 11 to 20.

The present invention also provides an expression vector comprising a nucleic acid described herein. A host cell or organism transformed or transfected with such an expression vector is also provided.

A transgenic non-human organism comprising a transgene encoding an immunogenic peptide of the present invention is also provided.

A vaccine comprising an immunogenic peptide of the invention, a nucleic acid of the invention, an expression vector of the invention or a host cell of the invention is also provided.

The present invention also relates to an isolated T-cell specific for an immunogenic peptide as described herein. Furthermore, the present invention relates to an isolated T-cell produced by stimulating peripheral blood mononuclear cells (PBMCs) with an immunogenic peptide of the invention as described herein.

The present invention also relates to the T-cell receptor (TCR) sequence specific for an immunogenic peptide of the invention as described herein.

In certain embodiments, the isolated T-cell is a cytotoxic T lymphocyte (CTL) specific for an immunogenic peptide of the invention as described herein.

In other embodiments, the isolated T-cell is a T helper ($T_H$) cell specific for an immunogenic peptide of the invention as described herein.

The present invention also relates to pharmaceutical compositions comprising an immunogenic peptide of the invention, a nucleic acid, an expression vector or a host cell described herein and a pharmaceutically acceptable carrier or excipient.

The pharmaceutical compositions of the invention may comprise an immunogenic peptide capable of stimulating a CTL response and an immunogenic peptide capable of stimulating a $T_H$ response for simultaneous, sequential or separate administration.

The pharmaceutical compositions of the invention may comprise two or more of an immunogenic peptide, a nucleic acid, an expression vector or a host cell as described herein for simultaneous, sequential or separate administration.

In a further aspect, the present invention relates to an immunogenic peptide, a nucleic acid, an expression vector, a host cell, a vaccine, an isolated T-cell, or a pharmaceutical composition as described herein for use in therapy.

Preferably, the immunogenic peptide, nucleic acid, expression vector, host cell, vaccine, isolated T-cell, or pharmaceutical composition described herein is for use in the treatment of cancer.

The present invention also relates to the use of the immunogenic peptide, nucleic acid, expression vector, host cell, vaccine, isolated T-cell, or pharmaceutical composition described herein in the manufacture of a medicament for the treatment of cancer.

In certain embodiments, the cancer is either a haematologically derived malignancy selected from multiple myeloma, mantle cell lymphoma, Hodgkin's lymphoma, T-cell lymphomas, follicular lymphoma (FL), Burkitt's lymphoma, T-cell rich B cell lymphoma, diffuse large B-cell lymphoma (DLBCL) and acute and chronic myeloid leukaemia, or a non-haematologically derived malignancy selected from brain, melanoma, lung, breast, gastric, kidney, prostate, testicular, ovarian, uterine, colorectal and liver cancers and adenocarcinoma of the colon.

In yet another aspect, the present invention relates to a method of treatment of cancer, comprising administering a therapeutically effective amount of an immunogenic peptide, a nucleic acid, an expression vector, a host cell, a vaccine, an isolated T-cell, or a pharmaceutical composition as described herein to a patient in need thereof.

The present invention further relates to a method of treatment of cancer, comprising the steps of:
 (a) isolating a cell population containing or capable of producing CTLs and/or $T_H$ cells from a subject;
 (b) treating the cell population with an immunogenic peptide(s) described herein optionally together with a proliferative agent;
 (c) screening the cell population for CTLs and/or $T_H$ cells with specificity to an immunogenic peptide(s) described herein;
 (d) administering the cell population to a patient suffering from cancer.

In certain embodiments, the CTLs and/or $T_H$ cells with specificity to an immunogenic peptide(s) described herein are isolated from the cell population and administered to a patient suffering from cancer.

In a further aspect, the present invention relates to a method of treatment of cancer, comprising the steps of:
 (a) isolating a cell population containing or capable of producing CTLs and/or $T_H$ cells from a subject;
 (b) treating the cell population with an immunogenic peptide(s) described herein optionally together with a proliferative agent;
 (c) screening the cell population for CTLs and/or $T_H$ cells with specificity to an immunogenic peptide(s) described herein;
 (d) cloning the T-cell receptor (TCR) genes from the CTLs and/or $T_H$ with specificity to the immunogenic peptide(s) described herein;
 (e) transducing the TCR gene cloned in step (c) into either:
  i. cells from the patient;
  ii. cells from a donor; or
  iii. eukaryotic or prokaryotic cells for the generation of cell surface or secreted monoclonal TCRs (mTCRs); and
 (f) administering the cells or mTCRs from step (e) to a patient suffering from cancer.

In certain embodiments the subject from which the cell population is isolated is the patient in need of treatment (i.e. suffering from cancer). Alternatively, the cell population may be isolated from a normal subject or the mTCRs themselves may be administered.

Preferably the cancer is either a haematologically derived malignancy selected from multiple myeloma, mantle cell lymphoma, Hodgkin's lymphoma, T-cell lymphomas, follicular lymphoma, Burkitt's lymphoma, T-cell rich B cell lymphoma, diffuse large B-cell lymphoma (DLBCL) and acute and chronic myeloid leukaemia, or a non-haematologically derived malignancy selected from brain, melanoma, lung, breast, gastric, kidney, prostate, testicular, ovarian, uterine, colorectal and liver cancers and adenocarcinoma of the colon.

In another aspect of the present invention, a method of diagnosing cancer is provided. The method comprises the steps of:
 (a) obtaining a blood sample from a patient;
 (b) screening for the presence of CTLs and/or $T_H$ cells specific for an immunogenic peptide described herein, wherein the presence of such cells indicates a positive diagnosis of cancer.

In a further aspect, the present invention relates to a method of predicting a clinical outcome for a patient with a cancer, comprising the steps of:
 (a) isolating peripheral blood mononuclear cells (PBMCs) from a patient with a cancer;
 (b) screening said PBMCs for recognition of an immunogenic peptide described herein;
 (c) assigning a predicted positive clinical outcome to the patient where the PBMCs recognise the immunogenic peptide described herein or a predicted negative clinical outcome to the patient where the PBMCs do not recognise the immunogenic peptide described herein.

Preferably the cancer is either a haematologically derived malignancy selected from multiple myeloma, mantle cell lymphoma, Hodgkin's lymphoma, T-cell lymphomas, follicular lymphoma, Burkitt's lymphoma, T-cell rich B cell lymphoma, diffuse large B-cell lymphoma (DLBCL) or acute and chronic myeloid leukaemia, or a non-haematologically derived malignancy selected from brain, melanoma, lung, breast, gastric, kidney, prostate, testicular, ovarian, uterine, colorectal and liver cancers and adenocarcinoma of the colon.

DESCRIPTION OF THE DRAWINGS

The present invention will be further understood by reference to the drawings.

The positions of the PASD1 peptides are shown as horizontal lines: 1=PASD1(1); 2=PASD1(2); 3=PASD1(3); 4=PASD1(4); 5=PASD1(5); 6=PASD1(6); 7=PASD1(7); 8=PASD1(8); 9=PASD1(9) and 10=PASD1(10).

FIG. 2. γ-IFN responses of patients with de novo DLBCL (12) and transformed DLBCL (37) to PASD1 peptides.

a) PBMCs obtained from patients 12 and 48 at time of diagnosis and after one year from start of treatment were maintained in short term culture. A significant γ-IFN response to peptides PASD1(1), PASD1(2) and PASD1(5) was observed in cells from both patients obtained at time of diagnosis and after one year from the start of treatment (p<0.05). This suggests the presence of memory T cells. No significant response was detected in cultures stimulated by the HIV peptide or containing medium only.

b) CTL cell lines generated after 6 weeks of culture were either enriched for CD8-positive cells using anti-CD8 antibody coated magnetic beads or incubated with an anti-HLA-A2*0201 monoclonal antibody (BB7.2). A significant γ-IFN response was observed only in the culture containing the CD8-positive cells (p<0.05). No significant responses were detected in the control cultures or the irrelevant peptides. The results are the mean+/−SD and were obtained from triplicate ELISPOT cultures.

FIG. 3. Cytolytic activity of the PASD1-specific CTL cell lines derived from patients with DLBCL.

The functional activity of CTL cell lines obtained from patients 1 (a-c), 12 (d-f) (de novo DLBCL) and patient 48 (g-i) (T-cell rich DLBCL) were studied in a conventional $^{51}$Cr release assay on a range of haematological cell lines. Significant dose dependent lysis of the HLA-A*0201-positive PASD1-positive Thiel (myeloma) cell line was observed by cells from all three patients. In contrast no significant lysis was observed of the SUDHL-6 (DLBCL; HLA-A*0201-positive but PASD1-negative) or the OCI-Ly3 (DLBCL) and KM-H2 (HL; HLA-A*0201-negative but PASD1-positive) cell lines. Results are the mean+/−SD from triplicate cultures.

Figure 4A:
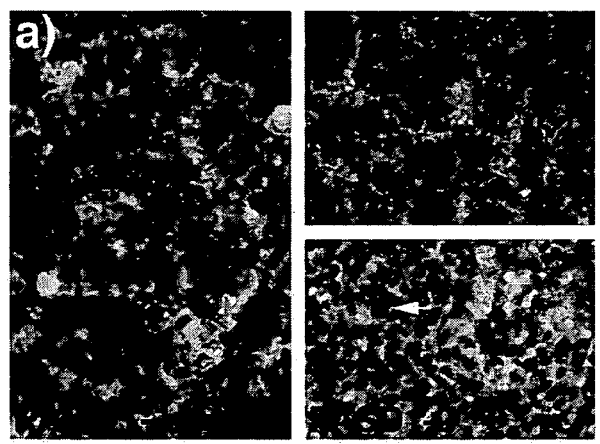
Figure 4B:
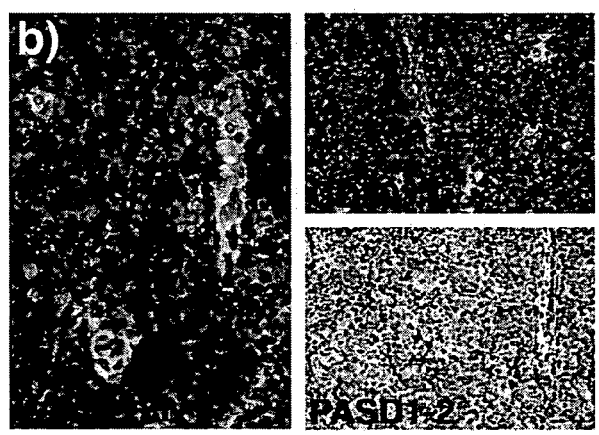
Figure 4C:
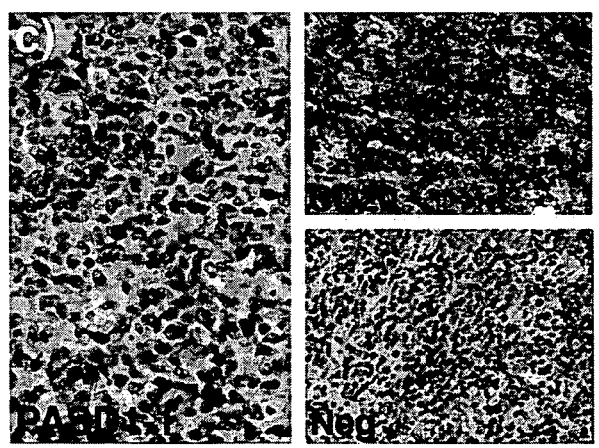

FIG. 4. Immunoperoxidase labelling studies of biopsy sections from patients with de novo DLBCL.

a) Antibody PASD1-1 strongly stains the cytoplasm of tumour cells from HLA-A*0201-positive Patient 4 whose PBMCs exhibited a significant γ-IFN response to PASD1 peptides. Antibody PASD1-2 stained a subpopulation of nuclei (arrowed) as well as cytoplasm of the tumour cells.

b and c) show the immunolabelling results obtained from two HLA-A*0201-negative patients in whom no PASD1 T-cell response was detected. Whereas the tumour cells from Patient 27 were labelled strongly with antibody PASD1-1 b), no labelling was detected with antibody PASD1-2. Neither of the antibodies PASD1-1 c) or PASD1-2 (not shown) stained the tumour cells of Patient 17.

Figure 5A:
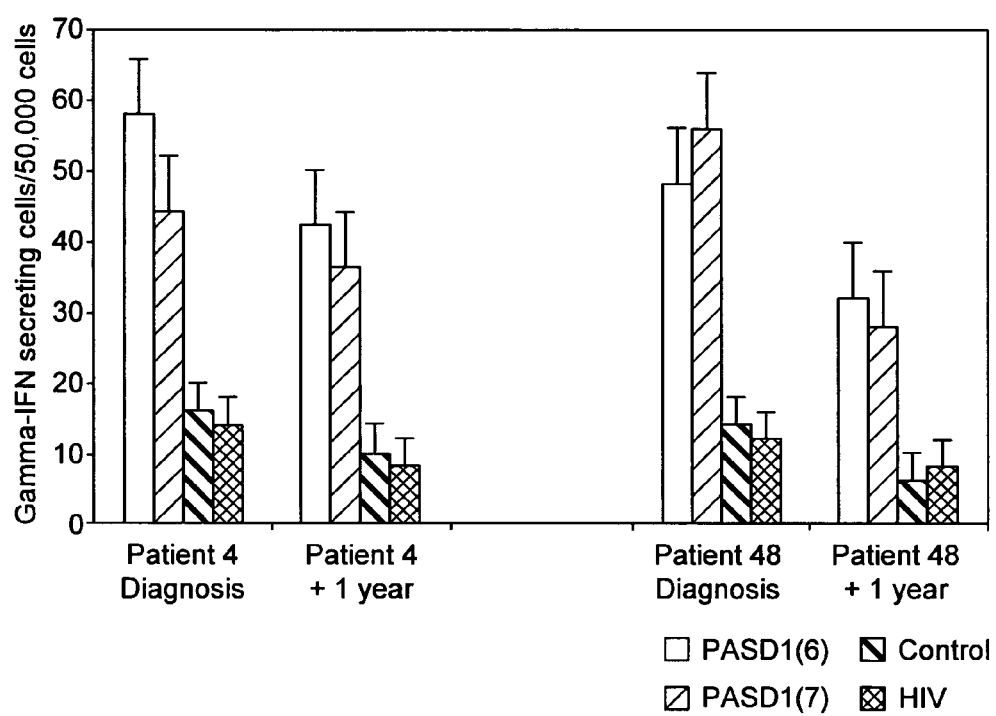
Figure 5B:
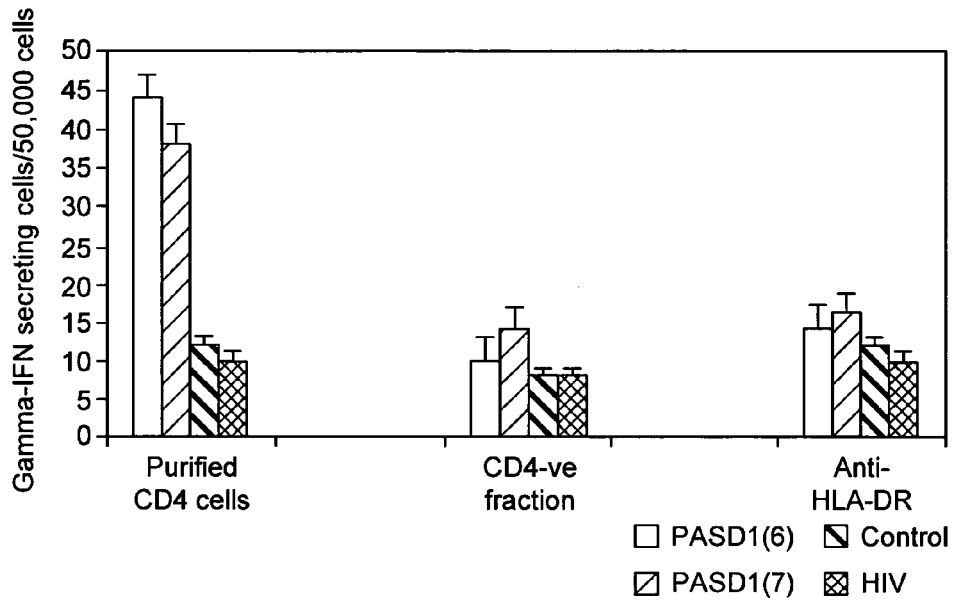
Figure 5C:
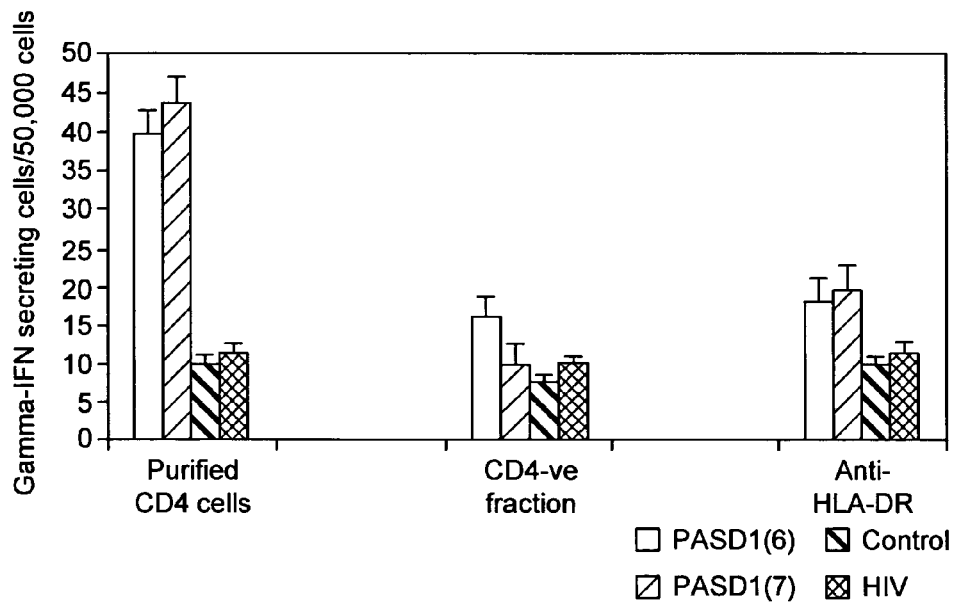

FIG. 5. The $T_H$ γ-IFN responses of patients with DLBCL to PASD1 peptides.

a) PBMCs from Patients 4 (de novo DLBCL) and 48 (T-cell rich DLBCL) were obtained at time of diagnosis and after one year from start of treatment were maintained in short term culture. A significant γ-IFN response to peptides PASD1(6) and PASD1(7) was observed in cells from both patients obtained at time of diagnosis and after one year from the start of treatment (p<0.05). This suggests the presence of memory T cells. No significant response was detected in cultures stimulated by the HIV peptide or containing medium only.

b and c) $T_H$ rich cell lines generated after 6 weeks of culture were either enriched for CD4-positive cells using anti-CD4 antibody coated magnetic beads or incubated with an anti-HLA-DR monoclonal antibody (WR18). A significant γ-IFN response was observed only in the culture containing the CD4-positive cells (p<0.05). Abrogation of the γ-IFN response was observed following the addition of anti-HLA-DR. No significant responses were detected in the control cultures or the irrelevant peptides. The results are the mean+/−SD and were obtained from triplicate ELISPOT cultures.

Figure 6A:
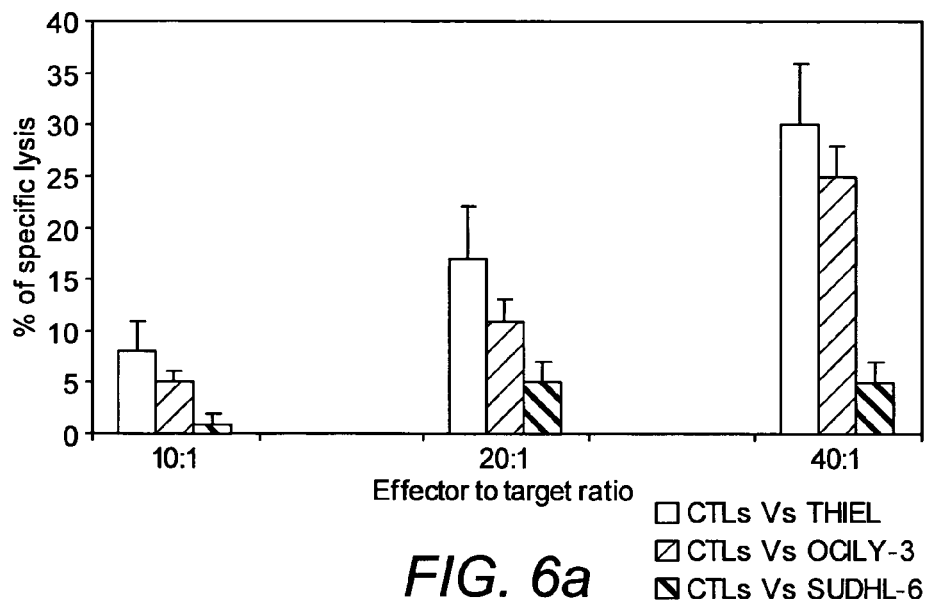
Figure 6B:
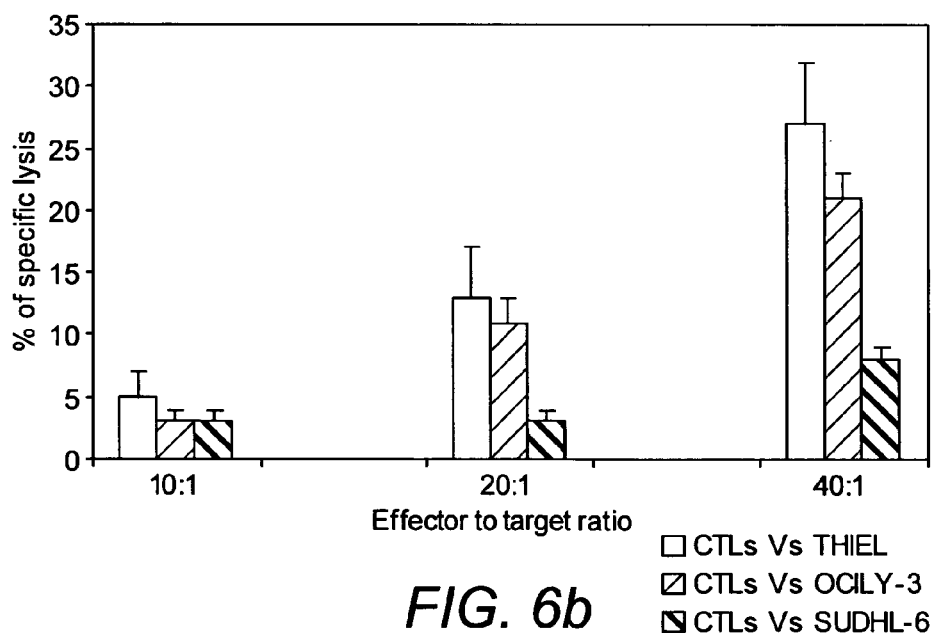

FIG. 6. Cytolytic activity of the PASD1-specific $T_H$ cell lines derived from Patient 1 with DLBCL.

a and b) The functional activity of $T_H$ cell lines specific for PASD1(6) and PASD1(7) were studied in a conventional $^{51}$Cr release assay on a range of haematological cell lines. Significant dose dependent lysis of the PASD1-positive Thiel (myeloma) and OCI-Ly3 cell lines. In contrast no significant lysis was observed of the PASD1-negative SUDHL-6 (DLBCL) cell line. Results are the mean+/−SD from triplicate cultures.

Figure 7:
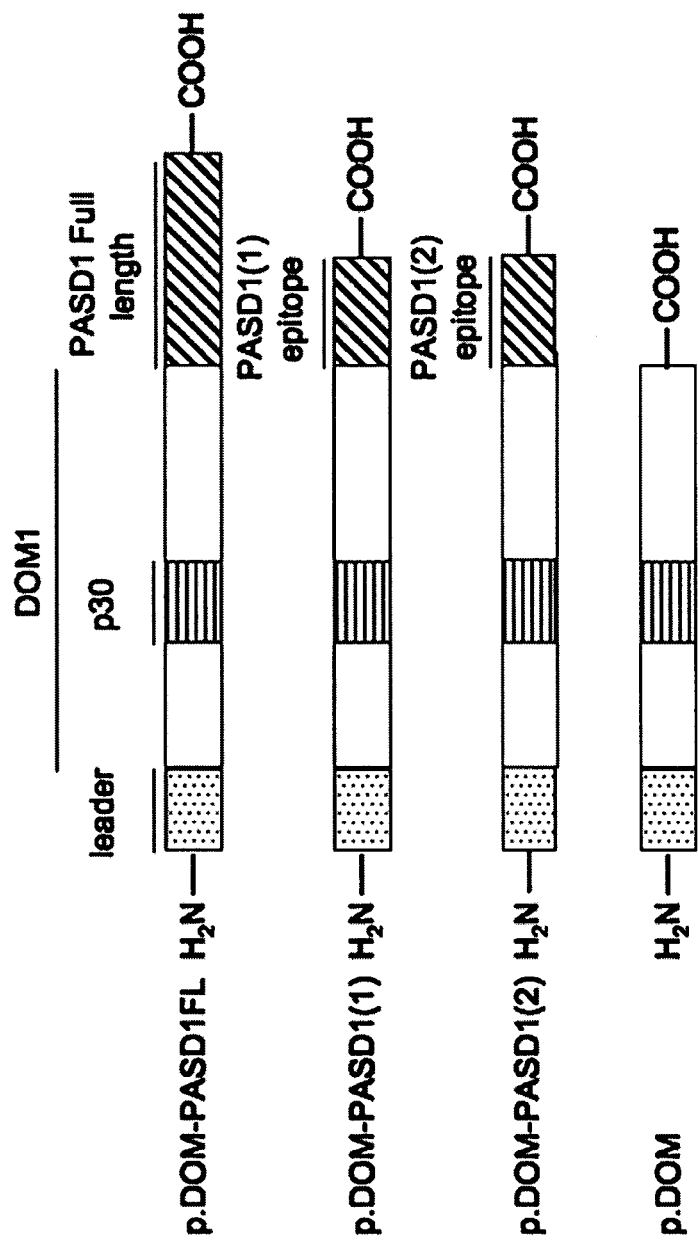

FIG. 7. Schematic representation of DNA fusion vaccine design.

Each vaccine contains at the $NH_2$ terminus the leader sequence of the $V_H$ heavy chain gene from the BCL1 lymphoma followed by a sequence encoding the first domain (DOM1) of Fragment C of Tetanus toxin, including the p30 $CD4^+$ Th epitope. The control vaccine contains no additional sequence whereas p.DOM-PASD1(1), p.DOM-PASD1(2) and p.DOM-PASD1FL include DNA sequence encoding the HLA-A*02001-restricted CTL epitopes PASD1(1), PASD1(2) or the full length sequence of PASD1 respectively, linked to the COOH terminus of DOM1.

FIG. 8. DNA vaccination induces $PASD1_{38}$ and $PASD1_{167}$ specific T-cell responses detectable ex vivo.

HHD mice were vaccinated with p.DOM-PASD1(1) (a), p.DOM-PASD1(2) (c), or p.DOM DNA vaccines (b and d). Splenocytes from individual mice were harvested on day 14 following priming, and the numbers of spot-forming cells (SFCs) secreting IFNγ were assessed ex vivo by ELISPOT assay after incubation without peptide, with an irrelevant peptide (1 μM), with p30 (1 μM), or with the relevant peptide (0.1 μM and 1 μM). A horizontal bar represents group medians. Responses were considered significant if the frequency of IFNγ-secreting cells was more than double the frequency detected in wells without peptide. Pooled data from two experiments with similar results.

FIG. 9. DNA vaccination induced T cells are able to specifically kill in vitro target cells loaded with the relevant peptide.

HHD mice were vaccinated with p.DOM-PASD1(1) (a, mice 1-4), p.DOM-PASD1(2) (b, mice 1-4), or p.DOM (a and b, Controls 1 and 2) DNA vaccines. Splenocytes were harvested on day 14 and cultured for 6 days with 0.1 μM of relevant peptide and IL-2 before measuring their CTL activity by $^{51}$Cr-release assay. The RMA-HHD target cells were either non-loaded, loaded with an irrelevant peptide, or with PASD1(1) or PASD1(2) peptides. The YAC-1 cells were used as a NK activity control target. Representative data of one of two experiments with the same results.

FIG. 10. Boost with electroporation improves the peptide specific T-cell responses.

HHD mice were vaccinated with p.DOM-PASD1(1) (a, b), p.DOM-PASD1(2) (c, f), or p.DOM (b, d and controls in e and f) DNA vaccines and received a booster injection immediately followed by electroporation on day 28. Splenocytes from individual mice were harvested 8 days later and the numbers of spot-forming cells (SFCs) secreting IFNγ were assessed ex vivo by ELISPOT assay as described above (a-d). Splenocytes were cultured during 6 days with 0.1 µM of relevant peptide and IL-2 before measuring their CTL activity by $^{51}$Cr-release assay (e and f). The target cells were the same as those used in FIG. 3. a-d are pooled data from two experiments with similar results. e and f are representative data of one of two experiments with the same results.

Figure 11:
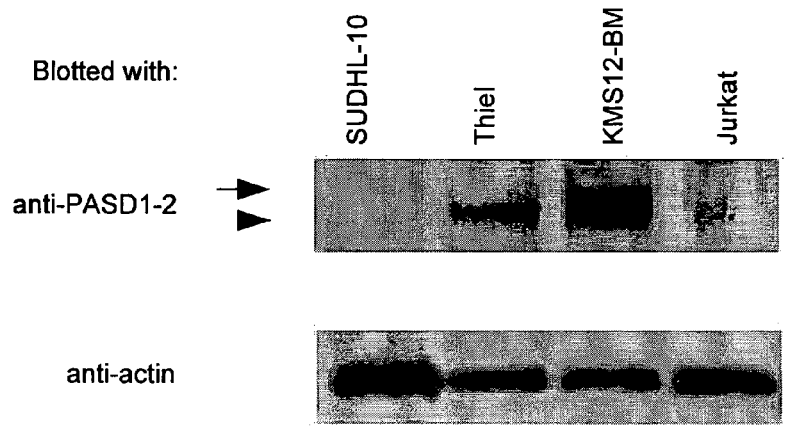

FIG. 11. Western blotting studies to show the presence of PASD1 protein in the KMS-12-BM cell line.

Bands of a comparable size to that previously reported in the control Thiel MM cell lysate (Cooper, et al 2006) are also observed in the KMS-12-BM cells using the antibodies PASD1-2 (arrowhead) and PASD1-1 (not shown). Antibody PASD1-2 also recognised an additional higher molecular weight band in the KMS-12-BM cell line (arrowed). No stained bands were detectable in either the PASD1-negative Jurkat or SUDHL-10 cell line lysates.

Figure 12:
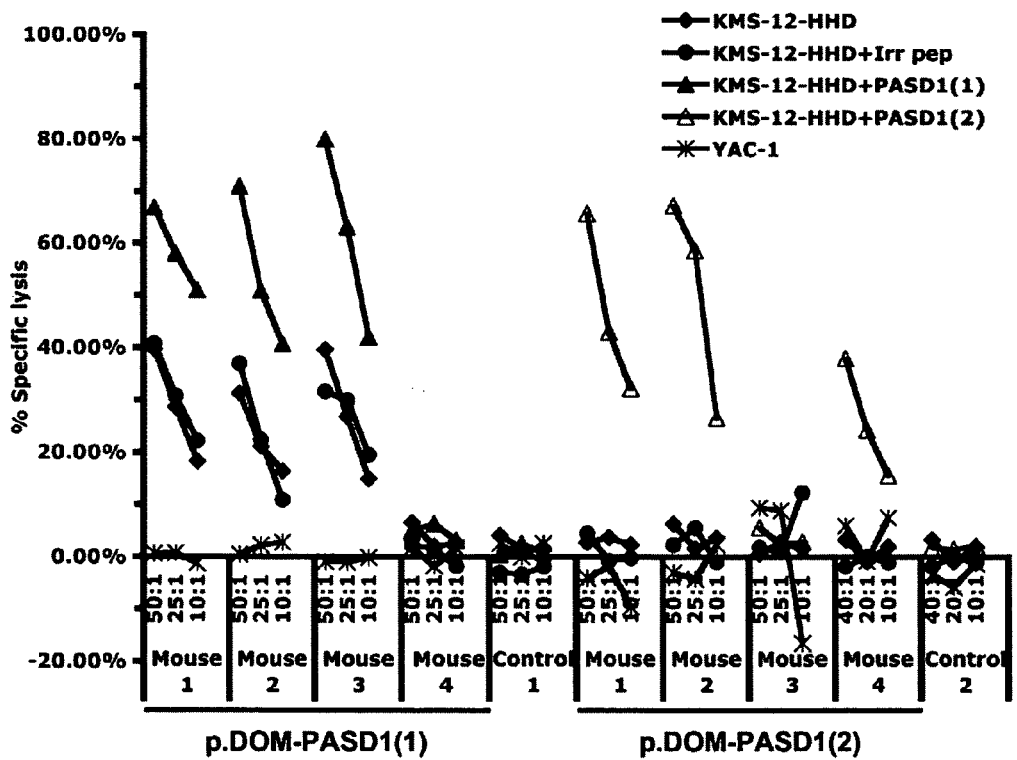

FIG. 12. DNA vaccination induced T cells are able to specifically kill in vitro human myeloma cell lines.

HHD mice were vaccinated with p.DOM-PASD1(1) (mice 1-4), p.DOM-PASD1(2) (mice 5-8), or p.DOM (Controls 1 and 2) DNA vaccines. Splenocytes were harvested on day 14 and cultured for 6 days with 0.1 µM of relevant peptide and IL-2 before measuring their CTL activity by $^{51}$Cr-release assay. The human KMS-12-HHD cells, either non-loaded, loaded with an irrelevant peptide, with PASD1(1) or PASD1 (2) peptides, were used as target cells. The YAC-1 cells were used as a NK activity control target. Representative data of one of two experiments with the same results.

Figure 13:
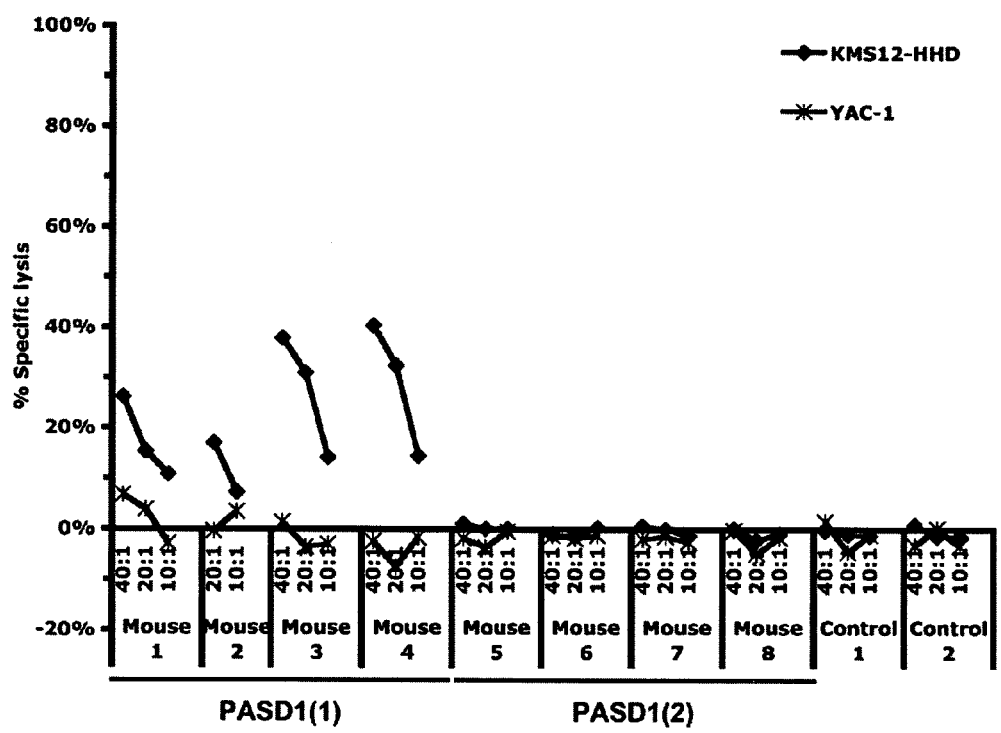

FIG. 13 p.DOM-PASD1FL induces PASD1(1) specific T-cell responses in HHD mice.

HHD mice were vaccinated with p.DOM-PASD1FL or p.DOM DNA vaccines. Splenocytes from individual mice were harvested on day 14, and the numbers of spot-forming cells (SFCs) secreting IFNγ were assessed ex vivo (A and B). Splenocytes were cultured for 6 days with 0.1 µM of relevant peptide as indicated, and IL-2 before measuring their CTL activity by $^{51}$Cr-release assay (C). The target cells were KMS-12-HHD cells expressing the endogenous PASD1 protein. A and B are pooled data from two experiments with similar results. C is representative data of one of two experiments with the same results.

DETAILED DESCRIPTION

The present inventors previously identified PASD1 as a novel immunogenic DLBCL-associated CTA using the SEREX technique (Liggins et al 2004a, Liggins et al 2004b). This approach, which relies upon the presence of a co-ordinated cellular and humoral response, has been used to identify immunogenic CTAs and other molecules that represent potential immunotherapeutic targets (Scanlan et al 2004, Preuss et al 2002). PASD1, encoded by a gene on Xq28, is a member of the CT-X group of CTAs (Scanlan et al 2004). Two splice variants were identified, PASD1a (639 amino acids) and PASD1b (773 amino acids). The first 638 amino acids are common to both proteins (Liggins et al 2004a).

Its restricted distribution in normal tissue but expression in a variety of haematological malignancies highlighted PASD1 as a potential immunotherapeutic target in both DLBCL and other hematological malignancies (Cooper et al 2006, Sahota et al 2006). This was of particular importance given previous reports of the paucity of CTA expression in B-cell lymphomas (Huang et al 2002, Xie et al 2003). The potential of PASD1 as an immunotherapeutic target was further supported by a study that reported PASD1 as a SEREX antigen in patients with acute myeloid leukaemia and which also demonstrated that PASD1 mRNA elicited a proliferative CD4-positive T-cell response in normal subjects (Guinn et al 2005).

The present invention is based upon the preparation of peptides derived from the PASD1 protein which are capable of producing a T-cell response. Thus, in a first aspect, the present invention relates to novel immunogenic peptides generated from the PASD1 protein.

By "immunogenic peptide" is meant a peptide chain of amino acids capable of stimulating an immune response. Peptides of the invention are from about 9 to about 25 amino acids in length. Such an immune response may take the form of a T-cell response in certain embodiments. T-cell responses may be mediated by CD4+ T cells (T helper, $T_H$ cells) or CD8+ T cells (cytotoxic T lymphocytes, CTLs).

The peptides of the invention include at least 9 consecutive amino acids of the amino acid sequence of any of SEQ ID Nos. 1 to 10. The peptides may be up to 25 amino acids long. Additional amino acids, where the peptides are more than 9 amino acids long, are preferably as indicated in SEQ ID Nos 1 and 6 to 10. They may (for example where the sequence presented is only 9 amino acids long—such as SEQ ID Nos 2 to 5, or where the peptide is longer than the sequence indicated in SEQ ID Nos 1 to 10 respectively) be derived from the amino acid sequence of the full length PASD1 protein as appropriate. They may, however, be derived from alternative sources provided that the minimum at least 9 consecutive amino acid sequence is retained, together with the ability to elicit the appropriate immunogenic response.

Thus, variants of the peptides may form part of the present invention. In particular, additional flanking sequences may be added, for example to improve the generation of an immunogenic response. Variant sequences preferably have at least 60%, at least 70%, at least 80%, at least 88%, at least 89%, at least 90%, at least 91%, at least 92%, at least 93%, at least 94%, at least 95%, or at least 96% amino acid sequence identity with the amino acid sequence of any of SEQ ID Nos. 1 to 10. Thus, the peptides may incorporate conservative substitutions which change one or more amino acids but ensure the peptides retain functionality in terms of stimulating an immune response, as defined herein. The peptides may incorporate 1, 2, 3, 4 or 5 conservative substitutions in certain embodiments. The peptides may incorporate synthetic amino acid analogues or modified amino acids as appropriate.

The inventors have identified and characterised five 9-10 amino acid sequences predicted to be immunogenic in the context of the MHC Class I HLA-A*0201 allele. These peptides (PASD1(1) to (5)) were identified using a selection process involving a combination of the web-based BIMAS (Parker et al 1994) and SYFPEITHI (Schuler et al 2007) programmes and homology screening.

In addition, five 20 amino acid sequences were predicted to be immunogenic in the context of the MHC Class II alleles DRB1-0101, DRB1-0301, DRB1-0401 or DRB1-0701 using a selection process involving a combination of the TEPITOPE predictive algorithm (Rajapaskse et al 2006) and the SYFPEITHI programme (PASD1(6) to (10)). The peptides identified and selected according to the criteria described herein were as follows:

PASD1(1)$_{39-48}$ (QLLDGFMITL); (SEQ ID No. 1)

PASD1(2)$_{168-176}$ (YLVGNVCIL); (SEQ ID No. 2)

PASD1(3)$_{64-72}$ (LLGHLPAEI); (SEQ ID No. 3)

PASD1(4)$_{495-503}$ (QLREQLQQL); (SEQ ID No. 4)

PASD1(5)$_{695-703}$ (ELSDSLGPV); (SEQ ID No. 5)

PASD1(6)$_{31-50}$ (DYFNQVTLQLLDGFMITLST); (SEQ ID No. 6)

PASD1(7)$_{42-61}$ (DGFMITLSTDGVIICVAENI); (SEQ ID No. 7)

PASD1(8)$_{58-77}$ (AENISSLLGHLPAEIVGKKL); (SEQ ID No. 8)

PASD1(9)$_{170-189}$ (VGNVCILRTQLLQQLYTSKA); (SEQ ID No. 9)

PASD1(10)$_{599-618}$ (NHPVRFLQAQPIVPVQRAAE). (SEQ ID No. 10)

Of note is that PASD1(6) peptide also contains a CTL epitope YFNQVTLQL (SEQ ID No. 27, PASD1$_{32-40}$) predicted to be immunogenic in the context of HLA-A*2402 (BIMAS) which is one of the most common allele in Eastern Asia (including Japan) and the northern tip of South America population.

Figure 1:
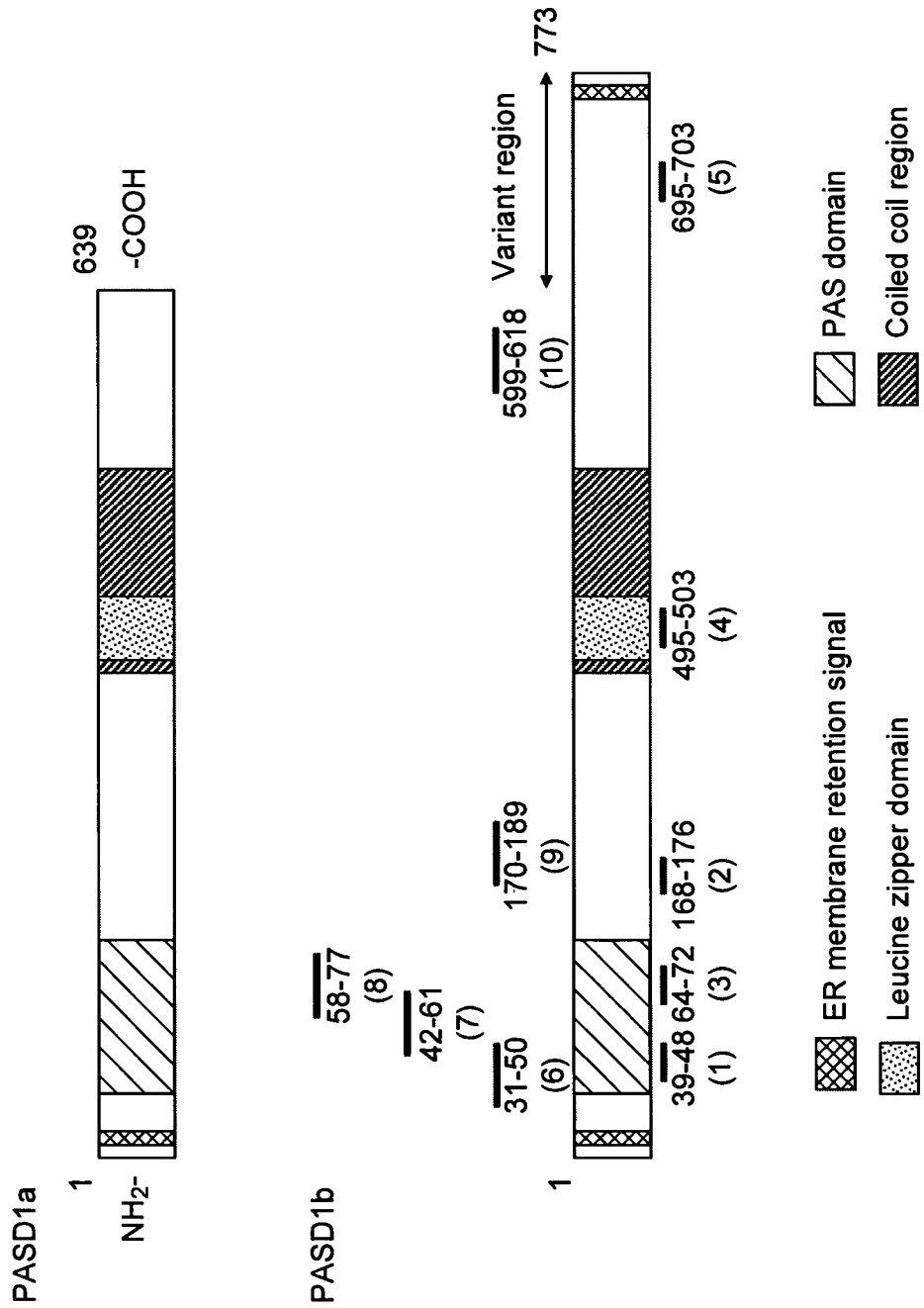
FIG. 1. Schematic diagram of the PASD1 protein isoforms.

The peptide sequences of PASD1(1), PASD1(2), PASD1 (3), PASD1(4), PASD1(6), PASD1(7), PASD1(8), PASD1(9) and PASD1(10) are common to both PASD1a and PASD1b protein isoforms while PASD1(5) is specific for the PASD1b isoform which represents a longer protein with a unique C-terminus that is absent in PASD1a. The positions of the peptide sequences of PASD1(1) to (10) in the PASD1 isoforms are shown in FIG. 1.

It should be noted that the prediction of peptides using web-based programmes alone is insufficient to identify immunogenic peptides that are correctly processed and presented from endogenous antigen in vivo. The ability of these peptides to stimulate an immune response must be confirmed in additional in vitro studies, as described below.

The sequence of the PASD1 gene has been deposited under GenBank accession number AY270020 and is included as SEQ ID No. 21. The amino acid sequence of PASD1a is available under Genpept accession number AAQ01136 and is included as SEQ ID No. 22. The amino acid sequence of PASD1b is available under UniProt accession number NP_775764 and is set forth as SEQ ID No. 23. The cDNA sequence encoding PASD1b is available as GenBank accession number NM_173493 and is set forth as SEQ ID No. 26.

It is interesting to note that PASD1(6) and PASD1(7) encompass the PASD1(1) CTL peptide, while PASD1(8) encompasses the PASD1(3) peptide. This raises the possibility of targeting CD4+ and CD8+ T cells simultaneously, in particular using these particular peptides comprising, consisting essentially of or consisting of SEQ ID Nos. 6, 7 or 8.

The peptides were selected according to their combined scores in the BIMAS/TEPITOPE and SYFPEITHI algorithms. Furthermore, they were screened using a BLAST search to ensure that they did not share high homology with known proteins. This is important to avoid adverse autoimmune responses.

In certain embodiments, the immunogenic peptides of the present invention comprise, consist essentially of or consist of at least 9 consecutive amino acids from any of PASD1(1) to (10) (SEQ ID Nos. 1 to 10) or SEQ ID No. 27.

In further embodiments, the immunogenic peptides comprise, consist essentially of or consist of the amino acid sequence of any of PASD1(1) to (10) (SEQ ID Nos 1 to 10) or SEQ ID No 27.

In a further aspect, the present invention relates to nucleic acids encoding immunogenic peptides of the present invention. Such nucleic acids may generally be DNA or RNA based, but may also incorporate modified or synthetic nucleotides as appropriate. They may be single and double stranded as appropriate. In certain embodiments, the nucleic acids comprise, consist essentially of or consist of the nucleotide sequence of any of SEQ ID Nos. 11 to 20.

The nucleic acid molecules according to the invention may, advantageously, be included in a suitable expression vector to express the peptides encoded therefrom in a suitable host. Incorporation of cloned DNA into a suitable expression vector for subsequent transformation of said cell and subsequent selection of the transformed cells is well known to those skilled in the art. Any suitable technique may be employed. Examples are provided in Sambrook and Russell (2001), Molecular cloning: A Laboratory Manual, Cold Spring Harbour Laboratory.

An expression vector, according to the invention, includes a vector comprising a nucleic acid according to the invention operably linked to one or more regulatory sequences, such as promoter regions, that are capable of effecting expression of peptides encoded by the nucleic acid. A vector can include a large number of nucleic acids which can have a desired sequence inserted therein by, for example, using an appropriate restriction enzyme and ligating the sequence in the vector. The term "operably linked" refers to a juxtaposition wherein the components described are in a relationship permitting them to function in their intended manner. Such vectors may be transformed into a suitable host cell to provide for expression of a peptide according to the invention. The vectors may be capable of replicating within a host environment and may also comprise one or more restriction sites for nucleases which permits them to be restricted in a selective manner at a particular location for insertion of a new nucleic acid molecule or sequence therein. Thus, in a further aspect, the invention provides a process for preparing peptides according to the invention, which comprises cultivating a host cell, transformed or transfected with an expression vector as described herein under conditions which facilitate or permit expression of the peptide, and recovering the expressed peptide. Any suitable method of recovery, including appropriate purification techniques, may be employed.

In this regard, the nucleic acid molecule may encode a peptide of the invention or a peptide having a prosequence, including encoding a leader sequence on the prepeptide which is cleaved by the host cell to form the peptide of the invention.

The vectors may be, for example, plasmid, virus or phagemid vectors. They may be provided with an origin of replication, a promoter for the expression of the peptide from the nucleic acid and/or a regulator of the promoter for example. The vectors may contain one or more selectable markers, such as, for example, an antibiotic resistance gene.

Regulatory elements required for expression include promoter sequences to bind RNA polymerase and to direct an appropriate level of transcription initiation and also translation initiation sequences for ribosome binding. For example, a bacterial expression vector may include a promoter such as the lac promoter and for translation initiation the Shine-Dalgarno sequence and the start codon AUG. Similarly, a eukaryotic expression vector may include a heterologous or homologous promoter for RNA polymerase II, a downstream polyadenylation signal, the start codon AUG, and a termination codon for detachment of the ribosome. However, the precise regulatory elements required for expression of a gene of interest may vary between different cell types but generally include 5' non-transcribing and non-translating regions which are required for initiation of translation and transcription. Such vectors may be obtained commercially or be assembled from known vectors using methods well known in the art.

Transcription of DNA encoding the peptides of the present invention by higher eukaryotes may be optimised by including an enhancer sequence in the vector. Enhancers are cis-acting elements of DNA that act on a promoter to increase the level of transcription.

Nucleic acid molecules according to the invention may be inserted into a suitable vector in an antisense orientation in order to provide for the production of antisense RNA. Antisense RNA or other antisense nucleic acids, including antisense peptide nucleic acid (PNA), may be produced by synthetic means.

In accordance with the present invention, a defined nucleic acid includes not only the identical nucleic acid but also any minor base variations including, in particular, substitutions in cases which result in a synonymous codon (a different codon specifying the same amino acid residue). The term "nucleic acid" also includes the complementary sequence to any single stranded sequence given regarding base variations.

A further aspect of the invention provides a host cell or organism, transformed or transfected with an expression vector according to the invention. The cell or organism may be transformed or transfected using any suitable technique. Many examples are well known in the art, such as electroporation and use of liposomes. The host cell or organism may advantageously be used in a method of producing peptides of the invention, which comprises recovering any expressed peptide from the host or organism transformed or transfected with the expression vector.

Any suitable host cell or organism may be used, for example a prokaryotic or eukaryotic host cell. Examples include but are not limited to bacteria, yeasts, higher plant cells in culture, insect cells in culture and mammalian cells in culture.

According to a further aspect of the invention there is also provided a transgenic cell, tissue or non-human organism comprising a transgene capable of expressing a peptide according to the invention. The term "transgene capable of expressing" as used herein encompasses any suitable nucleic acid which encodes and results in expression of a peptide(s) having the same function and/or activity as the peptides of the invention. The transgene, may include, for example, genomic nucleic acid isolated from human cells or synthetic nucleic acid, including DNA integrated into the genome or in an extrachromosomal state. Preferably, the transgene comprises a nucleic acid encoding a peptide according to the invention as described herein.

Transgenic non-human organisms may be utilised as model systems for studying both normal and disease cell processes. In general, to create such transgenic animals an exogenous gene with or without a mutation is transferred to the non-human animal host system and the phenotype resulting from the transferred gene is observed. Other genetic manipulations can be undertaken in the vector or host system to improve the gene expression leading to the observed phenotype (phenotypic expression). The gene may be transferred via a vector under the control of different inducible or constitutive promoters, may be overexpressed or the endogenous homologous gene may be rendered unexpressible, and the like (WO 92/11358). The vector may be introduced by any suitable method. Examples include transfection or electroporation, for example, in embryonic stem cells. The cells that have the exogenous DNA incorporated into their genome, for example, by homologous recombination, may subsequently be injected into blastocytes for generation of the transgenic animals with the desired phenotype. Successfully transformed cells containing the vector may be identified by well known techniques such as lysing the cells and examining the DNA, by, for example, Southern blotting or using the polymerase chain reaction.

The peptide expressed by said transgenic cell, tissue or organism or a functional equivalent thereof also forms part of the present invention. Recombinant peptides may be recovered and purified from host cell cultures by any appropriate method known in the art. Examples include ammonium sulfate or ethanol precipitation, acid extraction, anion or cation exchange chromatography, phosphocellulose, chromatography, hydrophobic interaction chromatography, affinity chromatography, hydroxyapatite chromatography and lectin chromatography.

In yet a further aspect, the present invention relates to a vaccine composition including an immunogenic peptide of the invention. Alternatively, the vaccine may comprise a nucleic acid, expression vector or host cell of the present invention. Also comprised within the scope of the invention are mimotopes which exhibit the same immune response initiating characteristics as the peptides of the invention. The invention also therefore includes peptides incorporating the epitopes or mimotopes described. A mimotope is described as an entity which is sufficiently similar to (the epitopes of) the peptides of the invention so as to be capable of producing a substantially identical immunogenic response. Suitable techniques for detecting and/or quantifying an immunogenic response induced by a peptide are described herein. They may be generated by addition, deletion or substitution of selected amino acids which, advantageously, means that the peptides of the invention may be modified, for example, for ease of delivery on a carrier.

Carriers which may be used with the immunogenic peptides of the present invention will be well known to those of skill in the art. The function of the carrier, such as exosomes (Bianco et al 2007), may be to provide cytokine help to facilitate the induction of an immune response following administration of the vaccine composition to an individual. Methods for immunisation, including formulating the vaccine composition and selecting appropriate doses are well known to those of skill in the art.

In other embodiments, the vaccine compositions described herein may comprise one or more immunostimulants in addition to the immunogenic peptide, nucleic acid, expression vector or host cell of the present invention. An immunostimulant refers to essentially any substance that enhances or potentiates an immune response (antibody and/or cell-mediated) to an exogenous antigen. One preferred type of immunostimulant comprises an adjuvant. Many adjuvants contain a substance designed to protect the antigen from rapid catabolism, such as aluminium hydroxide or mineral oil. They may also incorporate a stimulator of immune responses, such as a lipid A, *Bortadella pertussis* or *Mycobacterium tuberculosis* derived protein. Certain adjuvants are commercially available such as, for example, Freund's Incomplete Adjuvant and Complete Adjuvant (Difco Laboratories, Detroit, Md.; Montanide ISA-51 (Seppic, Fairfield, N.J.); Merck Adjuvant 65

(Merck and Company, Inc., Rahway, N.J.); AS-2 (SmithKline Beecham, Philadelphia, Pa.); aluminum salts such as aluminum hydroxide gel (alum) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and quil A. Cytokines, such as GM-CSF, interleukin-2, -7, -12, and other like growth factors, may also be used as adjuvants.

Within certain embodiments of the invention, the adjuvant composition is one that potentiates an immune response predominantly of the Th1 type. High levels of Th1 type cytokines (e.g., IFN-γ, TNFα, IL-2 and IL-12) tend to favour the induction of cell mediated immune responses to an administered antigen. In contrast, high levels of Th2-type cytokines (e.g., IL-4, IL-5, IL-6 and IL10) tend to favour the induction of humoral immune responses. Following application of a vaccine as provided herein, a patient will support an immune response that includes both Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman (1989).

The present invention also provides a polyvalent vaccine composition comprising a vaccine of the invention in combination with other antigens, in particular antigens useful for treating cancers, autoimmune diseases and related conditions. Such a polyvalent vaccine composition may include a Th-1 inducing adjuvant as hereinbefore described.

The present invention further relates to isolated T cells specific for immunogenic peptides of the invention. Methods for generating and isolating such cells are available to those of skill in the art. Examples can be found in Xue et al (2005) and in Thomas et al (2007).

The present invention also provides pharmaceutical compositions which comprise the immunogenic peptides of the invention. In some embodiments, the pharmaceutical compositions comprise the nucleic acid, expression vector or a host cell of the invention.

In other embodiments, the pharmaceutical composition of the invention may comprise an immunogenic peptide capable of stimulating a CTL response and an immunogenic peptide capable of stimulating a $T_H$ response for simultaneous, sequential or separate administration.

In further embodiments, the pharmaceutical compositions may include two or more of an immunogenic peptide, a nucleic acid, an expression vector or a host cell as described herein for simultaneous, sequential or separate administration.

In certain embodiments, the present invention relates to polytope compositions which may comprise more than one immunogenic peptide of the invention. In these embodiments the immunogenic peptides may be the same or different. They may be formulated for simultaneous, sequential or separate administration.

The pharmaceutical compositions of the present invention may be formulated with any suitable carrier or excipient known in the art. Furthermore, the pharmaceutical compositions may be formulated into any suitable form. Examples known in the art include nanoparticles, ampoules, capsules, creams, elixirs, emulsions, microemulsions, fluids, drops, injections, solutions, lotions, sprays, powders, suspensions, syrups, tablets, tinctures or ointments.

The pharmaceutical compositions of the present invention may be administered by any suitable route. Examples known in the art include intradermal, subcutaneous, intramuscular, intravenous, intraosseous, and intraperitoneal infusion or injection, oral or sublingual administration and inhalation.

In yet a further aspect, the present invention relates to methods of diagnosing cancer. The identification of peptides linked to certain tumours and lymphomas renders it possible to detect or identify patients suffering from cancer and will help in determining the appropriate course of treatment. The method involves screening patient samples for the presence of T cells specific for the immunogenic peptides of the invention. Such methods of screening are available to those of skill in the art.

The diagnostic methods described herein may be carried out in vitro, starting with a sample isolated from a patient. Alternatively they may include the step of obtaining the sample in certain embodiments.

Patient samples may be of any suitable form. Examples include bodily fluids such as blood, saliva, urine, lymph, interstitial fluid or sputum, or a tissue or cell sample obtained by biopsy.

A method of predicting a clinical outcome for patient with a haematologically derived malignancy is also contemplated by the current invention. The method comprises the steps of:

(a) isolating peripheral blood mononuclear cells (PBMCs) from a patient with a haematologically derived malignancy;

(b) screening said PBMCs for recognition of an immunogenic peptide of the invention;

(c) assigning a predicted positive clinical outcome to the patient where the PBMCs recognise the immunogenic peptide described herein or a predicted negative clinical outcome to the patient where the PBMCs do not recognise the immunogenic peptide of the invention.

The method of predicting a clinical outcome may be performed in vitro, starting with a sample isolated from a patient. This will include screening the sample for PASD1 expression using immunolabelling, biochemical or molecular biological techniques. Alternatively it may include the step of obtaining the sample in certain embodiments.

By "screening" it is meant applying any suitable technique for determining whether the PBMC in question recognises an immunogenic peptide of the invention. In certain embodiments this may involve culturing the PBMCs with the immunogenic peptide or peptides and monitoring γ-IFN release. Release of γ-IFN by the PBMC in the presence of an immunogenic peptide indicates recognition. In other cases testing using peptide specific MHC tetramers may be utilised. Suitable controls may be employed.

The term "recognition" as used herein refers to immunological recognition resulting in an immune response, for example CTL activation or γ-IFN release and/or the binding of cells to MHC tetramers.

The present invention also relates to methods of treatment of cancer. These methods may involve administering a therapeutically effective amount of an immunogenic peptide, a nucleic acid, an expression vector, a host cell, a vaccine, an isolated T-cell, or a pharmaceutical composition of the invention as described herein to a patient in need thereof. The route of administration will vary depending on the particular cancer being treated and may be determined by one of skill in the art.

Examples include, but are not limited to, intradermal, subcutaneous, intramuscular, intravenous, intraosseous, and intraperitoneal infusion or injection, oral or sublingual administration and inhalation.

Similarly, the effective dose will vary according to the severity of the disease and other patient-specific factors, such as height, age and weight of the patient. The appropriate dose can be readily determined by those of skill in the art.

The present invention further relates to a method of treatment of cancer, comprising the steps of:
 (a) isolating a cell population containing or capable of producing CTLs and/or $T_H$ cells from a subject;
 (b) treating the cell population with an immunogenic peptide(s) described herein optionally together with a proliferative agent;
 (c) screening the cell population for CTLs and/or $T_H$ cells with specificity to an immunogenic peptide(s) described herein;
 (d) administering the cell population to a patient suffering from cancer.

In certain embodiments, the CTLs and/or $T_H$ cells with specificity to an immunogenic peptide(s) described herein are isolated from the cell population and administered to a patient suffering from cancer.

The present invention also contemplates a method of treatment of cancer, comprising the steps of:
 (a) isolating a cell population containing or capable of producing CTLs and/or $T_H$ cells from a subject;
 (b) treating the cell population with an immunogenic peptide(s) described herein optionally together with a proliferative agent;
 (c) screening the cell population for CTLs and/or $T_H$ cells with specificity to an immunogenic peptide(s) described herein;
 (d) cloning the T cell receptor (TCR) genes from the CTLs and/or $T_H$ with specificity to the immunogenic peptide(s) described herein;
 (e) transducing the TCR gene cloned in step (d) into either:
  i. cells from the patient; or
  ii. cells from a donor; or
  iii. prokaryotic or eukaryotic cells for the generation of monoclonal TCR (mTCRs); and
 (f) administering the cells or mTCRs from step (e) to a patient suffering from cancer.

Methods of cloning T-cell receptor genes have been described previously and are available to those of skill in the art (Ashfield and Jakobsen 2006, Xue & Stauss 2007, Stauss et al 2007).

In certain embodiments the subject from which the cell population is isolated is the patient in need of treatment (i.e. suffering from cancer). Alternatively, the cell population may be isolated from a normal subject. The term "normal subject" is intended to mean a subject without cancer. In certain embodiments, the normal subject may be a subject with particular MHC(HLA) alleles. The particularly favourable HLA alleles may be:
 MHC Class I:
  HLA-A*0201
  HLA-A*2402
 MHC Class II:
  HLA-DRB1*0101
  HLA-DRB1*0301
  HLA-DRB1*0401
  HLA-DRB1*0701

A cell population is any group of cells that contains or is capable of producing CTLs and/or $T_H$ cells. This includes but is not limited to blood cells, in particular peripheral blood mononuclear cells (PBMCs), which may be stimulated to produce CTLs and/or $T_H$ cells.

The term "proliferative agents" is intended to encompass any compound or composition that causes cellular proliferation. Examples include but are not limited to dendritic cells and cytokines.

By "screening" it is meant applying any suitable technique for determining whether the cell in question recognises an immunogenic peptide of the invention. In certain embodiments this may involve culturing the cells with the immunogenic peptide or peptides and monitoring γ-IFN release. Release of γ-IFN in the presence of an immunogenic peptide indicates recognition. In other cases testing using peptide specific MHC tetramers may be utilised. Suitable controls may be employed. Where appropriate, screening may also include purification and/or isolation of cells that recognise immunogenic peptide(s) of the present invention. Methods of cell purification and/or isolation will be well known to those of skill in the art.

In certain embodiments, the immunogenic peptides, nucleic acids, expression vectors, host cells, vaccines, isolated T cells, pharmaceutical compositions and methods of the present invention may be particularly appropriate to a subgroup of patients carrying particular MHC (HLA) alleles. The particularly favourable HLA alleles may be:
 MHC Class I:
  HLA-A*0201
  HLA-A*2402
 MHC Class II:
  HLA-DRB1*0101
  HLA-DRB1*0301
  HLA-DRB1*0401
  HLA-DRB1*0701

Alternatively, the immunogenic peptides, nucleic acids, expression vectors, host cells, vaccines, isolated T cells, pharmaceutical compositions and methods of the present invention are useful with any HLA allele group.

EXAMPLES

The present invention will be further understood by reference to the following experimental examples.

Cytolytic T-Cell Response to the PASD1 Cancer Testis Antigen in Patients with Diffuse Large B-Cell Lymphoma Materials and Methods Subjects Peripheral blood was obtained from 50 patients with B-cell lymphoma attending the Haematology Departments of the John Radcliffe Hospital, Oxford (n=44) and Milton Keynes General Hospital (n=6). The patient cohort consisted of 36 patients with de novo DLBCL, 11 patients with transformed DLBCL and 3 patients with T-cell rich B cell lymphoma. The patients presented with differing stages of disease and their clinical details and treatment protocols are summarized in Table 1.

TABLE 1

Clinical details of DLBCL cases.

| ID | Diagnosis | Subtype# | Stage | IPI | Sex | Age | Treatment | Current status from time of diagnosis |
|---|---|---|---|---|---|---|---|---|
| 1 | DLBCL(dn) | NGC | I | 1 | F | 23 | CHOP-R | CR (21 months) |
| 2 | DLBCL(dn) | GCB | 3 | 3 | M | 67 | CHOP-R + MTX + RX | CR (20 months) |
| 3 | DLBCL(dn) | ND* | 3 | 3 | M | 81 | VIN/PRED | PR (17 months) |
| 4 | DLBCL(dn) | NGC | 1 | 2 | F | 76 | CHOP-R | PR (29 months) |
| 5 | DLBCL(dn) | GCB | 1 | 0 | M | 52 | CHOP-R + RX | CR (12 months) |
| 6* | DLBCL (dn) | NGC | 2 | 1 | M | 21 | CHOP-R | Died (19 months) |
| 7 | DLBCL (dn) | GCB | 2 | 0 | M | 49 | CHOP-R + MTX | PR (19 months) |
| 8 | DLBCL(dn) | GCB | 1 | 0 | M | 63 | CHOP-R | CRU (24 months) |
| 9 | DLBCL(dn) | NGC | 3 | 2 | F | 71 | CHOP-R | PR (23 months) |
| 10* | DLBCL | GCB | 1 | 0 | F | 60 | CHOP-R + RICE + ESHAP + BEAM + TX | CR (13 months) |
| 11 | DLBCL(dn) | GCB | 1 | 1 | M | 38 | CODOX-M + RX | PR (17 months) |
| 12 | DLBCL(dn) | GCB | 1 | 0 | F | 59 | CHOP-R | CR (22 months) |
| 13 | DLBCL (dn) | GCB | 3 | 3 | M | 67 | CHOP-R + MTX | PR (17 months) |
| 14 | DLBCL(dn) | NGC | 3 | 2 | M | 63 | CHOP-R + MTX | CR (12 months relapse 2 months) |
| 15 | DLBCL(dn) | NGC | 3 | 3 | M | 85 | VIN/PRED | Died (6 months) |
| 16 | DLBCL(dn) | GCB | 2 | 2 | M | 59 | CHOP-R | CR (22 months) |
| 17 | DLBCL(dn) | GCB | 3 | 4 | M | 60 | CHOP-R | CR (17 months) |
| 18 | DLBCL(dn) | NGC | 4 | 4 | M | 74 | CNOP-R | CR (14 months) |
| 19 | DLBCL(dn) | GCB | 4 | 2 | M | 56 | CHOP-R + RX | Died (19 months) |
| 20 | DLBCL(dn) | NGC | 2 | 2 | F | 70 | NONE | Died (2 months) |
| 21 | DLBCL(dn) | GCB | 1 | 3 | M | 73 | CHOP-R | PR (23 months) |
| 22 | DLBCL(dn) | GCB | 3 | 1 | M | 53 | CHOP-R | PR (24 months) |
| 23 | DLBCL (dn) | NGC | 4 | 4 | F | 68 | CHOP-R | Died (2 weeks) |
| 24 | DLBCL(dn) | NGC | 1 | 1 | F | 62 | CHOP-R | CR (11 months) |
| 25 | DLBCL(dn) | GCB | 2 | 2 | F | 74 | CHOP-R | Died (6 months) |
| 26 | DLBCL(dn) | GCB | 2 | 2 | F | 62 | CHOP-R | PR (29 months) |
| 27 | DLBCL(dn) | GCB | 1/2 | 2 | M | >60 | CHOP-R | CR (28 months) |
| 28 | DLBCL(dn) | GCB | 1 | 2 | M | >60 | CHOP-R | CR (26 months) |
| 29 | DLBCL(dn) | GCB | 3 | 4 | F | 71 | CHOP-R | Died (7 months) |
| 30 | DLBCL(dn) | NGC | 3 | 3 | M | 62 | CHOP-R | CR (24 months) |
| 31 | DLBCL(dn) | NGC | 1 | 1 | M | 63 | CHOP-R | CR (23 months) |
| 32 | DLBCL(dn) | GCB | 1 | 3 | M | 75 | CNOP-R | CR (23 months) |
| 33 | DLBCL(dn) | GCB | 3 | 3 | M | 46 | CHOP-R | CR (22 months) |
| 34 | DLBCL(dn) | NGC | 2 | 1 | M | 61 | CHOP-R | CRU (21 months) |
| 35 | DLBCL(dn) | GCB | 3 | 2 | M | 45 | CODOX-M + CHOP + MTX + RX + IVAC + R + RICE + ESHAP | PR (15 months) |
| 36 | DLBCL(dn) | NGC | 4 | 2 | M | 58 | CHOP-R + RICE + BEAM + TX | PR (15 months) |
| 37 | DLBCL (t) | ND | 1 | 2 | M | 59 | CHOP-R + RX | CR (22 months) |
| 38 | DLBCL (t) | ND | 3 | 2/3 | M | 71 | PMitCEBO + PRED + RX + VIN | CR (12 months) |
| 39 | DLBCL (t) | ND | 4 | 2 | F | 39 | CHOP-R | Died (6 months) |
| 40 | DLBCL (t) | ND | | | M | 64 | CHOP-R | Died (4 months) |
| 41 | DLBCL (t) | ND | 4 | 4 | F | 60 | CHOP-R + CNOP-R | CR (29 months) |
| 42 | DLBCL (t) | ND | 2 | 1 | F | 54 | CNOP-R | PR (5 months) |
| 43 | DLBCL (t) | ND | 4 | 2 | F | 60 | CHOP-R + RX | CR (24 months) |
| 44 | DLBCL (t) | ND | 1 | 0 | M | 56 | CHOP-R + MTX ESHAP + BEAM + TX | CR (24 months) |
| 45 | DLBCL (t) | ND | 2 | 3 | M | 65 | CHOP-R | CR (21 months) |
| 46 | DLBCL (t) | ND | 4 | 4 | F | 47 | CHOP-R | CR (19 months) |
| 47 | DLBCL (t) | ND | 2 | 0 | M | 51 | CHOP-R | CR (29 months) |
| 48 | TCR | ND | 3 | 2 | F | 80 | PMITCEBO-R TO MARCH 2006 | CR (12 mo) |

TABLE 1-continued

Clinical details of DLBCL cases.

| ID | Diagnosis | Subtype# | Stage | IPI | Sex | Age | Treatment | Current status from time of diagnosis |
|---|---|---|---|---|---|---|---|---|
| 49 | TCR | | 4 | 4 | F | 39 | CODOX + IVAC + MTX + R | CR (27 months) |
| 50 | TCR | — | 3 | 4 | M | 74 | CHOP-R | PR (18 months) |

DLBCL(dn) Diffuse large B-cell lymphoma de novo;
DLBCL (t) —Diffuse large B-cell lymphoma transformed;
TCR—T-cell rich B cell lymphoma;
subtyped according to expression of CD10, BCL-6 and MUM1 according to Hans et al.;
GCB—Germinal center derived;
NGC—Non-germinal center-derived;
CHOP-R—Cyclophosphamide, doxorubicin, vincristine, prednisolone, Rituximab;
MTX—Intrathecal methotrexate;
RX—Radiotherapy;
PRED—Prednisolone;
VIN—Vinblastine;
RICE—Rituximab, ifosfamide, carbplatin, etoposide;
ESHAP—etoposide, methyprednisolone, cytarabine, cisplatin;
TX—Autologous transplant;
CODOX-M—Cyclophosphamide, vincristine, doxorubicin, methotrexate;
BEAM—BCNU -(bis-chloro-ethyl nitrosourea), Etoposide, cytarabine, melphalan;
CNOP-R—Cyclophosphamide, mitoxantrone, vincristine, prednisolone, Rituximab;
PMitCEBO—Prednisolone, mitoxantrone, cyclophosphamide, etoposide, bleomycin, vincristine;
CODOX—cyclophosphamide, doxorubicin, vincristine, methotrexate,
IVAC—ifosfamide, etoposide, cytatabine.
*Sample at relapse;
CR—Complete response; PR—Partial response: CRU—Complete remission unconfirmed.

Peptides

Five 9-10 amino acid sequences predicted to be immunogenic in the context of the MHC Class I HLA-A*0201 allele were identified using the web-based BIMAS (Parker et al 1994) and SYFPEITHI (Schuler et al 2007) programmes. BLAST analysis was performed to exclude peptides that shared significant sequence identity with human proteins other than PASD1. The peptides identified and selected were as follows:

$PASD1(1)_{39-48}$ (QLLDGFMITL); (SEQ ID No. 1)

$PASD1(2)_{168-176}$ (YLVGNVCIL); (SEQ ID No. 2)

$PASD1(3)_{64-72}$ (LLGHLPAEI); (SEQ ID No. 3)

$PASD1(4)_{495-503}$ (QLREQLQQL); (SEQ ID No. 4)

$PASD1(5)_{695-703}$ (ELSDSLGPV). (SEQ ID No. 5)

A control irrelevant peptide from HIV-1 reverse transcriptase (ILKEPVHGV) (SEQ ID No. 24) (Parker et al 1992) predicted to bind to HLA-A*0201 was also used. All peptides were synthesized by standard chemistry on a multiple peptide synthesizer (Invitrogen, UK) and were >90% pure. Lyophilized peptides were diluted in dimethyl sulfoxide and stored at −20° C.

The peptide sequences of PASD1(1), PASD1(2), PASD1(3) and PASD1(4) were common to both PASD1a and PASD1b protein isoforms while PASD1(5) was specific for the PASD1b isoform which represents a longer protein with a unique C-terminus that is absent in PASD1a.

In addition, five 20 amino acid sequences predicted to be immunogenic in the context of the MHC Class II alleles DRB1-0101, DRB1-0301, DRB1-0401 or DRB1-0701 were identified using a selection process involving a combination of the TEPITOPE predictive algorithm (Rajapaskse et al 2006) and the SYFPEITHI programme (PASD1(6) to (10)). BLAST analysis was performed to exclude peptides that shared significant sequence identity with human proteins other than PASD1. The peptides identified were as follows:

$PASD1(6)_{31-50}$ (DYFNQVTLQLLDGFMITLST); (SEQ ID No. 6)

$PASD1(7)_{42-61}$ (DGFMITLSTDGVIICVAENI); (SEQ ID No. 7)

$PASD1(8)_{58-77}$ (AENISSLLGHLPAEIVGKKL); (SEQ ID No. 8)

$PASD1(9)_{170-189}$ (VGNVCILRTQLLQQLYTSKA); (SEQ ID No. 9)

$PASD1(10)_{599-618}$ (NHPVRFLQAQPIVPVQRAAE). (SEQ ID No. 10)

The positions of the peptide sequences in the PASD1 isoforms are shown in FIG. 1. A control irrelevant peptide from HIV-1 reverse transcriptase was also used (DESFRKYTAFTIPSMNNETP) (SEQ ID No. 25).

Antibodies

Monoclonal Antibodies:

Both of the anti-PASD1 monoclonal antibodies, PASD1-1 (recognizing a region common to both PASD1a and PASD1b) and PASD1-2 (recognizing an epitope in the C-terminus of PASD1b) were produced in the inventors' laboratory, as previously described (Cooper et al 2006). Antibodies to BCL-6 and CD10 were purchased from DAKOCytomation (Ely, Cambridgeshire, UK) while anti-MUM1 was a kind gift from Prof. B. Falini (Perugia, Italy). The anti-HLA-A*0201 (BB7.2) was purchased from BD BioSciences (Oxford, UK).

Polyclonal Antibodies:

The Envision-HRP and Mach Three-HRP labeling kits were obtained from DAKOCytomation and BD Biosciences, respectively.

Cell Lines

The following cell lines were obtained and cultured as described previously (Cooper et al 2006): PASD1-positive, HLA-A*0201-positive and HLA-DRB1*0401-positive Thiel (myeloma-derived), the PASD1-positive, HLA-A*0201-negative and HLA-DR*0301-positive OCI-Ly3 (DLBCL-derived) and KM-H2 (Hodgkin's lymphoma (HL)-derived and the PASD1-negative, HLA-A*0201-positive and HLA-DRB1*0101-positive SUDHL-6 (DLBCL-derived).

Preparation and Culture of PBMCs

PBMCs were prepared in RPMI1640 containing 10% FCS (RPMI1640/FCS, Invitrogen Ltd., Paisley, Scotland) as described previously (Ait-Tahar et al 2006). PBMCs (0.5× $10^5$) in 200 µl of RPMI1640/FCS were added to each well of a 96-well round-bottomed plate and incubated for 8-10 days with 1-10 µmol of one of the following: the PASD1(1), PASD1(2), PASD1(3), PASD1(4), PASD1(5), PASD1(6), PASD1(7), PASD1(8), PASD1(9), PASD1(10) or the control HIV peptides, 10 µl phytohaemagglutinin (PHA; Sigma-Aldrich Co. Ltd, Dorset, UK) or tissue culture media only. Recombinant interleukin-2 (IL-2: 20 IU/ml; Roche Diagnostics, Indianapolis, Ind.) and recombinant IL-7 (25 ng/ml; R&D Systems, Minneapolis, Minn.) were added on days 2, 5 and 7.

ELISPOT Assay

After 8-10 days of culture, cells were washed and incubated for 18 hours with RPMI 1640/FCS at 37° C. in 5% $CO_2$ with one of the PASD1 peptides, HIV control peptides, PHA or medium only. Peptides were used at 10 µmol and all cultures were carried out in triplicate. γ-IFN release assays were performed according to manufacturer's instructions (Mabtech, Stockholm, Sweden). Spots were counted using an automated ELISPOT reader (Autimmun-Diagnostika, Strasberg, Germany). Results were considered highly positive if the number of spots in the test wells were at least twice those present in the control cultures and assays were excluded if there were more than 25 spots per well in the absence of peptides.

Generation of CTL and $T_H$ Cell Lines

PBMCs ($2\times10^6$) were cultured in RPMI-1640/FCS containing 10 µM of the appropriate PASD1 peptides. After 72 hours, an equal volume of RPMI1640/FCS containing 50 IU of rIL-2/ml was added. Half of the medium was removed and replaced with fresh medium every three days. The cells were restimulated weekly for six weeks with PASD1 peptides before being used in an ELISPOT assay. In some experiments, CD8-positive T cells were enriched from the CTL lines using magnetic beads coated with anti-human CD8 antibody or CD4-positive T cells were enriched from the $T_H$ cell lines using magnetic beads coated with the anti-human CD4 antibody according to manufacturer's instructions (Dynabeads, Dynal, Oslo, Norway), before assay. In other experiments, the anti-HLA-A*0201 antibody (BB7.2) was added at a concentration of 10 µg/ml to block the γ-IFN release in CTL lines while anti-HLA-DR-specific antibody (WR18) was added to the $T_H$ cell lines. The remaining cells were tested in a cytolytic assay.

Cytolytic Assays

A conventional $^{51}$Cr-labelling release assay was used to investigate the ability of CTL and $T_H$ cell lines generated from DLBCL patients to lyse PASD1-positive tumour target cells. The target cell lines, consisting of the OCI-Ly3, SUDHL-6, KM-H2 and Thiel, were radiolabelled with 100 µCi $^{51}$Cr for 90 minutes. After washing, the target cells were added to the CTL lines (at effector:target ratios of 1:3, 1:5 and 1:10) in 96-well microplates and incubated for 4 hours at 37° C. in a humidified atmosphere in 5% $CO_2$. The incubation period of the $T_H$ with the target cells was increased to 18 hours. Maximum $^{51}$Cr release was determined following the addition of 10% Triton-X to the radiolabelled target cells and spontaneous release was assessed by adding RPMI1640/FCS to the target cells. The supernatant was harvested and counted in a gamma-counter (Beckmann, Heidelberg, Germany). The percentage of specific lysis was calculated as follows: (experimental cpm−spontaneous cpm)/(maximum cpm−spontaneous cpm)×100.

Immunoperoxidase Labeling Studies

Paraffin embedded tissue sections were dewaxed and antigen retrieval was carried out in 50 mM Tris: 2 mM EDTA at pH 9.0 as previously described (Pulford et al 2006). PASD1 protein expression was detected after overnight incubation using the antibodies PASD1-1 (diluted 1:50) and PASD1-2 (diluted 1:25) and the Mach Three detection kit following the manufacturer's instructions. Subtyping of the DLBCL cases was performed using antibodies to MUM1, BCL6 and CD10 and the Envision detection system. Cases were identified as being of germinal center (GCB) or non-germinal center (NGC) origin according to Hans et al 2004).

Statistical Analysis

The student's t-test was used to analyze the results obtained in the ELISPOT and cytolytic assays.

Results

The current study was performed in order to detect the presence of a CTL and $T_H$ cell responses to PASD1 peptides that would highlight PASD1 as a potential candidate for vaccine development in DLBCL. PASD1(1), PASD1(2), PASD1(3), PASD1(4) and PASD1(5) peptides were used to study the CTL response while peptides PASD1(6), PASD1(7), PASD1(8), PASD1(9) and PASD1(10) peptides were used to investigate the presence of a $T_H$ response. In a series of experiments the efficacy of peptides PASD1(6) and PASD1(7) to induce a CTL response was also investigated. In these cases cells cultured with PASD1(6) or PASD1(7) peptides for 8-10 days were tested in an ELISPOT assay for a γ-IFN release to the PASD1(1) CTL peptide.

γ-IFN Release Assay to PASD1 Peptides (PASD1(1) to PASD1(5))

The results of the gamma-interferon (γ-IFN) response ELISPOT assay relating to PASD1(1) to (5) are summarized in Table 2. We have confirmed the presence of a significant γ-IFN response in 21/28 (71%) HLA-A*0201-positive DLBCL patients after short-term culture with PASD1 peptides compared to those results obtained from the control cultures (cells stimulated with the irrelevant HIV peptide or medium only, p<0.05). Of these, 18 patients developed DLBCL de novo while in 2 patients the DLBCL developed via transformation of their follicular lymphoma and 1 patient had T-cell rich DLBCL. Thirteen patients responded to 2 or more peptides and of these, 2 patients responded to all five peptides, 1 patient to 4 peptides and 5 patients to 3 peptides. In contrast, no significant γ-IFN responses were obtained from the HLA-A*0201-negative patients with either de novo (n=10) or transformed (n=8) DLBCL or T-cell rich B-cell lymphoma (n=2) (data not shown). Furthermore, none of the PBMCs obtained from the 4 HLA-A*0201-positive and 2 HLA-A*0201-negative healthy subjects recognized the PASD1 peptides. The frequencies of PASD1-responding T cells varied between patients, ranging from 1:600 PBMCs in patient 1 to 1:2000 in patient 2. It is noteworthy that of those patients who were able to recognize the PASD1 peptides 13 achieved complete remission, 6 are currently in partial remission while 2 patients have died. This is in contrast to the situation with the 7 HLA-A*0201-positive patients who were unable to recognize PASD1 peptides; only 1 achieved complete remission, 2 are in partial remission and 4 have died during the course of this study.

TABLE 2

Summary of the γ-IFN release by DLBCL patients to PASD1 peptides predicted to be immunogenic in the context of HLA-A*0201.

| Patient | DLBCL | Sub-type | HLA-A*0201 | Reactivity with antibody: PASD1-1 | PASD1-2 | γ-IFN response to peptides PASD1 (1) | PASD1 (2) | PASD1 (3) | PASD1 (4) | PASD1 (5) | No Peptide | HIV-1 | PHA |
|---|---|---|---|---|---|---|---|---|---|---|---|---|---|
| Significant response | | | | | | | | | | | | | |
| 1 | De novo | NGC | + | 50% +/- | - | ░ | ░ | ░ | ░ | ░ | 12 ± 2 | 14 ± 4 | 96 ± 18 |
| 2 | De novo | GCB | + | - | - | ░ | ░ | ░ | ░ | ░ | 8 ± 2 | 8 ± 2 | 72 ± 12 |
| 3 | De novo | CD10- | + | + + | +/- * | ░ | ░ | 24 ± 4 | ░ | ░ | 8 ± 2 | 8 ± 2 | 72 ± 12 |
| 4 | De novo | NGC | + | +<50%, *, # | - | ░ | ░ | ░ | 38 ± 8 | 12 ± 4 | 10 ± 2 | 14 ± 6 | 52 ± 12 |
| 5 | De novo | NGC | + | NA | NA | ░ | ░ | 24 ± 4 | 30 ± 4 | ░ | 10 ± 2 | 12 ± 2 | 82 ± 12 |
| 6 | De novo | NGC | + | NA | NA | ░ | 34 ± 8 | ░ | ░ | 28 ± 4 | 14 ± 4 | 12 ± 2 | 78 ± 18 |
| 7 | De novo | GCB | + | NA | NA | ░ | 28 ± 4 | ░ | ░ | 28 ± 4 | 10 ± 2 | 12 ± 2 | 54 ± 8 |
| 8 | De novo | GCB | + | +/-, * | * | ░ | 24 ± 4 | ░ | 16 ± 4 | 18 ± 4 | 10 ± 2 | 12 ± 2 | 58 ± 10 |
| 9 | De novo | GCB | + | +/-, * | +/-, * | ░ | ░ | 18 ± 2 | 30 ± 6 | 28 ± 4 | 12 ± 2 | 10 ± 2 | 42 ± 10 |
| 10 | Relapse | GCB | + | * | +/- * | ░ | 28 ± 2 | ░ | 18 ± 4 | 22 ± 4 | 8 ± 2 | 10 ± 4 | 48 ± 10 |
| 11 | De novo | GCB | + | + | +/- | ░ | 32 ± 6 | ░ | 30 ± 4 | 28 ± 2 | 12 ± 2 | 14 ± 4 | 86 ± 12 |
| 12 | De novo | GCB | + | + | * | 25 ± 16 | 22 ± 2 | 26 ± 4 | 28 ± 2 | ░ | 10 ± 4 | 12 ± 2 | 86 ± 10 |
| 13 | De novo | GCB | + | - | - | 30 ± 4 | 26 ± 4 | 22 ± 6 | 26 ± 4 | ░ | 8 ± 2 | 14 ± 2 | 74 ± 8 |
| 14 | De novo | NGC | + | - | +/- | ░ | 28 ± 2 | 32 ± 8 | 34 ± 8 | 36 ± 2 | 14 ± 4 | 16 ± 2 | 108 ± 14 |
| 15 | De novo | NGC | + | +, * | * | 18 ± 4 | 24 ± 6 | 22 ± 2 | 32 ± 4 | ░ | 12 ± 2 | 16 ± 4 | 128 ± 24 |
| 16 | De novo | GCB | + | NA | NA | 12 ± 2 | 14 ± 4 | 22 ± 4 | 26 ± 2 | ░ | 10 ± 2 | 12 ± 4 | 58 ± 6 |
| 17 | De novo | GCB | + | - | - | 36 ± 6 | 30 ± 4 | 34 ± 6 | ░ | 28 ± 4 | 10 ± 2 | 14 ± 2 | 86 ± 8 |
| 18 | Relapse | NGC | + | - + | - | 36 ± 6 | 42 ± 4 | 28 ± 4 | 20 ± 4 | 32 ± 8 | 16 ± 4 | 12 ± 4 | 54 ± 8 |
| 37 | Trans | - | + | +/-, * | * | ░ | ░ | ░ | 12 ± 2 | 26 ± 4 | 10 ± 2 | 12 ± 4 | 108 ± 16 |
| 38 | Trans | - | + | NA | NA | ░ | 24 ± 4 | 18 ± 2 | 28 ± 6 | 26 ± 4 | 12 ± 4 | 14 ± 2 | 100 ± 12 |
| 48 | TCR | - | + | + +, # | +/- * | ░ | ░ | 36 ± 8 | ░ | 22 ± 4 | 12 ± 4 | 10 ± 4 | 92 ± 18 |

TABLE 2-continued

Summary of the γ-IFN release by DLBCL patients to PASD1 peptides predicted to be immunogenic in the context of HLA-A*0201.

| | No Significant response | | | | | | | | | | | | | |
|---|---|---|---|---|---|---|---|---|---|---|---|---|---|---|
| 19 | De novo | NGC | + | - | - | 32±4 | 20±6 | 22±6 | 28±2 | ND | 12±4 | 8±6 | 44±8 |
| 20 | De novo | NGC | + | - | - | 28±4 | 34±10 | 18±2 | 38±8 | 22±6 | 14±2 | 10±4 | 54±12 |
| 21 | De novo | GCB | + | - | - | 20±4 | 16±2 | 18±2 | 22±4 | 12±2 | 8±2 | 10±2 | 38±6 |
| 21 | De novo | GCB | + | +,* | * | 32±8 | 34±6 | 18±4 | 28±4 | 16±2 | 12±2 | 14±4 | 76±16 |
| 23 | De novo | NGC | + | + | - | 18±2 | 12±4 | 16±2 | 10±4 | 12±2 | 14±2 | 10±2 | 36±4 |
| 24 | De novo | NGC | + | + | - | 26±4 | 24±2 | 18±2 | 16±4 | 22±4 | 8±2 | 10±4 | 52±8 |
| 39 | Trans | - | + | - | - | 28±4 | 22±2 | 12±2 | 8±4 | 18±4 | 12±2 | 14±4 | 42±8 |
| HD 1 | | - | + | | | 22±4 | 18±2 | 20±2 | 14±4 | 16±2 | 12±2 | 14±6 | 48±8 |
| HD 2 | | - | + | | | 18±2 | 10±2 | 16±2 | 12±2 | 22±4 | 8±2 | 10±2 | 62±14 |
| HD 3 | | - | + | | | 8±1 | 6±2 | 10±2 | 12±2 | 12±2 | 8±2 | 10±2 | 78±10 |
| HD 4 | | - | + | | | 22±0 | 12±0 | 14±1 | 6±2 | 12±2 | 8±2 | 10±2 | 112±14 |
| HD 5 | | - | - | | | 18±2 | 14±1 | 10±1 | 16±2 | 18±2 | 10±1 | 8±2 | 56±10 |
| HD 6 | | - | - | | | 22±2 | 24±2 | 26±2 | 28±4 | 24±2 | 16±4 | 12±2 | 76±8 |

GCB - Germinal center derived;
NGC - Non-germinal center-derived;
+/−, + and ++ denotes intensity of cytoplasmic labelling;
* denotes nuclear labelling from 5-30% of tumor cells;
# denotes labelling of some smaller lymphocytes and vessels in tumour;
NA - Tissue not available;
Underlining denotes significant γ-IFN response.
The results ± are from triplicate ELISPOT cultures. The SD was calculated using standard techniques.
∞ Biopsy from time of relapse.

The results from the γ-IFN release assay permitted the PASD1 peptides to be listed in the following order of immunogenicity for eliciting CTLs: PASD1(1), PASD1(2), PASD1(5), PASD1(3) and PASD1(4) with PASD1(1) being the most immunogenic. Subsequent studies on the CTL response have thus focused on the more immunogenic PASD1(1), PASD1(2) and PASD1(5) peptides. PASD1(1), PASD1(2), PASD1(3) and PASD1(4) lie within the region common to both PASD1a and PASD1b isoforms whilst PASD1(5) is within the unique C-terminus of PASD1b.

Persistence of the γ-IFN CTL Response to PASD1.

Figure 2A:
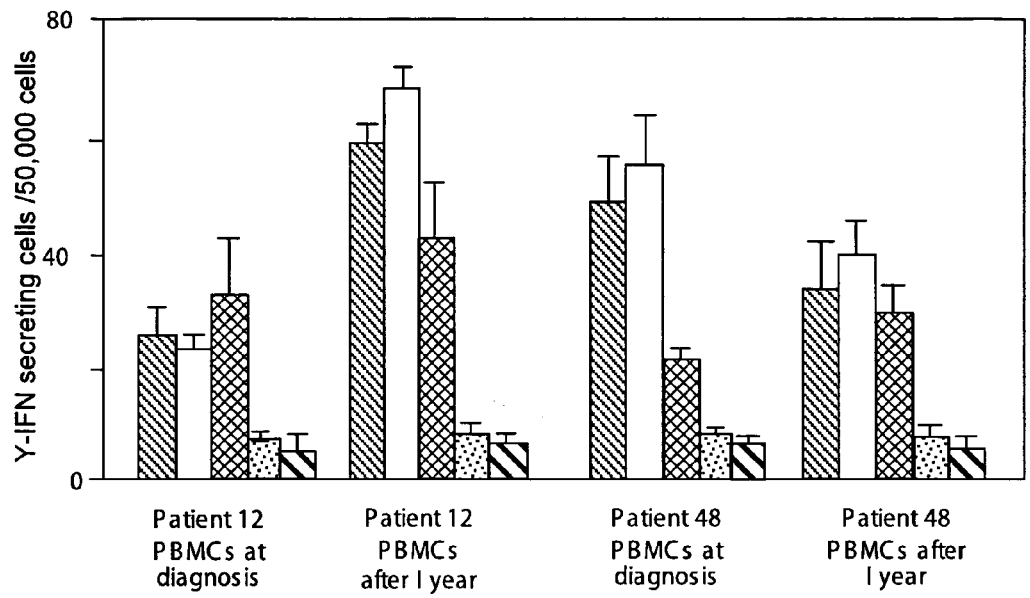

Blood was collected from 3 HLA-A*0201-positive patients, two with de novo DLBCL (patients 1 and 12) and one patient with T-cell rich DLBCL (patient 48) on their return to clinic one year after initial diagnosis. A γ-IFN response to PASD1 peptides following short-term culture was detected in all three DLBCL patients after one year in remission. Results from two patients are shown in FIG. 2a. This response suggested the presence of a pool of memory T cells to the PASD1 protein. Although the response was maintained in both patients, a differential can be seen with the intensity of the response of patient 12 increasing, but that of patient 48 decreasing.

Generation of CTL Lines Specific for PASD1 Peptides.

Figure 2B:
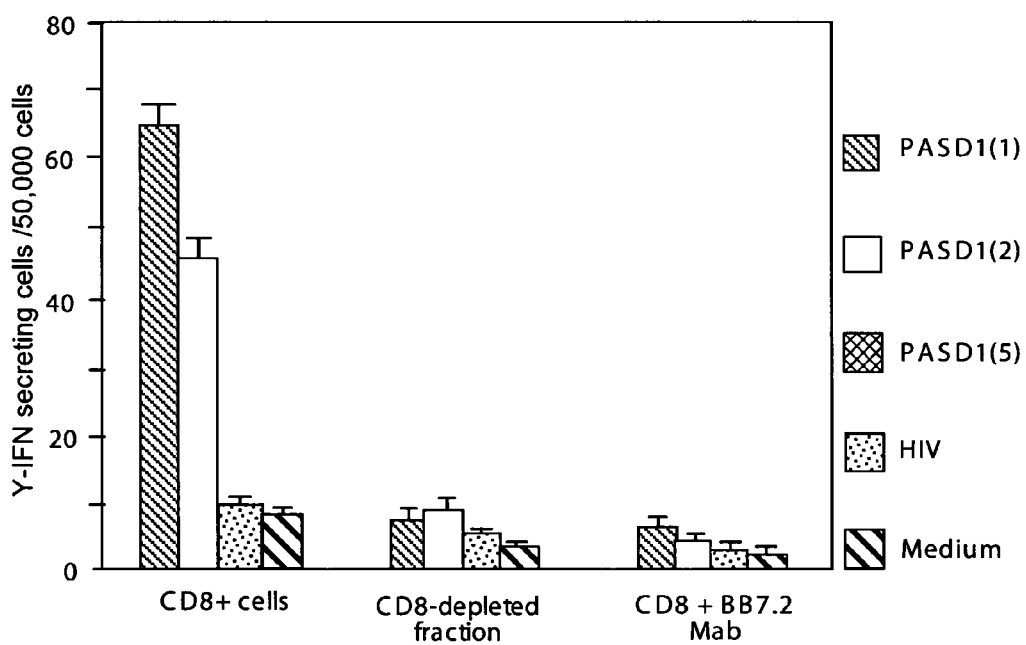
Figure 3A:
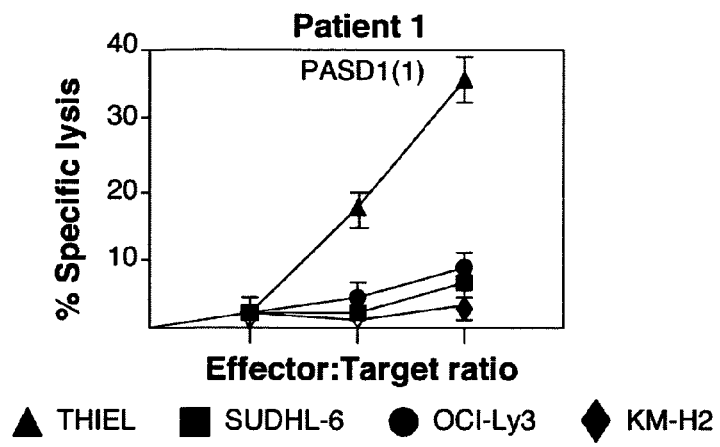
Figure 3B:
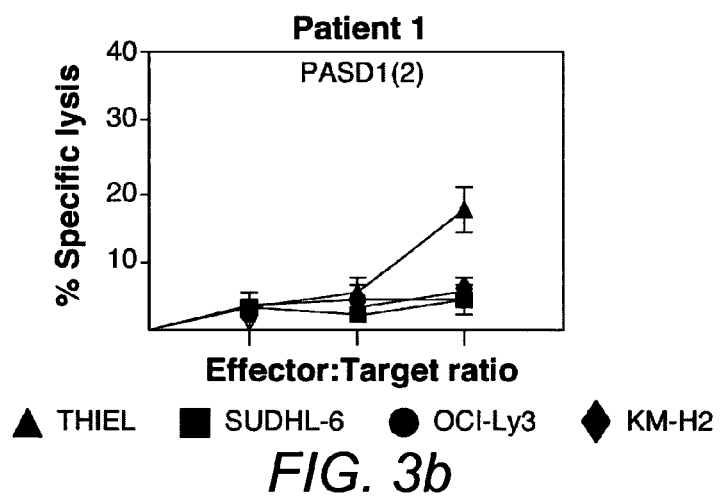
Figure 3C:
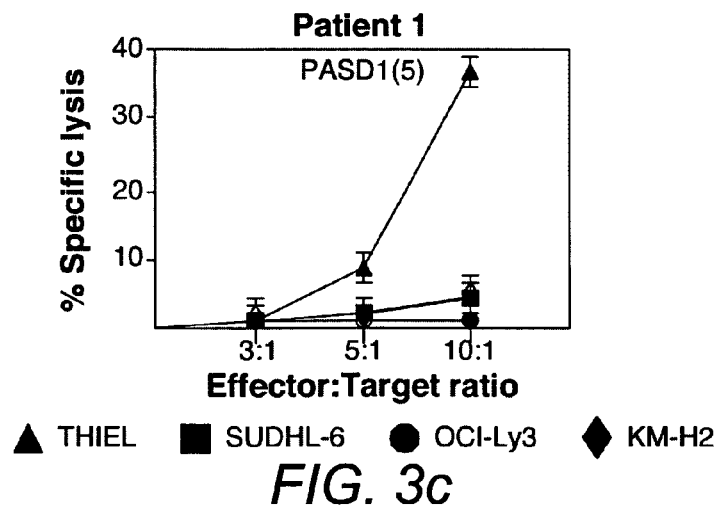
Figure 3D:
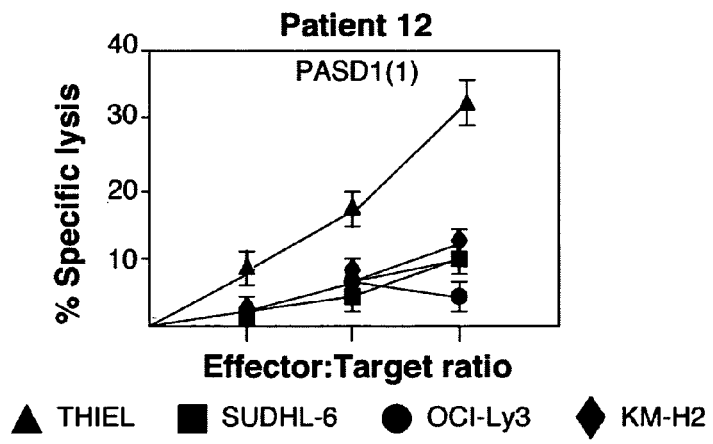
Figure 3E:
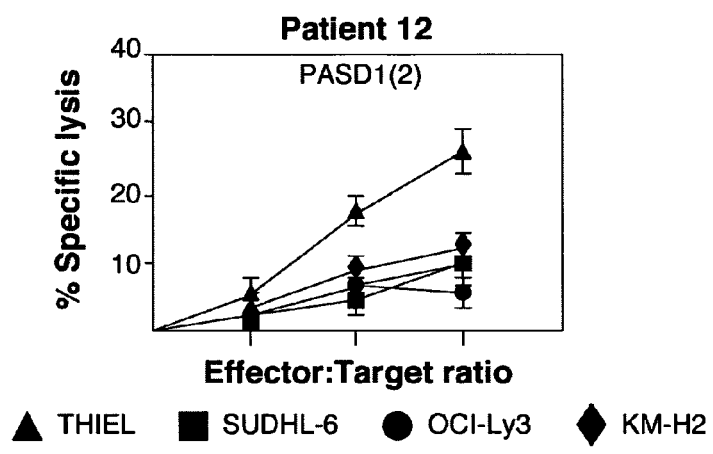
Figure 3F:
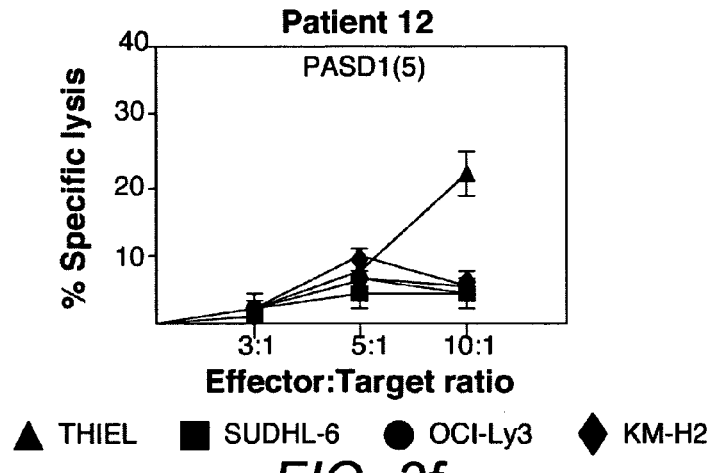
Figure 3G:
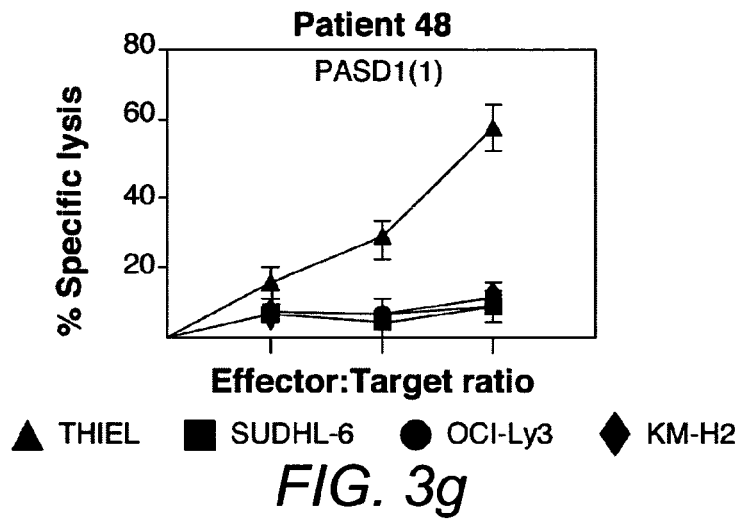
Figure 3H:
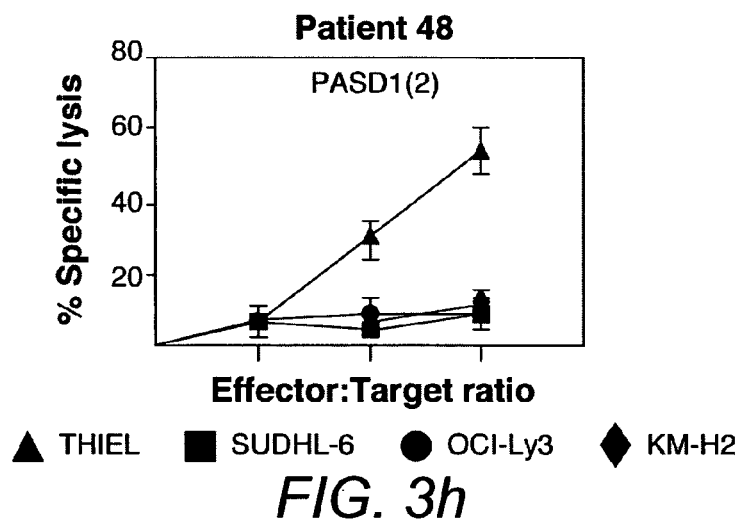
Figure 3I:
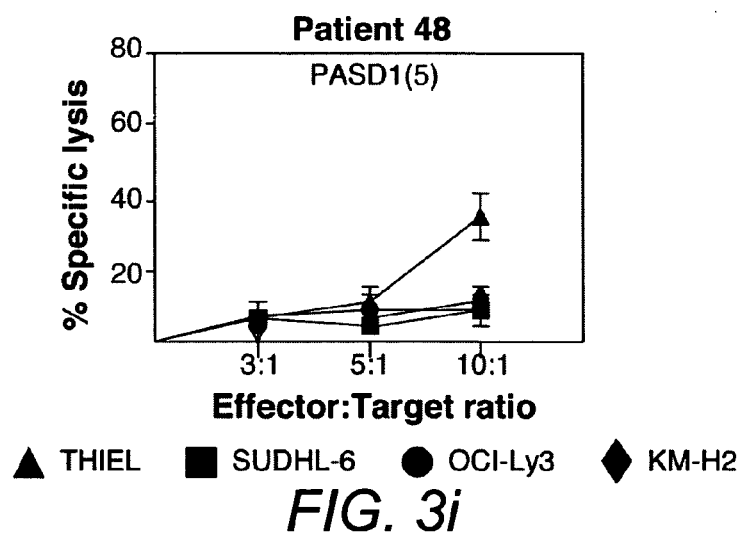

PASD1-stimulated CTL lines from four HLA-A*0201-positive patients (3 with de novo DLBCL and one with T-cell rich DLBCL) were maintained in long-term culture to permit further analysis of their functional ability. PBMCs were re-stimulated weekly with rIL-2 and with one of the following: PASD1(1), PASD1(2), or PASD1(5) or the irrelevant HIV peptide. After six weeks, the cell lines were tested for their γ-IFN secreting activity to the PASD1 and control peptides in an overnight ELISPOT assay. The CTL cell lines demonstrated a γ-IFN response to the PASD1 peptides which was abrogated by the removal of CD8-positive T cells or the addition of the anti-HLA-A*0201 monoclonal antibody BB7.2 (FIG. 2b). These results demonstrate the CD8-positive MHC Class I restricted nature of the response.

Cytolytic Activity of the CTL Lines

Although the CTL cell lines can recognize the stimulating PASD1 peptides, it is possible that the cells may not recognize naturally presented peptides. Therefore, the ability of the CD8-positive CTL lines specific for PASD1(1), PASD1(2) and PASD1(5) to recognize and lyse tumor cells expressing endogenous PASD1 protein was tested in a standard $^{51}$Cr release assay. The CTL lines from four patients raised against the PASD1(1), PASD1(2) and PASD1(5) peptides demonstrated a dose dependent lysis of the HLA-A*0201-positive PASD1-positive Thiel cell line but not the PASD1-negative SUDHL-6 HLA-A*0201-negative or PASD1-positive OCI-Ly3 (DLBCL) or HLA-A*0201-negative PASD1-positive KM-H2 cell lines. The cytolytic effect was significant even at an effector:target ratio of 5:1 using cells stimulated with PASD1(1) peptide in all four patients. The results obtained from three patients are shown in FIG. 3.

Immunoperoxidase Labeling of DLBCL

Results obtained from the DLBCL subtyping and PASD1 immunolabelling studies of tumour biopsies from patients are summarized in Tables 2 and 3. Tissue sections from diagnostic biopsies were available for 16 of the patients who mounted a significant γ-IFN response to PASD1 peptides. Labelling with the PASD1 antibodies was detected in the tumour cells of 13 of these patients. Examples of results are shown in FIG. 4. Moderate to strong labelling of the cytoplasm of the tumour cells was observed in 8 patients using antibody PASD1-1 (recognizing an epitope common to both PASD1 isoforms), while weaker labelling was present in 4 other cases. Nuclear labelling of a small number of tumour cells was also seen in biopsies from 5 patients using this reagent. Antibody PASD1-2 (recognizing the unique region of PASD1b) stained either a subpopulation of nuclei or weakly labelled the cytoplasm of the tumour cells in 10 cases of DLBCL. Labelling using the PASD1-1 and PASD1-2 antibodies was also observed in 8 patients whose cells did not mount a γ-IFN response. In addition to the tumour cells, occasional smaller lymphoid cells and vessels were also labelled by antibody PASD1-1 in a case of de novo DLBCL and a case of T-cell rich DLBCL.

γ-IFN Release Assay to PASD1(6) to PASD1(10) Peptides

The results of the γ-IFN response ELISPOT assay relating to PASD1 peptides (6) to (10) are summarized in Table 3.

$T_H$ responses were examined in peripheral blood lymphocytes of 19 DLBCL patients and five healthy individuals. As shown in Table 3, 10 patients expressing the PASD1 protein exhibited a significant γ-IFN response to at least one of the five peptides after short-term culture with the PASD1 peptides compared to the control cultures ($p<0.05$). Of these, 8 were patients with de novo DLBCL, one had transformed DLBCL and the remaining patient had T-cell rich DLBCL. No significant response to any of the peptides was detected in either the PASD1-negative patients or the healthy donors. It is of interest that while some patients, eg patients 10 and 15, were able to mount a γ-IFN response to some of the CTL peptides (Table 2). These patients and patients 21 and 61 whose tumour cells were PASD1-positive, failed to mount a significant response to any of the five peptides PASD1(6) to PASD1(10).

TABLE 3

Summary of the $T_H$ immune response by DLBCL patients and normal donors to the PASD1 peptides

| Patient number | DLBCL | Sub-type | MHC class II | Reactivity with antibody: PASD1-1 | PASD1-2 | γ-IFN response to peptides PASD1 (6) | PASD1 (7) |
|---|---|---|---|---|---|---|---|
| Significant response ||||||||
| 1 | De novo | NGC | DRB1-0102 | 50%+/− | − | 52 ± 6 | 28 ± 4 |
| 2 | De novo | GCB | DRB1-0101 | − | − | 32 ± 4 | 46 ± 8 |
| 3 | De novo | CD10- | DRB1-0301 | ++ | +/− * | 34 ± 4 | 26 ± 4 |
| 4 | De novo | NGC | DRB1-0102 | +<50%, *, # | − | 58 ± 8 | 44 ± 4 |
| 8 | De novo | GCB | DRB1-1501 | +/−, * | * | 36 ± 6 | 18 ± 2 |
| 9 | De novo | GCB | DRB1-0301 | +/−, * | +/−, * | 22 ± 6 | 18 ± 2 |
| 12 | De novo | GCB | DRB1-0401 | + | * | 44 ± 6 | 36 ± 4 |
| 24 | De novo | NGC | DRB1-1301 | + | − | 22 ± 4 | 38 ± 4 |
| 37 | Trans | — | DRB1-0103 | +/−, * | * | 38 ± 4 | 32 ± 6 |
| 48 | T-cell rich | — | DRB1-0301 | ++. # | +/− * | 48 ± 4 | 56 ± 6 |
| No significant response ||||||||
| 10 | De novo | GCB | DRB1-0101 | * | +/− * | 30 ± 8 | 26 ± 2 |
| 15 | De novo | NGC | DRB1-1301 | +, * | * | 28 ± 4 | 32 ± 2 |
| 17 | De novo | GCB | DRB1-0301 | − | − | 20 ± 2 | 18 ± 4 |
| 18 | De novo | NGC | DRB1-0401 | − | − | 14 ± 2 | 26 ± 2 |
| 19 | De novo | NGC | DRB1-1104 | − | − | 22 ± 2 | 26 ± 2 |
| 20 | De novo | GCB | DRB1-1303 | − | − | 10 ± 2 | 14 ± 2 |
| 21 | De novo | GCB | DRB1-0301 | +, * | − | 18 ± 2 | 10 ± 2 |
| 28 | Trans | — | DRB1-0701 | − | − | 28 ± 4 | 22 ± 6 |
| 61 | De novo | NGC | DRB1-0401 | + | − | 22 ± 2 | 10 ± 4 |
| Healthy Donors ||||||||
| HD 1 | | — | DRB1-0102 | | | 14 ± 2 | 20 ± 2 |
| HD 2 | | — | DRB1-0401 | | | 10 ± 2 | 8 ± 2 |
| HD 3 | | — | DRB1-0401 | | | 5 ± 2 | 10 ± 2 |
| HD 4 | | — | DRB1-0301 | | | 14 ± 2 | 20 ± 2 |
| HD 5 | | — | DRB1-0301 | | | 24 ± 2 | 22 ± 2 |

| Patient number | PASD (8) | PASD1 (9) | PASD1 (10) | None | HIV-1 | PHA |
|---|---|---|---|---|---|---|
| Significant response |||||||
| 1 | 32 ± 3 | 30 ± 2 | 40 ± 2 | 10 ± 4 | 2 ± 1 | 98 ± 15 |
| 2 | 36 ± 6 | 24 ± 2 | 40 ± 4 | 14 ± 2 | 16 ± 2 | 106 ± 18 |
| 3 | 18 ± 2 | 24 ± 2 | 32 ± 2 | 10 ± 2 | 8 ± 2 | 62 ± 8 |
| 4 | 28 ± 4 | 18 ± 2 | 32 ± 4 | 16 ± 2 | 14 ± 2 | 98 ± 14 |
| 8 | 20 ± 4 | 18 ± 2 | 18 ± 4 | 10 ± 2 | 12 ± 4 | 48 ± 4 |
| 9 | 12 ± 3 | 20 ± 2 | 14 ± 2 | 8 ± 2 | 4 ± 2 | 118 ± 18 |
| 12 | 24 ± 4 | 20 ± 4 | 32 ± 4 | 14 ± 2 | 12 ± 2 | 72 ± 10 |
| 24 | 28 ± 4 | 26 ± 4 | 16 ± 4 | 14 ± 4 | 8 ± 2 | 86 ± 14 |
| 37 | 16 ± 2 | 28 ± 2 | 34 ± 2 | 10 ± 2 | 16 ± 2 | 126 ± 22 |
| 48 | 40 ± 6 | 26 ± 2 | 38 ± 2 | 14 ± 2 | 12 ± 2 | 84 ± 10 |

TABLE 3-continued

Summary of the $T_H$ immune response by DLBCL patients
and normal donors to the PASD1 peptides

| | No significant response | | | | | |
|---|---|---|---|---|---|---|
| 10 | 36 ± 4 | 10 ± 2 | 32 ± 2 | 14 ± 2 | 16 ± 4 | 78 ± 8 |
| 15 | 10 ± 1 | 8 ± 2 | 18 ± 4 | 12 ± 4 | 14 ± 4 | 58 ± 6 |
| 17 | 14 ± 2 | 8 ± 2 | 10 ± 4 | 12 ± 2 | 10 ± 2 | 54 ± 12 |
| 18 | 20 ± 2 | 24 ± 2 | 22 ± 2 | 16 ± 2 | 14 ± 2 | 62 ± 12 |
| 19 | 24 ± 2 | 18 ± 2 | 12 ± 2 | 16 ± 2 | 12 ± 2 | 58 ± 14 |
| 20 | 18 ± 2 | 8 ± 2 | 16 ± 2 | 12 ± 2 | 10 ± 2 | 52 ± 10 |
| 21 | 14 ± 2 | 16 ± 2 | 18 ± 2 | 8 ± 2 | 10 ± 2 | 102 ± 10 |
| 28 | 16 ± 2 | 22 ± 4 | 10 ± 2 | 14 ± 1 | 6 ± 2 | 45 ± 8 |
| 61 | 12 ± 2 | 16 ± 2 | 6 ± 2 | 8 ± 1 | 12 ± 2 | 58 ± 10 |
| | Healthy Donors | | | | | |
| HD 1 | 18 ± 2 | 14 ± 2 | 10 ± 2 | 10 ± 2 | 8 ± 2 | 86 ± 14 |
| HD 2 | 10 ± 2 | 1 ± 1 | 4 ± 2 | 4 ± 2 | 6 ± 2 | 66 ± 10 |
| HD 3 | 6 ± 2 | 8 ± 2 | 2 ± 1 | 4 ± 2 | 1 ± 1 | 46 ± 6 |
| HD 4 | 10 ± 2 | 19 ± 2 | 18 ± 2 | 8 ± 2 | 10 ± 2 | 74 ± 16 |
| HD 5 | 10 ± 2 | 18 ± 2 | 16 ± 2 | 12 ± 2 | 8 ± 2 | 63 ± 10 |

GCB—Germinal center derived;
NGC—Non-germinal center-derived.
+/−, + and ++ denotes intensity of cytoplasmic labelling
* denotes nuclear labelling from 5-30%
# denotes labelling of some smaller lymphocytes and vessels in tumour
NA—Tissue not available.
The results +/− are from triplicate ELISPOT cultures. The SD was calculated using standard techniques.

Patients responded differently to the PASD1 peptides. The frequencies of PASD1-responding T cells varied among patients, ranging from 1:900 PBMCs in Patient 4 to 1:2000 in Patient 3. It is noteworthy that the PASD1(6)$_{31-50}$ peptide (SEQ ID No 6) and PASD1(7)$_{42-61}$ (SEQ ID No 7) encompassing the PASD1(1)$_{39-48}$ epitope (SEQ ID No. 1) are immunogenic in the majority of patients studied here. Both PASD1 (6) and PASD1(7) peptides were also able to elicit a comparable γ-IFN response to the PASD1(1) CTL peptide (SEQ ID No.1) (Table 4). These results indicate that the PASD1(1) epitope when included in either PASD1(6) or PASD1(7) is processed correctly to retain its immunogenicity as a CTL epitope.

TABLE 4

Comparison of the γ-IFN response to the PASD1(1), PASD1(6) and
PASD1(7) peptides by peripheral blood mononuclear cells from a DLBCL
patient stimulated in culture with PASD1(6) or PASD1(7) peptides.

| γ-IFN response to peptides | | | | | |
|---|---|---|---|---|---|
| PASD1(1) | PASD1(6) | PASD1(7) | Medium only | Irrelevant peptide | PHA |
| 30 +/− 4 | 32 +/− 2 | 26 +/− 2 | 10 +/− 2 | 8 +/− 2 | 48 +/− 2 |

The results +/− are from triplicate ELISPOT cultures.
The SD was calculated using standard techniques.

The results from the γ-IFN release assay permitted the PASD1 peptides to be listed in the following order of immunogenicity for eliciting $T_H$ cell responses: PASD1(6), PASD1(7), PASD1(10), PASD1(9) an PASD1(8) with PASD1(6) and PASD1(7) being the most immunogenic. Subsequent studies on the $T_H$ cell response have thus focussed on the more immunogenic PAS1(6) and PASD1(7) peptides both of which lie within the region common to both PASD1a and PASD1b. These results also demonstrate the presence, within PASD1, of numerous promiscuous MHC Class II epitopes; a situation previously reported for other CTAs such as NY-ESO-1 (Mandic et al 2003). The presence of such epitopes, recognisable in the context of a variety of different MHC Class II molecules, expands the population of patients in which the peptides could be used.

Persistence of the $T_H$ γ-IFN Response to PASD1.

Blood was collected from 1 patient with de novo DLBCL (patient 12) and one patient with T-cell rich DLBCL (patient 48) on their return to clinic one year after initial diagnosis. A γ-IFN response to PASD1 peptides following short-term culture was detected in all three DLBCL patients after one year in remission. Results from two patients are shown in FIG. 5a. This response suggested the presence of a pool of memory T cells to the PASD1 protein.

The $T_H$ responses in two DLBCL patients (patients 10 and 12) at time of diagnosis and one year post-diagnosis (see FIG. 5b). In both instances, a significant γ-IFN response to the two PASD1 peptides PASD1(6) and PASD1(7) was sustained after one year post-diagnosis. This infers the presence of circulating memory $T_H$ cell populations able to recognise the PASD1 protein.

Generation of $T_H$ Lines Specific for PASD1 Peptides.

PASD1-stimulated $T_H$ lines from a patient with de novo DLBCL (Patient 1) and one patient with T-cell rich DLBCL (patient 48) were maintained in long-term culture to permit further analysis of their functional ability. PBMCs were re-stimulated weekly with rIL-2 and with one of the following: PASD1(6), or PASD1(7) or the irrelevant HIV peptide. After six weeks, the cell lines were tested for their γ-IFN secreting activity to the PASD1 and control peptides in an overnight ELISPOT assay. The cell lines demonstrated a γ-IFN response to the PASD1 peptides that was abrogated by the removal of CD4-positive T cells (FIG. 5a) or the addition of the anti-HLA-DR monoclonal antibody WR18 (FIG. 5b). These results demonstrate the CD4-positive MHC Class II restricted nature of the response.

Cytolytic Activity of the $T_H$ Cell Lines

Although the $T_H$ cell lines can recognize the stimulating PASD1 peptides, it is possible that these cell lines are incapable of recognizing naturally presented peptides. The ability of $T_H$ lines (raised from Patients 1 and 48) specific for PASD1 (6) and PASD1(7) to recognize and lyse tumor cells expressing endogenous PASD1 protein was tested in a $^{51}$Cr release assay. The $T_H$ cell lines from these patients demonstrated a dose dependent lysis not only of the PASD1-positive Thiel but also of the PASD1-positive OCI-Ly3 cell lines. This was despite the fact that the PASD1-positive cell lines express different HLA-DRB1 alleles thus further demonstrating the promiscuity of the HLA-DR epitopes chosen. (It is notable that the lysis of the OCI-Ly3 observed here with the $T_H$ cells was not observed with the CTL lines, a finding in keeping with the lack of the correct MHC Class I allele on OCI-Ly3). No lysis was detected of the PASD1-negative cell line SUDHL-6 despite the fact that this cell line expressed a relevant MHC Class II allele (FIG. 6, P<0.001).

Discussion

This example describes the presence of circulating functional CTLs and $T_H$ cells to PASD1 peptides in patients with either de novo, transformed or T-cell rich DLBCL thus providing experimental validation of PASD1 peptides as potential vaccine candidates that are recognized by a T-cell response in patients' with B-cell tumours. The potential of PASD1 as an immunotherapeutic target was further supported by a study reporting that PASD1 not only represented a SEREX antigen in acute myeloid leukemia but also that PASD1 mRNA elicited a proliferative CD4-positive T-cell response in normal subjects (Guinn et al 2005).

CTLs recognizing PASD1 peptides were detected after short-term culture in 71% of HLA-A*0201-positive DLBCL patients while $T_H$ cells recognizing PASD1 peptides were detected after short-term culture in 12/19 (63%) of DLBCL patients with relevant MHC Class II alleles. This result is suggestive of the presence of circulating PASD1-specific cells in the DLBCL patients. Such spontaneous immunity to CTAs, including NY-ESO-1, SP17 and MAGE-A3, has been previously reported in multiple myeloma (Chiriva-Internati et al 2002, van Rhee et al 2005, Goodyear et al 2005, Goodyear et al 2008, Jackson et al 2006). The presence of CTLs recognizing CTAs has also been reported in patients following allogenic transplantation (Atanackovic et al 2007) and provides support for the use of CTAs as immunotherapeutic targets. The percentage of T-cells recognising PASD1 after short-term culture varied from 0.16% to 0.05%, comparing favourably with the results obtained for NY-ESO-1, MAGE-A(1-4), MAGE-A3, LAGE-1 and NY-ESO-1 in haematological and non-haematological malignancies (van Rhee et al 2005, Goodyear et al 2005, Jager et al 2000, Inokuma et al 2007).

Correlations have been reported between antibody responses and prognosis in myeloma (van Rhee et al 2005, Goodyear et al 2005). Despite our previous finding that antibody responses to PASD1 were detected only in patients with poor prognosis DLBCL identified through immunolabelling techniques (Liggins et al 2004a, Liggins et al 2004b), a γ-IFN response to PASD1 peptides was detected in 10 patients with GCB-derived DLBCL in addition to the 12 patients with poor-prognosis DLBCL (8 with NGC-derived DLBCL and 4 patients with transformed DLBCL, results obtained from Tables 2 and 3), suggesting that PASD1 may be applicable as a therapeutic target regardless of DLBCL subtype. It is also of interest that T-cell rich DLBCL, representing a variant of DLBCL with an aggressive outcome (Jaffe et al., 2001, El Weshi et al 2007) is characterised by the presence of infiltrating inflammatory cells suggestive of a 'host immune' response to the tumour (Abramson et al 2007).

A study of sequential blood samples from DLBCL patients in the present example demonstrates a CTL and $T_H$ cell response to PASD1 peptides that persisted over a 12-month period post-diagnosis. Sustained CTL responses to TAAs have been reported in myeloma (Goodyear et al 2005, Ait-Tahar et al 2006, Valmori et al 2000, Passoni et al 2006). All four DLBCL patients were still in remission by the end of this study. The persistence of the T-cell responses in these patients suggests the presence of memory T cells which might be involved in protective immunity and which also represent potential populations of T cells that could be further stimulated following vaccination (Baumgaertner et al 2006). The generation and persistence of memory CTLs and $T_H$ cells is the aim of vaccination therapies.

Since PASD1 constitutes a potential immunotherapeutic target it is important to correlate the presence of a γ-IFN response to the expression of PASD1 in tumours. Van Rhee et al. and Goodyear et al. were previously able to confirm NY-ESO-1 and MAGE proteins in those patients who mounted a CTL response to NY-ESO-1 (van Rhee et al 2005, Goodyear et al 2005). Immunohistochemical labelling with anti-PASD1 monoclonal antibodies confirmed PASD1 expression in the majority of patients (13 of the sixteen for whom biopsies were available for study had circulating CTLs and/or $T_H$ cells recognising PASD1 peptides). As previously described (Cooper et al 2006), variations in the labelling patterns of the tumour cells by the antibodies PASD1-1 and PASD1-2 recognising PASD1 isoforms were observed providing evidence for the possibility of differential expression of PASD1 isoforms in the tumour cells. Furthermore, heterogeneity of labelling was observed in the tumour cells. Intratumoural variation of CTA expression has been previously described in solid tumours (Scanlan et al 2004, Barrow et al 2006, Theurillat et al 2007) and in myeloma In addition to the presence of different CTA isoforms (Nakagawa et al 2005), possible explanations for such heterogeneity include epigenetic phenomenon such as the silencing of CTA expression through hypermethylation (Simpson et al 2005, Coral et al 2002, Sigalotti et al 2002) and post-translational modifications (Corradi et al 1997, Heidebrecht et al 2006). Increased expression of CTAs being linked to the aggressiveness of the tumours (van Rhee et al 2005, Barrow et al 2006, Dhodapkar et al 2003).

Heterogeneity in PASD1 expression may also explain the absence of labelling in the 4 cases of DLBCL in which a T-cell response was detected. Discrepancies in NY-ESO-1 expression have also been linked to the size of the tissue sections studies indicating that the presence of CTAs may vary in different regions of the tumour (Theurillat et al 2007). Only needle biopsy sections were available for two of these cases and it is possible that PASD1-positive regions of tumour were absent in the sections available for immunolabelling. It is also possible that immunolabelling may not constitute a sufficiently sensitive technique to identify low levels of PASD1 protein expression. This has been found to be the case in a study on CTA expression in haematological malignancies (paper submitted) and in breast tumours where western blotting, rather than immunolabelling techniques, was necessary to confirm CTA expression in the tumours (Sugita et al 2004). Low levels of PASD1 antigen expression may, however, not be a problem for the immune system. It has also been reported that it is the high turnover rate, rather than the presence of high or moderate levels of TAA in tumor cells, that may be important for T-cell recognition (Vierboom et al 2000).

Labelling of scattered small lymphoid cells, that were unlikely to be tumour cells, was noted in two of the PASD1-positive patients who responded to the PASD1 peptides. Although PASD1 transcripts and proteins were undetectable in normal non-reproductive tissues in previous studies (Liggins et al 2004b, Cooper et al 2006, Guinn et al 2005), PASD1 mRNA was detected in histologically normal tissues present in a matched tumour/normal expression array (Liggins et al 2004b). It is possible that PASD1 expression in these normal tissues could be due to early genetic changes occurring in the cells before morphological abnormalities become obvious.

Such a situation may explain the current result. It is also noteworthy that CTA protein expression has been reported in benign hyperplastic prostate tissue (Hudolin et al 2006).

A γ-IFN response to the PASD1 peptides PASD1(1) to (5) was not detected in those patients who were HLA-A*0201-negative even though PASD1 protein was detected in their tumour cells. The abrogation of the γ-IFN response through depletion of CD8-positive cells or the addition of an anti-MHC Class I reagent to CTL lines provided further evidence for an MHC Class I dependent PASD1 peptide response. The removal of CD4-positive cells and the addition of an anti-HLA-DR specific antibody resulted in the loss of the γ-IFN response of the $T_H$ cells confirming this response to be CD4 and MHC Class II dependent.

It was possible that the γ-IFN response of the expanded CTL and $T_H$ cell lines investigated here is limited to the recognition of the exogenous PASD1 peptides and that endogenous PASD1 peptides may not be processed appropriately by the tumor cells for recognition by the effector CTLs (Luckey et al 1998) or $T_H$ cells. However, using cell lines derived from a range of haematological malignancies, we were able to confirm that the CTL and $T_H$ cell lines raised against PASD1 peptides were able to recognise endogenously expressed PASD1 peptides and lyse PASD1-positive tumour cells in an MHC Class I and MHC Class II dependent manner respectively. The killing of target cell lines by the $T_H$ could be explained by the high degree of homology present between the DRB1 molecules and the promiscuity of the PASD1 peptides which enables them to recognise closely related DRB1 molecules (Southwood et al., 1998). $T_H$ cells expressed different HLA-BRB1 alleles. These results suggest that PASD1 might be valuable as a candidate for vaccine development. Previous studies have also demonstrated the potential of using peptide epitopes binding to both MHC Class I and Class II to achieve optimal immune responses on vaccination (Zeng 1997, Wagner et al 2003). Our results provide additional evidence to support the PASD1 peptides PASD1(6) and PASD1(7), both incorporating the PASD1(1) CTL epitope, together with their recognition by memory T-cells, as representing attractive peptides for inclusion in a vaccine formulation.

Other studies have described the presence of more than one CTA antigen in solid tumours and in haematological malignancies such as myeloma and plasmacytoma (Condomines et al 2007, Atanackovic et al 2006). The presence of more than one CTA within a tumour, combined with their loss and/or heterogeneity in their protein distribution, provides support for the inclusion of multiple CTAs in vaccine development. This approach should further maximize the eradication of the tumour cells while minimising the escape variants of the tumour (Atanackovic et al 2007, Mashino et al 2001, Jacobs et al 2007).

Previous gene expression profiling studies in DLBCL have identified the lymph node and MHC Class II signatures to be associated with improved prognosis (Rosenwald et al 2002, Rimsza et al 2004). In the case of FL, then the immune response signature of genes expressed by macrophages and T cells were linked with increased survival (Dave et al 2004) while an immunolabelling study identified the presence of FOXP3-positive T regulatory cells as being a good prognostic indicator (Carreras et al 2006). Such results suggest the immune microenvironment of the tumour cells and the infiltrating immune cells to be of importance in the outcome of these tumours.

This study is the first to define immunogenic PASD1 peptides and describe a CTL and $T_H$ response to PASD1 in DLBCL. It is also the first description of a T-cell response to a CT-X antigen in DLBCL. The current results support PASD1 as a potential immunotherapeutic target for patients with PASD1-positive DLBCL and other malignancies that express this CTA. Since tumours may express more than one CTA, the inclusion of PASD1 in a polyepitope vaccine should increase the chances of successful treatment of malignancies.

Use of PASD1 DNA Vaccines in a Pre-Clinical Transgenic Murine Model to Show Selective In Vivo Processing and Presentation of PASD1 Epitopes in Multiple Myeloma Materials and Methods Peptides The HLA-A2*0201 restricted epitopes, PASD1(1) (QLLDGFMITL) (SEQ ID No 1) and PASD1(2) (YLVGN-VCIL) (SEQ ID No 2) (Ait-Tahar, et al 2009) together with the HLA class II-restricted p30 (Fragment C-derived: FNN-FTVSFWLRVPKVSASHLE) (SEQ ID No 28) peptide were synthesized commercially and supplied at more than 95% purity (PPR Ltd, Fareham, United Kingdom).

DNA Vaccine Construction

Four vaccines were constructed as previously described (Rice, et al 2001) and are shown in FIG. 7. The first domain of the Tetanus toxin fragment C (DOM) containing the T-helper epitope p30 was fused to sequences encoding one of the following: PASD1(1), PASD1(2) or full length (FL) PASD1 to produce pDOM-PASD1(1), pDOM-PASD1(2) and pDOM-FL, respectively. p.DOM-PASD1(1) and p.DOM-PASD1(2) were obtained by polymerase chain reaction using p.DOM as template while PASD1FL was obtained by PCR using the clone PASD1_v1 (Liggins, et al 2004) as a template. The p.DOM vaccine contained the DOM1 only. The fusion genes were then inserted in pcDNA3 (Invitrogen, Paisley, United Kingdom) and their identities were confirmed by DNA sequencing and product size determined by In vitro Transcription and Translation using the TNT T7 coupled reticulocyte lysate system (Promega, Southampton, United Kingdom).

Cell Lines

The RMA-HHD cell line (mouse lymphoma cell line stably transfected with HHD, kindly provided by Dr. Lemonnier F. A., Institut Pasteur, Paris, France), KMS-12-BM (HLA-A*0201⁻ human myeloma cell line) and the YAC-1 (mouse lymphoma cell line sensitive to NK cells cytotoxic activity) cells were cultured in RPMI 1640 supplemented with 10% heat-inactivated FCS (Invitrogen Life Technologies, Paisley, U.K.), 1 mM sodium pyruvate, 2 mM L-glutamine, nonessential amino acids (1% of 100 stock) and 50 μM 2-ME. The Phoenix Amphotropic retroviral packaging cell line, kindly provided by Dr. P. Stevenson (Cambridge University, UK), were cultured in DMEM media (Lonza, Verviers, Belgium), supplemented with 10% heat-inactivated FCS, 1 mM sodium pyruvate, 2 mM L-glutamine, nonessential amino acids (1% of 100 stock). The Thiel MM-derived, Jurkat (T-ALL derived) and SUDHL6 (DLBCL-derived) cell lines were obtained as previously described (Cooper et al 2006).

Supernatant from the Phoenix Amphotropic packaging cells transiently transfected with the retroviral vector p.HH-Dmscvpuro (kindly provided by Dr Gisella Vittes) was used transduce the KMS-12-BM cell line to create KMS-12-HHD. The retroviral transfection followed the protocol from Dr. G. Nolan's laboratory (Stanford, USA), available online.

HLA-A*0201 Transgenic Mice

The HHD mouse strain expresses a transgenic chimeric monochain MHC class I molecule in which the COOH-terminus of human β2-microglobulin is covalently linked to the NH$_2$-terminus of chimeric human HLA-A2 a1 and a 2 domains fused with the murine H-2D$^b$ α3 domain (Pascolo, et al 1997). These mice lack cell-surface expression of mouse endogenous H-2$^b$ class I molecules because of targeted disruption of the H-2D$^b$ and mouse β2-microglobulin genes.

Vaccination Protocol 6 to 10 week old HHD mice were injected intramuscularly in both quadriceps with a total of 50 µg of DNA in 100 µl saline on day 0. Booster injections with the same DNA vaccine coupled with electroporation on day 28 were performed as described previously (Buchan, et a/2005). Animal experimentation was conducted within local Ethical Committee and UK Coordinating Committee for Cancer Research (London, United Kingdom) guidelines under a Home Office License.

IFN-γ ELISpot

Splenocytes from were obtained from immunised mice on day 14 or 36 (Rice, et al 2004) and incubated with the HLA-A*0201-restricted PASD1(1) or PASD1(2) peptides for 22 hours. Vaccine-specific interferon-γ (IFN-γ) release assays were carried out according to the manufacturer's instructions (BD Biosciences, San Diego, Calif.). The p30 peptide (derived from the fragment C fusion domain) was used to assess CD4$^+$ T-cell responses and the efficacy of the DNA vaccine in inducing immune responses. Samples were tested in triplicate with a range of peptide concentration. Control samples were incubated without peptide or with an irrelevant HLA-A2-binding peptide.

Cytotoxic T-Cell Expansion and Detection

Splenocytes obtained from vaccinated mice at day 14 or 36 were cultured for 6 days in 10 to 15 mL complete medium with recombinant human interleukin-2 (IL-2; 20 IU/mL; Perkin-Elmer, Foster City, Calif.) and peptide (0.1 µM). Target cells (RMA-HHD, KMS-12-HHD, YAC-1) were $^{51}$chromium ($^{51}$Cr) labelled during incubation with or without peptide, as indicated. The cytolytic activity of the cultured splenocytes was assessed by standard 5-hour $^{51}$Cr-release assay as previously described (Rice, et al 2004). Specific lysis was calculated by the standard formula [release by CTL–release by targets alone]/[release by 4% NP40–release by targets alone]×100%.

Western Blotting

Western blotting was performed as previously described (Cooper, et al 2006)). Briefly, cell lysates prepared from the Thiel, KMS-12-BM, Jurkat and SUDHL-10 cell lines were resolved by SDS-PAGE and transferred to Immobilon membranes. The membranes were then probed with the monoclonal antibodies PASD1-1 or PASD1-2, washed, incubated with HRP goat anti-mouse IgG washed and the antigen/antibody complexes visualised using the ECL chemiluminescent substrate as previously described (Cooper, et al 2006).

Results p.DOM-PASD1(1) and p.DOM-PASD1(2) Induce γ-IFN Responses in HHD Mice

Figure 8A:
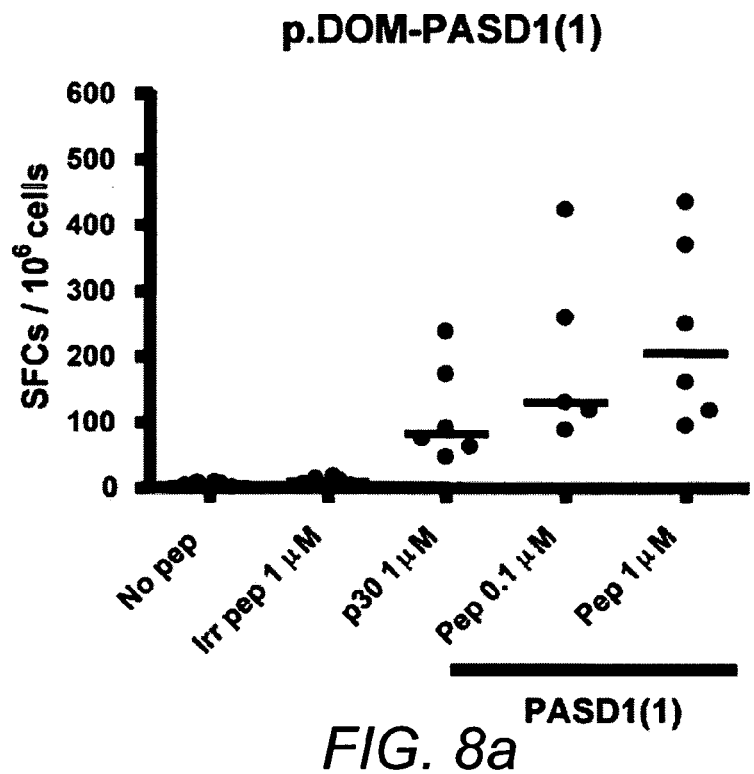
Figure 8B:
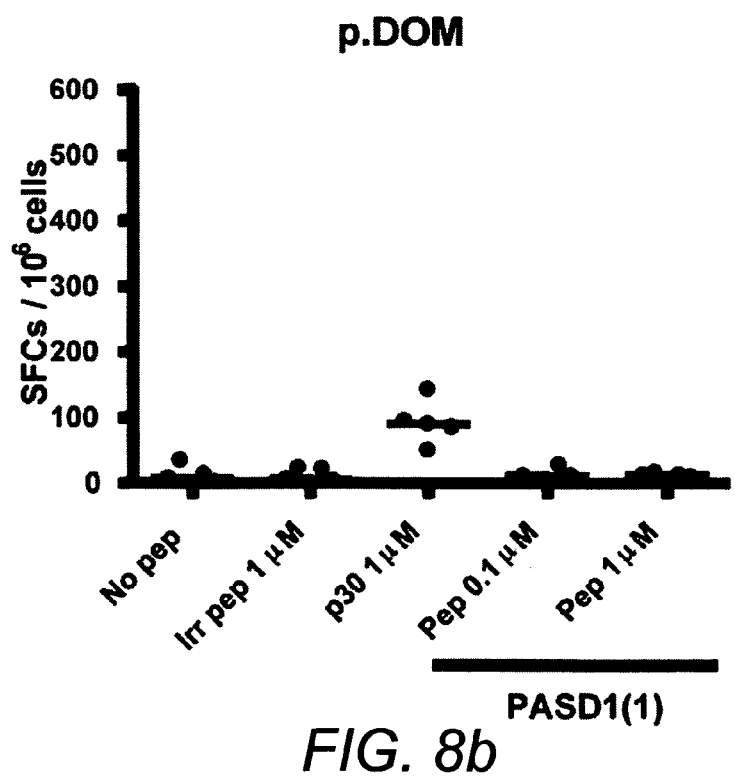
Figure 8C:
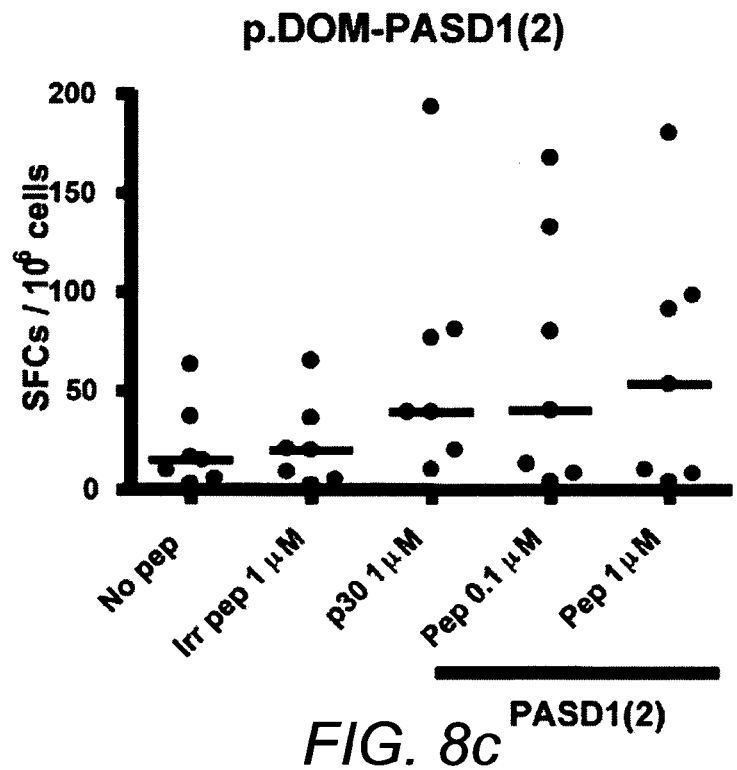
Figure 8D:
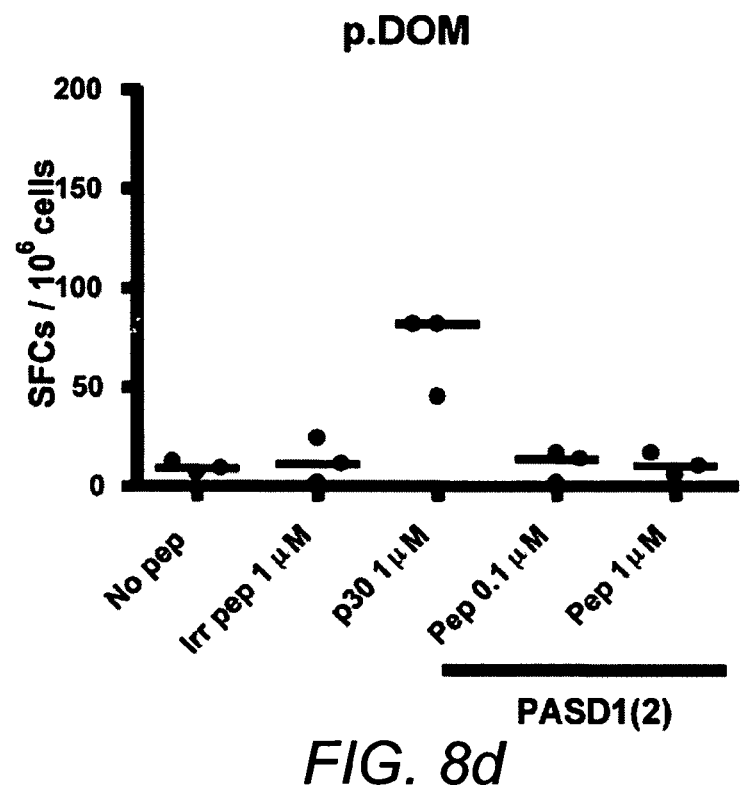

A single priming dose of p.DOM-PASD1(1) or p.DOM-PASD1(2) DNA vaccine induced significant peptide-specific responses in mice 14 days after vaccination. IFNγ release was detected in 100% and 57% of the vaccinated HHD mice, respectively (FIGS. 8A and C). The level of epitope specific T-cell response was more than 2 fold higher in mice vaccinated with p.DOM-PASD1(1) (median 117 SFCs/10$^6$ cells; 1 µM peptide) than in those vaccinated with p.DOM-PASD1(2) (median 53 SFCs/10$^6$ cells; 1 µM). The p.DOM control vaccine gave no PASD1(1) or PASD1(2) specific T-cell response (FIGS. 8B and D). All 3 vaccines however induced a p30-specific T-cell response, thus validating vaccine immunogenicity.

p.DOM-PASD1(1) and p.DOM-PASD1(2) Induce Specific Cytotoxic T Lymphocytes

Figure 9A:
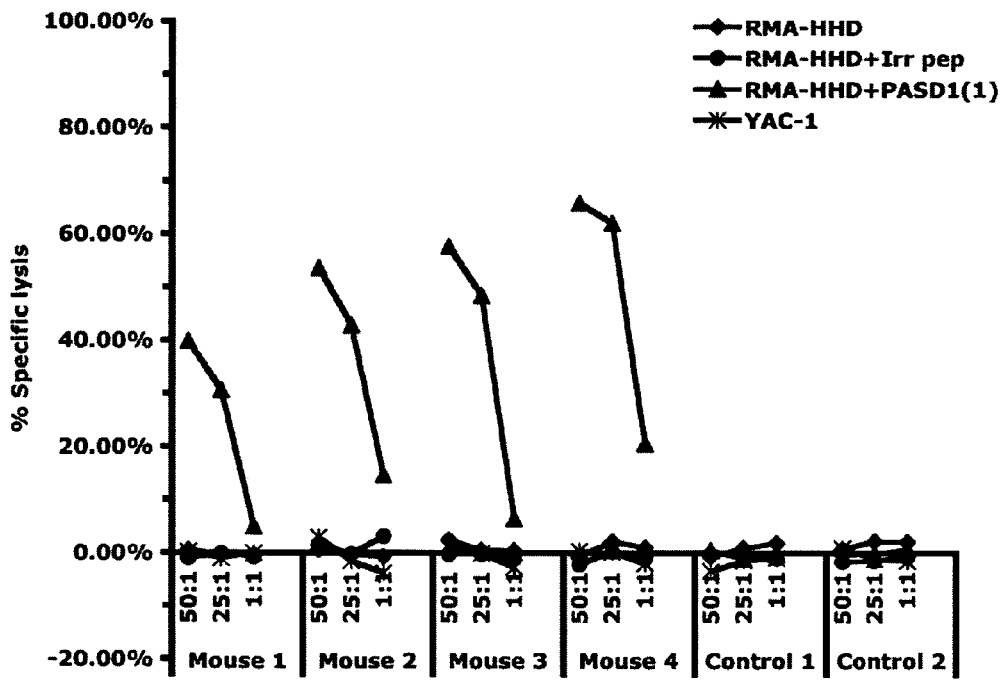
Figure 9B:
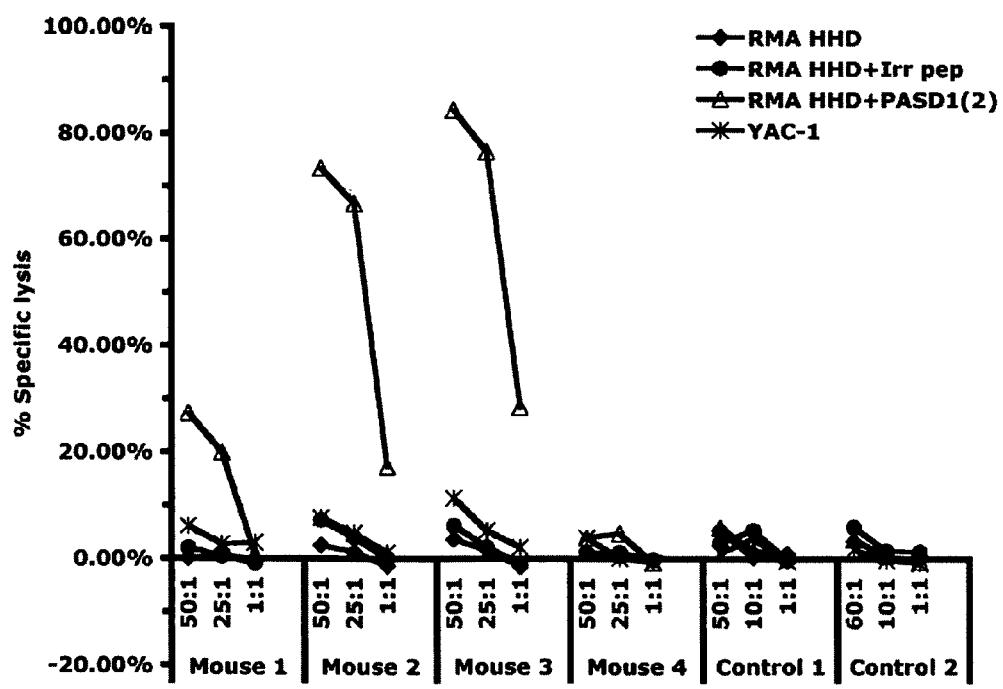

Cultured splenocytes obtained from mice vaccinated with p.DOM-PASD1(1) or p.DOM-PASD1(2) were able to specifically lyse peptide pulsed RMA-HHD cells (FIG. 9). Cytolytic activity was observed in 4/4 mice (8/8 when pooling both experiments) vaccinated with p.DOM-PASD1(1) (FIG. 9A) and 3/4 mice vaccinated with pDOM-PASD1(2) (FIG. 9B). Similarly to p.DOM-PASD1(1), this cytolytic activity was PASD1(2) peptide specific. No significant cytolytic activity of any of the peptide pulsed target cells was detected by cells from mice vaccinated with the control vaccine p.DOM (FIGS. 9A and B). No killing of the PASD1-negative RMA-HHD cells, alone or loaded with an irrelevant peptide was observed in any of the experiments. The absence of killing of the YAC-1 cells confirmed that the cytolytic activity of cells from pDOM-PASD1(1) and p.DOM-PASD1 (2) vaccinated mice was not due to NK cell activity (FIG. 9) and further confirmed that the cytolytic activity observed after vaccination was peptide specific.

DNA Vaccination with Electroporation Boost Improves Specific T-Cell Responses

Figure 10A:
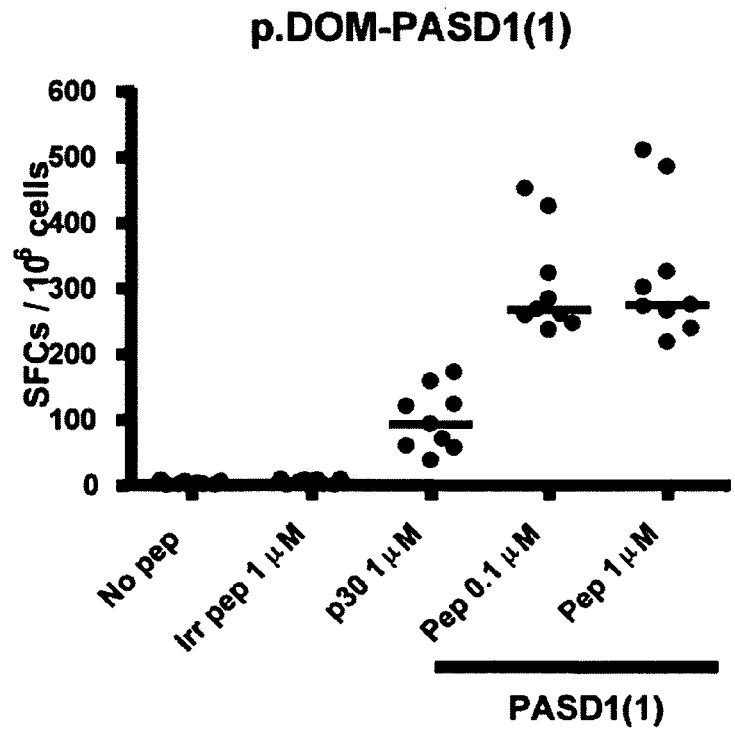
Figure 10B:
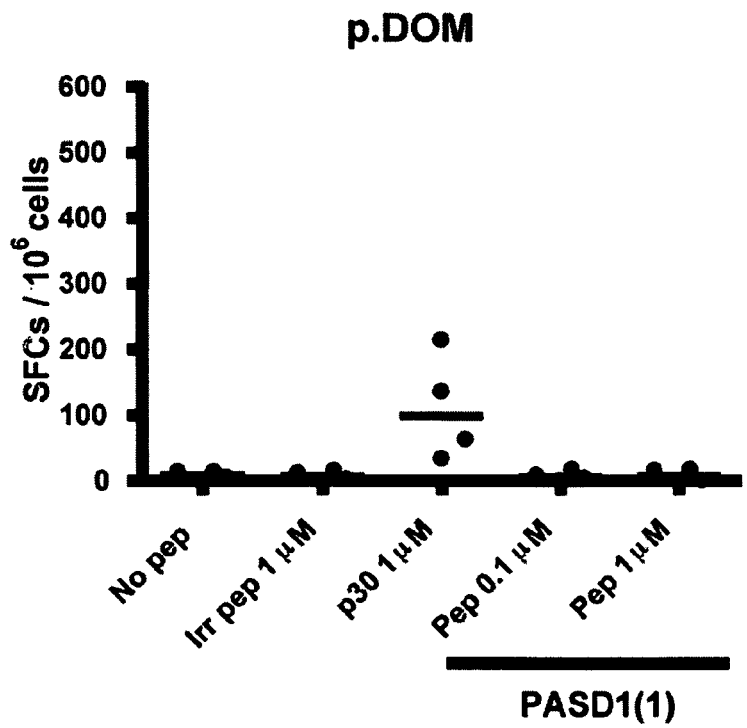
Figure 10C:
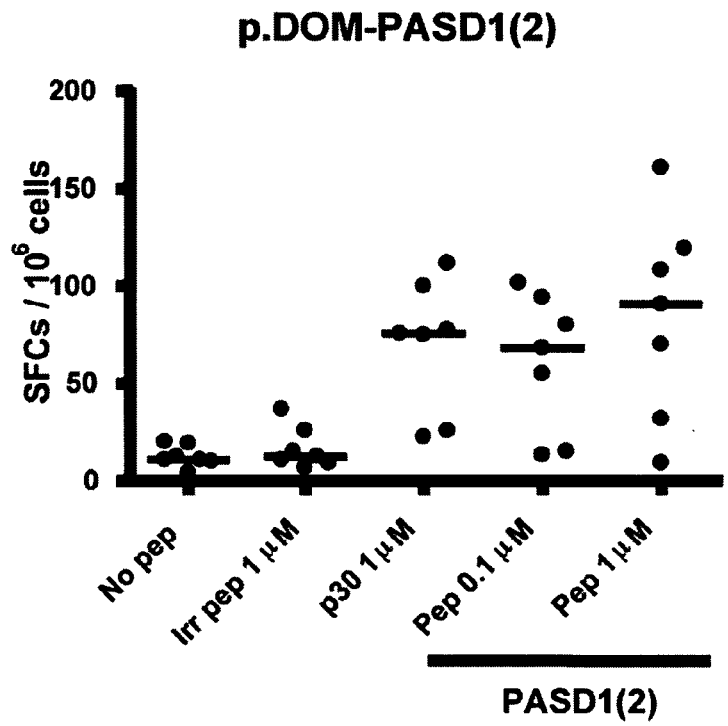
Figure 10D:
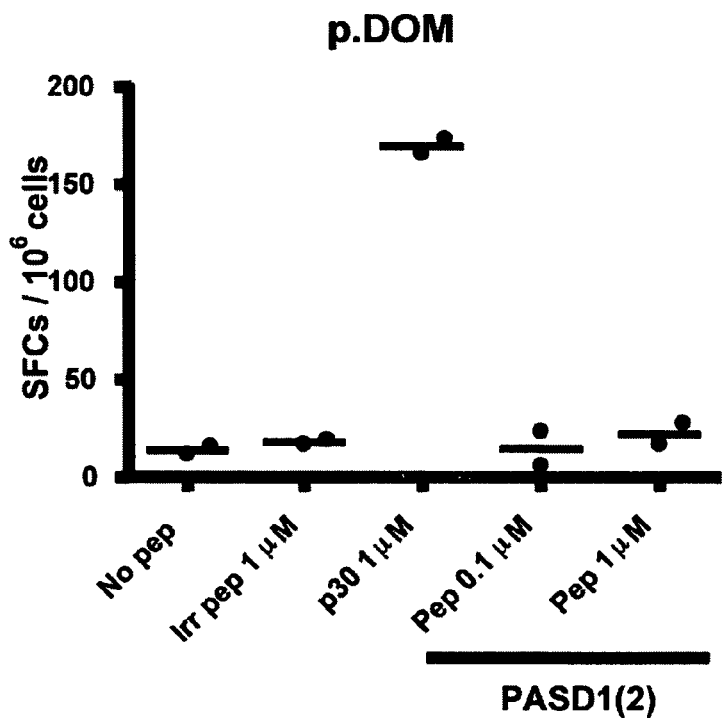
Figure 10E:
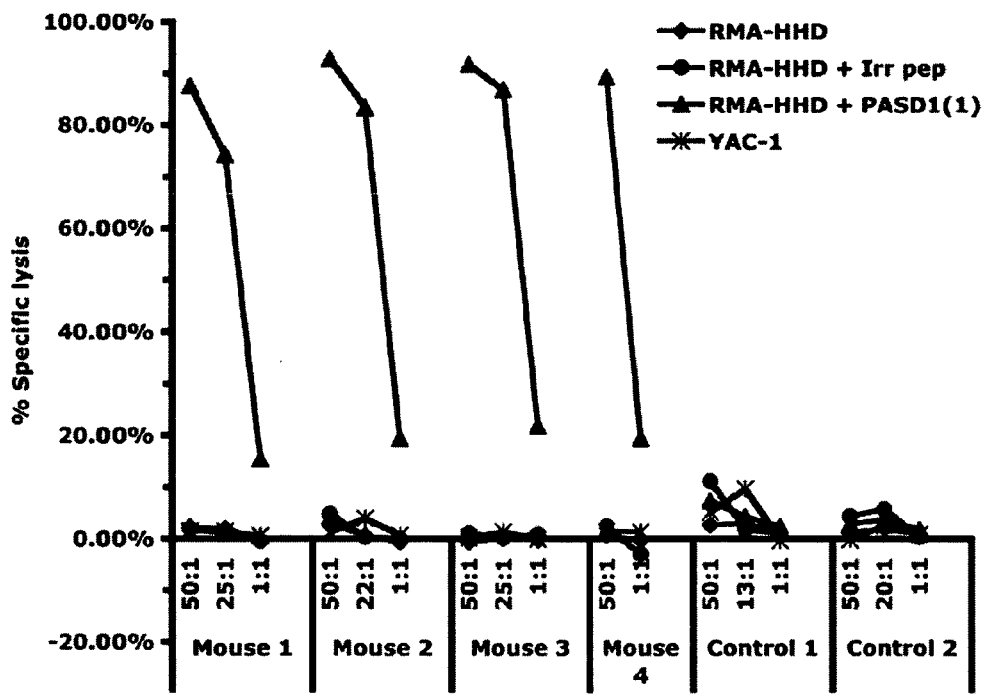
Figure 10F:
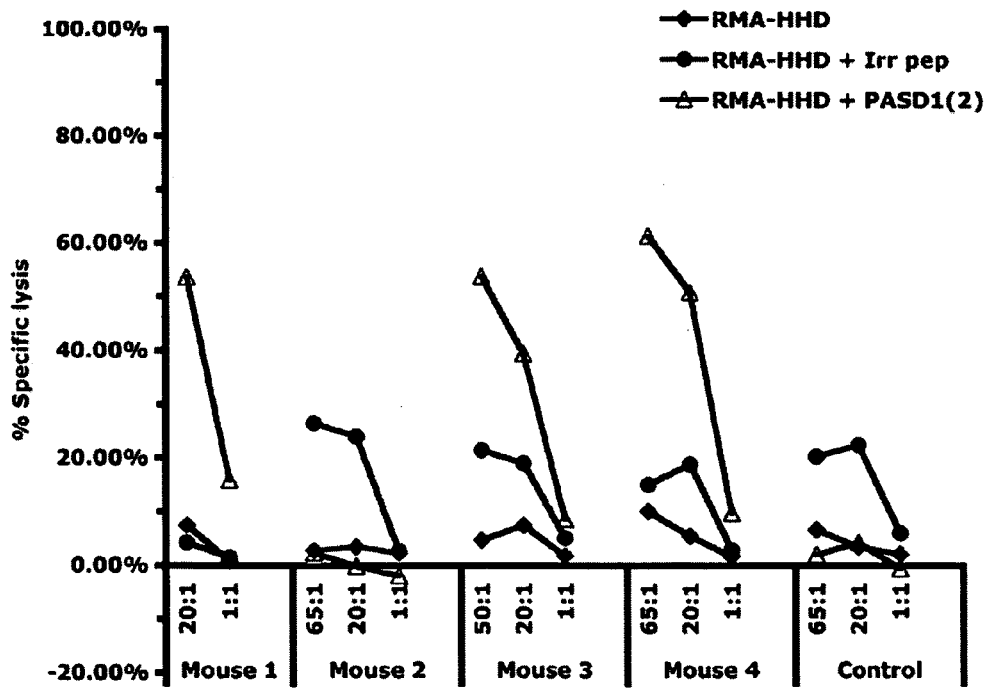

DNA vaccination and electroporation strategies in a homologous prime/boost strategy generate superior T-cell responses (Buchan, et al 2005) and this was investigated for PASD1. HHD mice immunised on day 0 received a booster injection followed immediately by electroporation on day 28 and their spleens were harvested 8 days later to assess the T-cell responses induced. After prime/boost vaccination with p.DOM-PASD1(1), the p30 specific T-cell response was similar to the one observed after priming (FIG. 10) but an increase was observed in the PASD1(1) specific response. This represents >100% increase in the T-cell response (FIG. 10A). An increase in peptide specific cytolysis of peptide-pulsed RMA-HHD cells at the highest E:T ratio was also detected (FIG. 10E). With regard to mice vaccinated with p.DOM-PASD1 (2), the γ-IFN response showed a 42% increase following boosting compared to priming alone with (91 compared to 53 SFC/10$^6$ splenocytes) when incubated with 1 µM of PASD1 (2) peptide (FIG. 10C). However, no increase in was observed in the specific cytolytic activity of cells from the p.DOM-PASD1(2) mice (FIG. 10F).

Confirmation of PASD1 Expression in the Human KMS-12-BM MM Cell Line.

Although the KMS-12-BM cells had previously been shown to express PASD1 mRNA (Sahota, et al 2006) it was important to confirm the expression of PASD1 protein in these cells. Western blotting studies using monoclonal antibodies specific for both the PASD1a and PASD1b proteins confirmed the presence of PASD1 protein exhibiting a molecular weight consistent with that of the full length PASD1b protein in these cells (FIG. 11). Thus we would predict that both PASD1(1) and PASD1(2) epitopes are present in the endogenously expressed protein in these cells. An additional higher molecular weight protein band was labelled using the antibody PASD1b in the KMS-12-BM cells suggesting the presence of additional PASD1 isoforms.

CTLs Induced in Vaccinated HHD Mice are Able to Lyse Human Myeloma Cells

A human MM cell line target (KMS-12-HHD) was generated by the transduction of KMS-12-BM cells with the hybrid HHD MHC molecule. This is commonly required to enable epitope recognition by CTLs from these mice, even in cell lines that express human HLA-A2. Vaccination with p.DOM-PASD1(1) produced T-cells which mediated a specific lysis of PASD1(1) peptide loaded KMS-12-HHD cells (FIG. 12), which was consistent with the results obtained with the peptide loaded PASD1-negative murine RMA-HHD cells (FIG. 10). More importantly, the PASD1(1) specific CTLs induced by the vaccine were able to lyse the KMS-12-HHD cells in the absence of peptide loading or when loaded with an irrelevant peptide (FIG. 12). This result suggests that the PASD1(1) epitope is naturally processed and presented in the human MM cell line KMS-12-HHD at a level permitting a significant level (up to 40%) of killing.

Cells from mice vaccinated with p.DOM-PASD1(2) demonstrated significant lytic activity of the KMS-12-HHD cells when loaded with the PASD1(2) peptide (FIG. 12). However, no lysis was observed of the KMS-12-HHD cells in the absence of peptide loading or when loaded with the irrelevant peptide (FIG. 12). One explanation for this is that the PASD1 (2) peptide may not be naturally processed and presented effectively in this cell line. Another would be perhaps mutation or sequence polymorphisms affecting this region of the PASD1 protein.

Full Length PASD1-Encoding Vaccine (p.DOM-PASD1FL) Induces PASD1$_{38}$ Specific T-Cell Responses in HHD Mice The p.DOM-PASD1FL vaccine was used to examine which PASD1 epitopes are processed and presented in vivo. HHD mice were vaccinated with p.DOM-PASD1FL and their spleens were harvested 14 days later to assess the PASD1(1) and PASD1(2) specific T-cell responses induced. A p30 specific response was detected in all vaccinated mice (FIG. 13B) thus validating the immunogenicity of the p.DOM-PASD1FL vaccine. A PASD1(1) specific γ-IFN response was observed in 8/8 mice with a median of 756 SFCs/10$^6$ splenocytes (FIG. 13A). In contrast only 1/8 mice showed a specific γ-IFN response for PASD1(2) and this was comparably lower than the response to PASD1(1). However, in 1/8 mice both PASD1 (1) and PASD1(2) epitopes were processed and presented after vaccination with the full length antigen. Hence, vaccination with p.DOM-PASD1FL predominantly induced a strong PASD1(1) specific T-cell response in vaccinated mice.

CTLs from the p.DOM-PASD1FL vaccinated mice were re-stimulated with either PASD1(1) or PASD1(2) peptides before assessing their cytolytic activity towards the endogenous PASD1 protein in KMS-12-HHD target cells. With the PASD1(1) peptide, CTLs were able to lyse KMS-12-HHD cells expressing the endogenous PASD1 protein (FIG. 14C). In marked contrast, the PASD1(2) re-stimulated CTLs generated from mice immunised with p.DOM-PASD1FL did not show any cytolytic activity against the target cells (FIG. 14C). CTLs from the mouse that presented a weak PASD1(2) specific T-cell response (FIG. 14A) were even unable to kill PASD1(2) peptide loaded KMS-12-HHD cells (data not shown).

Discussion

This example describes the evaluation of PASD1 as a target for DNA fusion gene vaccines using the pre-clinical HHD A2 transgenic mouse model. The immunogenicity of two PASD1 peptide epitopes, PASD1(1) and PASD1(2), identified as being the most immunogenic in DLBCL patients (Ait-Tahar, et al 2009) were examined individually and as components of a full length PASD1 p-DOM DNA vaccine in an in vivo pre-clinical model system. Although there is a murine PASD1 orthologue, this bears only 25% identity with the human protein (Liggins, et al 2004). This identity resides outside the PASD1 sequences investigated in the current study thus reducing the risk of autoimmune problems arising in the current mouse model or of tolerance to the human epitopes.

The use of the pDOM DNA vaccine system reduces problems of multiple immunodominant CTL epitopes in the Frag C backbone and includes a CD4 T-helper epitope. This results in the increased immunogenicity of the targeted antigen and the activation of both the innate and adaptive immune response of to provide long-lasting specific immune responses, even in a tolerised host (Rice, et al 2002, Rice, et al 2001). This approach has been shown to provide protection against tumour challenge in multiple murine tumour models (King, et al 1998, Rice, et al 1999, Spellerberg, et al 1997) and is currently under investigation in a number of Phase 1/II trials in cancer.

PASD1 expression has been previously detected not only in MM-derived cell lines but also primary cases of MM (Cooper, et al 2006, Sahota, et al 2006). This level of PASD1 expression in MM cells is comparable to, or can exceed that of NY-ESO-1, an important CTA in MM reported in ~25% of tumour cells (Dhodapkar, et al 2003). We have also confirmed the expression of endogenous PASD1 protein in the KMS-12-BM MM-derived cells that were used as vaccine targets in the present study. These results reinforce the relevance of PASD1 as a target for immunotherapy in MM.

The p.DOM-PASD1(1) vaccine generated a robust T-cell response that was x2-fold greater than induced by the p.DOM-PASD1(2) vaccine following a single priming dose. Comparable levels of cytotoxicity were, however, obtained against murine PASD1-negative RMA-HHD target cells loaded with relevant PASD1 peptides with γ-IFN secreting T cells being induced by both vaccines. The cytolytic activity of the CTLs indicated that both of the PASD1 epitopes were efficiently presented in vivo through cross-presentation by antigen processing cells when delivered as a fusion protein via DNA vaccines (Radcliffe, et al 2006). These data also indicate that an A2-restricted T-cell repertoire is available to recognise both PASD1-derived epitopes. The delivery of epitopes using a prime/boost electroporation strategy (permits increased DNA uptake by the muscle cells at the injection site resulting in increased antigen expression (Aihara and Miyazaki 1998, Mathiesen 1999, Mir, et al 1999). This augmented MM cell line killing via PASD1(1) but had no effect on PASD1(2) lytic activity, revealing a variability in the potential to augment responses by some, but not all, antigen-derived epitopes.

Differences in the cytolytic effect of CTLs raised against the p-DOM-PASD1(1) and p.DOM-PASD1(2) vaccines were observed on the chimeric KMS-12-HHD cells. While both epitope-specific DNA vaccines generated cytolytic cells which were able to lyse the peptide loaded KMS-12-HHD MM cells, only CTLs from mice vaccinated with p-DOM-PASD1(1) were able to kill KMS-12-HHD cells in the absence of exogenous relevant peptide, indicating that PASD1(1) and not PASD1(2) was naturally processed and presented at a sufficient pMHC density to allow direct killing of this cell line.

The difference between the PASD1(1) and PASD1(2) peptides was even more pronounced when the efficacy of the DNA vaccine encoding the full length PASD1 protein was studied. With p.DOM-PASD1FL, a single priming dose invariably elicited high levels of PASD1(1) specific T cells but this vaccine elicited PASD1(2)-specific cells only infrequently. Furthermore, only the CTLs recognising PASD1(1) were cytolytic against the endogenous PASD1 protein in the highly relevant chimeric KMS-12-HHD MM cells. These data confirm that, of the two epitopes examined, only the PASD1(1) epitope is naturally presented at a level sufficient for tumour cell killing of this cell line. This is of interest since neither this difference in the presentation of the two PASD1 epitopes in this cell line nor their differing immunogenicity when processed and presented from the full length PASD1 vaccine could have been predicted using in silico epitope prediction programmes.

It is notable, however, that in our previous study investigating the immune response to PASD1 in DLBCL patients the PASD1(2) epitope was presented and recognised by patients'CTLs on non-peptide loaded Thiel cells (another MM cell line expressing endogenous PASD1). Explanations for the difference in recognition of PASD1(2) between the two studies include a) differences in natural processing and presentation of PASD1 in different tumour cells, b) the presence of different PASD1 proteins which may not contain the PASD1(2) epitope in the tumour cells (although this is unlikely as both Thiel and KMS-BM-12 cells express a comparable molecular weight PASD1 protein) c) differential processing of antigenic peptides between human and mouse cells and d) epitope dominance (Palmowski, et al 2006). It is also possible that there may be mutations or naturally occurring sequence polymorphisms in the region encoding the PASD1 (2) peptide that alter its protein sequence. Indeed we have evidence from both our previous and the present study (Cooper, et al 2006, Sahota, et al 2006) to support the expression of additional PASD1 isoforms in different tumour cell types.

The results from our previous study in DLBCL (Ait-Tahar, et al 2009) and the in vivo DNA vaccine study confirm that human DLBCL and MM cells retain an intact MHC class I processing and presentation machinery able to present PASD1 CTL epitopes at a relevant density. The findings also suggest that PASD1 is a suitable target to ablate MM cells using DNA vaccines. In view of the heterogeneity of CTA expression in tumour cells (Dhodapkar, et al 2003, Goodyear, et al 2005) it will be important to include sufficient numbers of CTA epitopes in a vaccine to target the maximum number of tumour cells whilst minimising risks with autoimmunity or problems caused by epitope dominance.

This study is the first to target a CTA with DNA vaccination in MM. The use of PASD1-p.DOM vaccine in a prime/boost electroporation strategy DNA vaccine represents a potentially important therapeutic approach not only for MM and DLBCL but also for a variety of other PASD1-positive cancers.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims. Moreover, all embodiments described herein are considered to be broadly applicable and combinable with any and all other consistent embodiments, as appropriate.

Various publications are cited herein, the disclosures of which are incorporated by reference in their entireties.

REFERENCES

1. Abramson J S. T-cell/histiocyte-rich B-cell lymphoma and the paradox of the host immune response. Leuk Lymphoma 2007; 48(9):1670-1.
2. Adams S P, Sahota S S, Mijovic A, Czepulkowski B, Padua R A, Mufti G J, et al. Frequent expression of HAGE in presentation chronic myeloid leukaemias. Leukemia 2002; 16(11):2238-42.
3. Aihara H & Miyazaki J Gene transfer into muscle by electroporation in vivo. Nat. Biotechnol. 1998; 16:867-870.
4. Ait-Tahar K, Cerundolo V, Banham A H, Hatton C, Blanchard T J, Kusec R, et al. B and CTL responses to the ALK protein in patients with ALK-positive ALCL. Int J. Cancer. 2006; 118:688-95.
5. Ait-Tahar K, Liggins A P, Collins G P, Campbell A, Barnardo M, Lawrie C, Moir D, Hatton C, Banham A H, Pulford K Cytolytic T-cell response to the PASD1 cancer testis antigen in patients with diffuse large B-cell lymphoma. Br J Haematol, 2009; 146:396-407.
6. Andrade V C, Vettore A L, Felix R S, Almeida M S, Carvalho F, Oliveira J S, et al. Prognostic impact of cancer/testis antigen expression in advanced stage multiple myeloma patients. Cancer Immun 2008; 8:2.
7. Ashfield R, Jakobsen B K. Making high-affinity T-cell receptors: A new class of targeted therapeutics. Drugs 2006; 9: 554-559
8. Atanackovic D, Arfsten J, Cao Y, Gnjatic S, Schnieders F, Bartels K, et al. Cancer-testis antigens are commonly expressed in multiple myeloma and induce systemic immunity following allogeneic stem cell transplantation. Blood 2007; 109(3):1103-12.
9. Atanackovic D, Blum I, Cao Y, Wenzel S, Bartels K, Faltz C, et al. Expression of cancer-testis antigens as possible targets for antigen-specific immunotherapy in head and neck squamous cell carcinoma. Cancer Biol Ther 2006; 5(9):1218-25.
10. Barrow C, Browning J, MacGregor D, Davis I D, Sturrock S, Jungbluth A A, et al. Tumor antigen expression in melanoma varies according to antigen and stage. Clin Cancer Res 2006; 12(3 Pt 1):764-71.
11. Baumgaertner P, Rufer N, Devevre E, Derre L, Rimoldi D, Geldhof C, et al. Ex vivo detectable human CD8 T-cell responses to cancer-testis antigens. Cancer Res 2006; 66(4):1912-6.
12. Bellucci R, Wu C J, Chiaretti S, Weller E, Davies F E, Alyea E P, et al. Complete response to donor lymphocyte infusion in multiple myeloma is associated with antibody responses to highly expressed antigens. Blood 2004; 103 (2):656-63.
13. Bianco N R, Kim S H, Morelli A E, Robbins P D. Modulation of the immune response using dendritic cell-derived exosomes. Methods Mol Biol 2007; 380:443-57.
14. Buchan, S., Gronevik, E., Mathiesen, I., King, C. A., Stevenson, F. K. & Rice, J. (2005) Electroporation as a "prime/boost" strategy for naked DNA vaccination against a tumor antigen. J Immunol, 174, 6292-6298.
15. Carreras J, Lopez-Guillermo A, Fox B C, Colomo L, Martinez A, Roncador G, et al. High numbers of tumor-infiltrating FOXP3-positive regulatory T cells are associated with improved overall survival in follicular lymphoma. Blood 2006; 108(9):2957-64.
16. Chiriva-Internati M, Wang Z, Salati E, Wroblewski D, Lim S H. Successful generation of sperm protein 17 (Sp17)-specific cytotoxic T lymphocytes from normal donors: implication for tumour-specific adoptive immunotherapy following allogeneic stem cell transplantation for Sp17-positive multiple myeloma. Scand J Immunol 2002; 56(4):429-33.
17. Chiriva-Internati M, Wang Z, Xue Y, Bumm K, Hahn A B, Lim S H. Sperm protein 17 (Sp17) in multiple myeloma: opportunity for myeloma-specific donor T cell infusion to enhance graft-versus-myeloma effect without increasing graft-versus-host disease risk. Eur J Immunol 2001; 31(8): 2277-83.
18. Condomines M, Hose D, Raynaud P, Hundemer M, De Vos J, Baudard M, et al. Cancer/testis genes in multiple 19. Cooper C D, Liggins A P, Ait-Tahar K, Roncador G, Banham A H, Pulford K. PASD1, a DLBCL-associated cancer testis antigen and candidate for lymphoma immunotherapy. Leukemia 2006.
20. Coral S, Sigalotti L, Altomonte M, Engelsberg A, Colizzi F, Cattarossi I, et al. 5-aza-2'-deoxycytidine-induced expression of functional cancer testis antigens in human renal cell carcinoma: immunotherapeutic implications. Clin Cancer Res 2002; 8(8):2690-5.
21. Corradi J P, Yang C, Darnell J C, Dalmau J, Darnell R B. A post-transcriptional regulatory mechanism restricts expression of the paraneoplastic cerebellar degeneration antigen cdr2 to immune privileged tissues. J Neurosci 1997; 17(4):1406-15.
22. Dave S S, Wright G, Tan B, Rosenwald A, Gascoyne R D, Chan W C, et al. Prediction of survival in follicular lymphoma based on molecular features of tumor-infiltrating immune cells. N Engl J Med 2004; 351(21):2159-69.
23. Dhodapkar M V, Osman K, Teruya-Feldstein J, Filippa D, Hedvat C V, Iversen K, et al. Expression of cancer/testis (CT) antigens MAGE-A1, MAGE-A3, MAGE-A4, CT-7, and NY-ESO-1 in malignant gammopathies is heterogeneous and correlates with site, stage and risk status of disease. Cancer Immun 2003; 3:9.
24. El Weshi A, Akhtar S, Mourad W A, Ajarim D, Abdelsalm M, Khafaga Y, et al. T-cell/histiocyte-rich B-cell lymphoma: Clinical presentation, management and prognostic factors: report on 61 patients and review of literature. Leuk Lymphoma 2007; 48(9):1764-73.
25. Goodyear O, Piper K, Khan N, Starczynski J, Mahendra P, Pratt G, et al. CD8+ T cells specific for cancer germline gene antigens are found in many patients with multiple myeloma, and their frequency correlates with disease burden. Blood 2005; 106(13):4217-24.
26. Goodyear O, Pratt G, McLarnon A, Cook M, Piper K, Moss P. Differential pattern of CD4+ and CD8+ T cell immunity to MAGE-A1/A2/A3 in patients with monoclonal gammapathy of undetermined significance (MGUS) and multiple myeloma. Blood 2008; Epub ahead of print.
27. Guinn B A, Bland E A, Lodi U, Liggins A P, Tobal K, Petters S, et al. Humoral detection of leukaemia-associated antigens in presentation acute myeloid leukaemia. Biochem Biophys Res Commun 2005; 335(4):1293-304.
28. Hans C P, Weisenburger D D, Greiner T C, Gascoyne R D, Delabie J, Ott G, et al. Confirmation of the molecular classification of diffuse large B-cell lymphoma by immunohistochemistry using a tissue microarray. Blood 2004; 103(1):275-82.
29. Heidebrecht H J, Claviez A, Kruse M L, Pollmann M, Buck F, Harder S, et al. Characterization and expression of CT45 in Hodgkin's lymphoma. Clin Cancer Res 2006; 12(16):4804-11.
30. Huang S, Preuss K D, Xie X, Regitz E, Pfreundschuh M. Analysis of the antibody repertoire of lymphoma patients. Cancer Immunol Immunother 2002; 51(11-12):655-62.
31. Hudolin T, Juretic A, Pasini J, Tomas D, Spagnoli G C, Heberer M, et al. Immunohistochemical expression of tumor antigens MAGE-A1, MAGE-A3/4, and NY-ESO-1 in squamous cell carcinoma of the penis. Urology 2006; 68(1):205-7.
32. Inokuma M, dela Rosa C, Schmitt C, Haaland P, Siebert J, Petry D, et al. Functional T cell responses to tumor antigens in breast cancer patients have a distinct phenotype and cytokine signature. J Immunol 2007; 179(4):2627-33.
33. Jacobs J F, Brasseur F, Hulsbergen-van de Kaa C A, van de Rakt M W, Figdor C G, Adema G J, et al. Cancer-germline gene expression in pediatric solid tumors using quantitative real-time PCR. Int J Cancer 2007; 120(1):67-74.
34. Jager E, Nagata Y, Gnjatic S, Wada H, Stockert E, Karbach J, et al. Monitoring CD8 T cell responses to NY-ESO-1: correlation of humoral and cellular immune responses. Proc Natl Acad Sci USA 2000; 97(9):4760-5.
35. Jackson H, Dimopoulos N, Mifsud N A, Tai T Y, Chen Q, Svobodova S, Browning J, Luescher I, Stockert L, Old L J, Davis I D, Cebon J, Chen W. Striking immunodominance hierarchy of naturally occurring CD8+ and CD4+ T cell responses to tumor antigen Ny-ESO-1. J Immunol 2006: 176:5908-17.
36. Jungbluth A A, Ely S, DiLiberto M, Niesvizky R, Williamson B, Frosina D, et al. The cancer-testis antigens CT7 (MAGE-C1) and MAGE-A3/6 are commonly expressed in multiple myeloma and correlate with plasma-cell proliferation. Blood 2005; 106(1):167-74.
37. King, C. A., Spellerberg, M. B., Zhu, D., Rice, J., Sahota, S. S., Thompsett, A. R., Hamblin, T. J., Radl, J. & Stevenson, F. K. (1998) DNA vaccines with single-chain Fv fused to fragment C of tetanus toxin induce protective immunity against lymphoma and myeloma. Nat Med, 4, 1281-1286.
38. Liggins A P, Guinn B A, Hatton C S, Pulford K, Banham A H. Serologic detection of diffuse large B-cell lymphoma-associated antigens. Int J Cancer 2004a; 110:934.
39. Liggins A P, Brown P J, Asker K, Pulford K, Banham A H. A novel diffuse large B-cell lymphoma-associated cancer testis antigen encoding a PAS domain protein. Br J Cancer 2004b; 91(1):141-9.
40. Lim S H, Wang Z, Chiriva-Internati M, Xue Y. Sperm protein 17 is a novel cancer-testis antigen in multiple myeloma. Blood 2001; 97(5):1508-10.
41. Luckey C J, King G M, Marto J A, Venketeswaran S, Maier B F, Crotzer V L, et al. Proteasomes can either generate or destroy MHC class I epitopes: evidence for nonproteasomal epitope generation in the cytosol. J Immunol 1998; 161(1):112-21.
42. Mandic M, Alumunia C, Vicel S, Gillet D, Janjic B, Coval K, Maillere B, Kirkwood J M, Zarour H M. The alternative open reading frame of LAGE-1 gives rise oto multiple promiscuous HLA-DR-restricted epitopes recognized by T-helper 1-type tumor-reactive CD4+ T cells. Cancer Res 2003; 63(19):6505-15.
43. Mashino K, Sadanaga N, Tanaka F, Yamaguchi H, Nagashima H, Inoue H, et al. Expression of multiple cancer-testis antigen genes in gastrointestinal and breast carcinomas. Br J Cancer 2001; 85(5):713-20.
44. Mathiesen, I. (1999) Electropermeabilization of skeletal muscle enhances gene transfer in vivo. Gene Ther, 6, 508-514.
45. Mir, L. M., Bureau, M. F., Gehl, J., Rangara, R., Rouy, D., Caillaud, J. M., Delaere, P., Branellec, D., Schwartz, B. & Scherman, D. (1999) High-efficiency gene transfer into skeletal muscle mediated by electric pulses. Proc Natl Acad Sci USA, 96, 4262-4267.
46. Monti S, Savage K J, Kutok J L, Feuerhake F, Kurtin P, Mihm M, Wu B, Pasqualucci L, Neuberg D, Aguiar R C, Dal Cin P, Ladd C, Pinkus G S, Salles G, Harris N L, DAla-Favera R, Habermann T M, Aster J C, Golub T R, Shipp M A. Molecular profiling of diffuse large B-cell lymphoma identifies robust subtypes including one characterized by host inflammatory response. Blood 2005; 105 (5):1851-61.

47. Mosmann T R, Coffman R L. TH1 and TH2 cells: different patterns of lymphokine secretion lead to different functional properties. Ann. Rev. Immunol. 7:145-173, 1989
48. Nakagawa K, Noguchi Y, Uenaka A, Sato S, Okumura H, Tanaka M, et al. XAGE-1 expression in non-small cell lung cancer and antibody response in patients. Clin Cancer Res 2005; 11(15):5496-503.
49. Odunzi K, Qian F, Matsuzaki J, Mhawech-Fauceglia P, Andrews C, Hoffman E W, Pan L, Ritter G, Villella J, Thomas B, Rodabaugh K, Lele S, Shrikant P, Old L J, Gnjatic S. Vaccination with an NY-ESO-1 peptide of HLA class I/II specificities induces integrated humoral and T cell responses in ovarian cancer. Proc Natl Acad Sci 2007; 104(31):12837-12842.
50. Oestrand-Rosenberg S. CD4+ T lymhocytes: a critical component of anti-tumour immunity. Cancer Invest 2005; 23:413-419.
51. Palmowski, M. J., Gileadi, U., Salio, M., Gallimore, A., Millrain, M., James, E., Addey, C., Scott, D., Dyson, J., Simpson, E. & Cerundolo, V. (2006) Role of immunoproteasomes in cross-presentation. J Immunol, 177, 983-990.
52. Parker K C, Bednarek M A, Coligan J E. Scheme for ranking potential HLA-A2 binding peptides based on independent binding of individual peptide side-chains. J Immunol 1994; 152(1):163-75.
53. Parker K C, Bednarek M A, Hull L K, Utz U, Cunningham B, Zweerink H J, et al. Sequence motifs important for peptide binding to the human MHC class I molecule, HLA-A2. J Immunol 1992; 149(11):3580-7.
54. Pascolo, S., Bervas, N., Ure, J. M., Smith, A. G., Lemonnier, F. A. & Perarnau, B. (1997) HLA-A2.1-restricted education and cytolytic activity of CD8(+) T lymphocytes from beta2 microglobulin (beta2m) HLA-A2.1 monochain transgenic H-2Db beta2m double knockout mice. J Exp Med, 185, 2043-2051.
55. Passoni L, Gallo B, Biganzoli E, Stefanoni R, Massimino M, Di Nicola M, et al. In vivo T-cell immune response against anaplastic lymphoma kinase in patients with anaplastic large cell lymphomas. Haematologica 2006; 91(1): 48-55.
56. Pellat-Deceunynck C, Mellerin M P, Labarriere N, Jego G, Moreau-Aubry A, Harousseau J L, et al. The cancer germ-line genes MAGE-1, MAGE-3 and PRAME are commonly expressed by human myeloma cells. Eur J Immunol 2000; 30(3):803-9.
57. Porter D L, Antin J H. Donor leukocyte infusions in myeloid malignancies: new strategies. Best Pract Res Clin Haematol 2006; 19(4):737-55.
58. Preuss K D, Zwick C, Bormann C, Neumann F, Pfreundschuh M. Analysis of the B-cell repertoire against antigens expressed by human neoplasms. Immunol Rev 2002; 188:43-50.
59. Pulford K, Banham A H, Lyne L, Jones M, Ippolito G C, Liu H, et al. The BCL11AXL transcription factor: its distribution in normal and malignant tissues and use as a marker for plasmacytoid dendritic cells. Leukemia 2006; 20(8):1439-41.
60. Radcliffe, J. N., Roddick, J. S., Friedmann, P. S., Stevenson, F. K. & Thirdborough, S. M. (2006) Prime-boost with alternating DNA vaccines designed to engage different antigen presentation pathways generates high frequencies of peptide-specific CD8+ T cells. J Immunol, 177, 6626-6633.
61. Rajapakse M, Schmidt B, Brusic V: Multi-Objective Evolutionary Algorithm for Discovering Peptide Binding Motifs. In Applications of Evolutionary Computing. Volume 3907. Lecture Notes in Computer Science, Springer; 2006:149-158
62. Rezvani K, Yong A S, Savani B N, Mielke S, Keyvanfar K, Gostick E, et al. Graft-versus-leukemia effects associated with detectable Wilms tumor-1 specific T lymphocytes following allogeneic stem cell transplantation for acute lymphoblastic leukemia (ALL). Blood 2007.
63. Rice, J., Buchan, S., Dewchand, H., Simpson, E. & Stevenson, F. K. (2004) DNA fusion vaccines induce targeted epitope-specific CTLs against minor histocompatibility antigens from a normal or tolerized repertoire. J Immunol, 173, 4492-4499.
64. Rice, J., Buchan, S. & Stevenson, F. K. (2002) Critical components of a DNA fusion vaccine able to induce protective cytotoxic T cells against a single epitope of a tumor antigen. J Immunol, 169, 3908-3913.
65. Rice, J., Elliott, T., Buchan, S. & Stevenson, F. K. (2001) DNA fusion vaccine designed to induce cytotoxic T cell responses against defined peptide motifs: implications for cancer vaccines. J Immunol, 167, 1558-1565.
66. Rice, J., King, C. A., Spellerberg, M. B., Fairweather, N. & Stevenson, F. K. (1999) Manipulation of pathogen-derived genes to influence antigen presentation via DNA vaccines. Vaccine, 17, 3030-3038.
67. Rimsza L M, Roberts R A, Miller T P, Unger J M, LeBlanc M, Braziel R M, et al. Loss of MHC class II gene and protein expression in diffuse large B-cell lymphoma is related to decreased tumor immunosurveillance and poor patient survival regardless of other prognostic factors: a follow-up study from the Leukemia and Lymphoma Molecular Profiling Project. Blood 2004; 103(11):4251-8.
68. Rosenwald A, Wright G, Chan W C, Connors J M, Campo E, Fisher R I, et al. The use of molecular profiling to predict survival after chemotherapy for diffuse large-B-cell lymphoma. N Engl J Med 2002; 346(25):1937-47.
69. Sahota S S, Goonewardena C M, Cooper C D, Liggins A P, Ait-Tahar K, Zojer N, et al. PASD1 is a potential multiple myeloma-associated antigen. Blood 2006; 108(12):3953-5.
70. Sambrook and Russell, Molecular cloning: A Laboratory Manual, Cold Spring Harbour Laboratory (2001).
71. Scanlan M J, Simpson A J, Old L J. The cancer/testis genes: review, standardization, and commentary. Cancer Immun 2004; 4:1.
72. Schmitt M, Schmitt A, Rojewski M T, Chen J, Giannopoulos K, Fei F, et al. RHAMM-R3 peptide vaccination in patients with acute myeloid leukemia, myelodysplastic syndrome, and multiple myeloma elicits immunologic and clinical responses. Blood 2008; 111(3):1357-65.
73. Schuler M M, Nastke M D, Stevanoviké S. SYFPEITHI: database for searching and T-cell epitope prediction. Methods Mol Biol. 2007; 409:75-93.
74. Sigalotti L, Coral S, Altomonte M, Natali L, Gaudino G, Cacciotti P, et al. Cancer testis antigens expression in mesothelioma: role of DNA methylation and bioimmunotherapeutic implications. Br J Cancer 2002; 86(6):979-82.
75. Simpson A J, Caballero O L, Jungbluth A, Chen Y T, Old L J. Cancer/testis antigens, gametogenesis and cancer. Nat Rev Cancer 2005; 5(8):615-25.
76. Southwood S, Sidney J, Kondo A, del Guercoa M F, Appella E, Hoffman S, Kubo R T, Chesnut R W, Grey H M, Sette A. Several common HLA-DR types share largely overlapping peptide binding repertoires. J Immunol 1998; 160:3363-3373.
77. Spellerberg, M. B., Zhu, D., Thompsett, A., King, C. A., Hamblin, T. J. & Stevenson, F. K. (1997) DNA vaccines against lymphoma: promotion of anti-idiotypic antibody responses induced by single chain Fv genes by fusion to tetanus toxin fragment C. J Immunol, 159, 1885-1892.
78. Stauss H J, Cesco-Gaspere M, Thomas S, Hart D P, Xue S A, Holler A, Wright G, Perro M, Little A M, Pospori C, King J, Morris E C. Monoclonal T-cell receptors: new reagents for cancer therapy. Mol Ther. 2007 October; 15(10):1744-50.
79. Sugita Y, Wada H, Fujita S, Nakata T, Sato S, Noguchi Y, et al. NY-ESO-1 expression and immunogenicity in malignant and benign breast tumors. Cancer Res 2004; 64(6): 2199-204.
80. Suri A. Cancer testis antigens—their importance in immunotherapy and in the early detection of cancer. Expert Opin Biol Ther 2006; 6(4):379-89.
81. Szmania S, Tricot G, van Rhee F. NY-ESO-1 immunotherapy for multiple myeloma. Leuk Lymphoma 2006; 47(10):2037-48.
82. Theurillat J P, Ingold F, Frei C, Zippelius A, Varga Z, Seifert B, et al. NY-ESO-1 protein expression in primary breast carcinoma and metastases: correlation with CD8+ T-cell and CD79a+ plasmacytic/B-cell infiltration. Int J Cancer 2007; 120(11):2411-7.
83. Tinguely M, Jenni B, Knights A, Lopes B, Korol D, Rousson V, et al. MAGE-C1/CT-7 expression in plasma cell myeloma: Sub-cellular localization impacts on clinical outcome. Cancer Sci 2008.
84. Thomas S, Xue S A, Cesco-Gaspere M, San Jose E, Hart D P, Wong V, et al. Targeting the Wilms tumor antien 1 by TCR gene transfer:TCR variants improve tetramer binding but not the function of gene modified human T cells. J Immunol 2007; 179(9):5803-10.
85. Valmori D, Dutoit V, Lienard D, Rimoldi D, Pittet M J, Champagne P, et al. Naturally occurring human lymphocyte antigen-A2 restricted CD8+ T-cell response to the cancer testis antigen NY-ESO-1 in melanoma patients. Cancer Res 2000; 60(16):4499-506.
86. van Rhee F, Szmania S M, Zhan F, Gupta S K, Pomtree M, Lin P, et al. NY-ESO-1 is highly expressed in poor-prognosis multiple myeloma and induces spontaneous humoral and cellular immune responses. Blood 2005; 105(10):3939-44.
87. Vierboom M P, Zwaveling S, Bos G M J, Ooms M, Krietemeijer G M, Melief C J, et al. High steady-state levels of p53 are not a prerequisite for tumor eradication by wild-type p53-specific cytotoxic T lymphocytes. Cancer Res 2000; 60(19):5508-13.
88. Wagner W M, Ouyang Q, Pawelec G. The abl/bcr gene product as a novel leukemia-specific antigen: peptides spanning the fusion region of abl/bcr can be recognized by both CD4+ and CD8+ T lymphocytes. Cancer Immunol Immunother 2003; 52(2):89-96.
89. Xie X, Wacker H H, Huang S, Regitz E, Preuss K D, Romeike B, et al. Differential expression of cancer testis genes in histological subtypes of non-Hodgkin's lymphomas. Clin Cancer Res 2003; 9(1):167-73.
90. Xue S, Gillmore R, Downs A, Tsallios A, Holler A, Gao L, et al. Exploiting T cell receptor genes for cancer immunotherapy. Clin Exp Immunol 2005 139(2):167-72.
91. Xue S A, Stauss H J. Enhancing immune responses for cancer therapy. Cell Mol. Immunol. 2007 June; 4(3):173-84.
92. Zeng G. MHC class II-restricted tumor antigens recognized by CD4+ T cells: new strategies for cancer vaccine design. J Immunother (1997) 2001; 24(3):195-204.
93. Zhang Y, Wang Z, Liu H, Giles F J, Lim S H. Pattern of gene expression and immune responses to Semenogelin 1 in chronic hematologic malignancies. J Immunother 2003; 26(6):461-7.

The invention claimed is:

1. An isolated immunogenic peptide between 9 and 25 amino acids in length comprising at least 9 consecutive amino acids of the amino acid sequence of SEQ ID No. 1.

2. The immunogenic peptide of claim 1, wherein the peptide is capable of stimulating a T-cell response.

3. The immunogenic peptide of claim 1, wherein the peptide is capable of producing a cytotoxic T lymphocyte (CTL) response.

4. The immunogenic peptide of claim 1, wherein the peptide is either 9 or 10 amino acids in length.

5. The immunogenic peptide of claim 1, wherein the peptide consists essentially of the amino acid sequence described in SEQ ID NO: 1.

6. The immunogenic peptide of claim 1, wherein the peptide is capable of producing a T helper ($T_H$) cell response.

7. The immunogenic peptide of claim 6, wherein the peptide is from 18 to 24 amino acids in length.

8. The immunogenic peptide of claim 7, wherein the peptide is 20 amino acids in length.

9. The immunogenic peptide of any one of claims 6 to 8, wherein the peptide consists essentially of the amino acid sequence of SEQ ID NO: 6.

10. A pharmaceutical composition comprising the isolated immunogenic peptide of claim 1.

11. A pharmaceutical composition according to claim 10, further comprising a pharmaceutically acceptable carrier or excipient.

12. A pharmaceutical composition comprising an immunogenic peptide according to claim 1, wherein the immunogenic peptide is capable of producing a cytotoxic T lymphocyte (CTL) response and another immunogenic peptide according to claim 1, wherein the immunogenic peptide is capable of producing a T helper ($T_H$) cell response, for simultaneous, sequential or separate administration.

13. A pharmaceutical composition comprising two or more of the isolated immunogenic peptide of claim 1, for simultaneous, sequential or separate administration.

* * * * *